(12) United States Patent
Stenner-Liewen et al.

(10) Patent No.: US 11,697,680 B2
(45) Date of Patent: Jul. 11, 2023

(54) ANTI-GP73 ANTIBODIES AND IMMUNOCONJUGATES

(71) Applicant: CUREAB GMBH, Riehen (CH)

(72) Inventors: Frank Stenner-Liewen, Riehen (CH); Norbert Markuly, Basel (CH); Heike Liewen, Riehen (CH)

(73) Assignee: CUREAB GMBH, Riehen (CH)

( * ) Notice: Subject to any disclaimer, the term of this patent is extended or adjusted under 35 U.S.C. 154(b) by 952 days.

(21) Appl. No.: 16/461,449

(22) PCT Filed: Nov. 21, 2017

(86) PCT No.: PCT/EP2017/079870
§ 371 (c)(1),
(2) Date: May 16, 2019

(87) PCT Pub. No.: WO2018/091724
PCT Pub. Date: May 24, 2018

(65) Prior Publication Data
US 2021/0253678 A1    Aug. 19, 2021

(30) Foreign Application Priority Data
Nov. 21, 2016   (EP) .................................... 16199882

(51) Int. Cl.
*C07K 16/18*        (2006.01)
*A61K 47/68*        (2017.01)

(52) U.S. Cl.
CPC .......... *C07K 16/18* (2013.01); *A61K 47/6849* (2017.08); *C07K 2317/24* (2013.01); *C07K 2317/31* (2013.01); *C07K 2317/33* (2013.01); *C07K 2317/565* (2013.01)

(58) Field of Classification Search
CPC .............. C07K 16/18; C07K 2317/24; C07K 2317/31; C07K 2317/33; C07K 2317/565; C07K 2317/21; C07K 2317/34; C07K 2317/622; C07K 2317/73; C07K 2317/77; C07K 16/30; A61K 47/6849; A61K 31/5517; A61K 47/6803; A61P 35/00
See application file for complete search history.

(56) References Cited

U.S. PATENT DOCUMENTS

2014/0271651 A1*  9/2014  Tu .................... G01N 33/57438
                                              424/139.1

FOREIGN PATENT DOCUMENTS

| CN | 105699653 A | 6/2016 |
|---|---|---|
| CN | 105734059 A | 7/2016 |
| JP | 2015531750 A | 11/2015 |
| JP | 2016515132 A | 5/2016 |
| JP | 2016533721 A | 11/2016 |
| WO | 2014144355 A2 | 9/2014 |
| WO | 2016037985 A1 | 3/2016 |

OTHER PUBLICATIONS

Chen, X., et al., "mTORC1 Up-Regulates GP73 to Promote Proliferation and Migration of Hepatocellular Carcinoma Cells and Growth of Xenograft Tumors in Mice", Gastroenterology, (2015) 149(3):741-752e14.
Gershoni et al., "Epitope Mapping: The First Step in Developing Epitope-Based Vaccines" Biodrugs—2007.
Author unknown, "IHC-plus™ Anitbodies . . . because seeing is believing", LSBio Aug. 2012 Catalog for LifeSpan BioSciences, Inc., 3 pages.
Ye, Q-H., et al., "GOLM1 Modulates EGFR/RTK Cell-Surface Recycling to Drive Hepatocellular Carcinoma Metastasis", CellPress, 30:444-458 (2016).
Bachert C., et al., "Endosomal Trafficking and Proprotein Convertase Cleavage of cis Golgi Protein GB73 Produces Marker for Hepatocellular Carcinoma", Traffic 8: 1415-1423 (2007).
Zhu, K., et al., "Biomarkers for hepatocellular carcinoma: progression in early diagnosis, prognosis, and personalized therapy", (1):10 (2013), 8 pages.
Du, J., et al., "Screening and Identification of ssDNA Aptamer for Human GP73" Biomed Research International vol. 2015, Article ID 610281, pp. 1-8.
International Search Report and Written Opinion for application PCT/EP2017/079870, dated Jan. 17, 2018, 13 pages.
Riechmann, et al., "Reshaping human antibodies for therapy", Nature 332:323-327 (Mar. 24, 1988).

* cited by examiner

*Primary Examiner* — Nelson B Moseley, II

(57) ABSTRACT

The present invention relates to antigen-binding molecules, preferably antibodies or antigen-binding fragments thereof, that specifically bind to a GP73, or to an antigenic portion thereof, wherein the antigen-binding molecule binds to an epitope within the extracellular part of GP73 that is internalized into a cell usually subsequent to proteolytic cleavage. The invention further relates to immunoconjugates comprising the antigen-binding molecules, in particular the anti-GP73 antibodies, or antigen-binding fragments thereof. The antigen-binding molecules and immunoconjugates of the invention may be administered alone, as a therapeutic conjugate or in combination with other naked antibodies, or with therapeutic agents, or with other immunoconjugates or as a diagnostic conjugate. The present invention also relates to nucleotide sequences encoding anti GP73 antibodies, and immunoconjugates, vectors and host cells containing the nucleotide sequences, and methods of making anti-GP73-antibodies. The antigen-binding molecules, antibodies and compositions of the invention are useful in diagnostic and therapeutic applications for diseases in which expression of GP73 is altered, in particular in which GP73 is overexpressed, such as cancer.

47 Claims, 32 Drawing Sheets

Specification includes a Sequence Listing.

| species | | |
|---|---|---|
| | | 1........................20 |
| Homo sapiens | (NP_057632.2) | SSRSVDLQTRIMELEGRVRR |
| Canis familiaris | (XP_533506.2) | SSRSVDLQTRIVELEGRVRR |
| Mus musculus | (NP_081583.3) | SSRSVELQTRIVELEGRVRR |

B

| | | | |
|---|---|---|---|
| Homo sapiens | (NP_057632.2) | 21/21 | |
| Canis familiaris | (XP_533506.2) | 20/21; | 95% |
| Bos taurus | (NP_001179392.1) | 20/21; | 95% |
| Mus musculus | (NP_081583.3) | 19/21; | 90% |
| Danio reri | (XP_699743.3) | 20/21; | 95% |
| Gallus gallus | (XP_425035.2) | 18/21; | 86% |
| Pan troglodytes | (XP_520104.6) | 21/21; | 100% |
| Rattus norvegicus | (XP_001056825.3) | 19/21; | 90% |

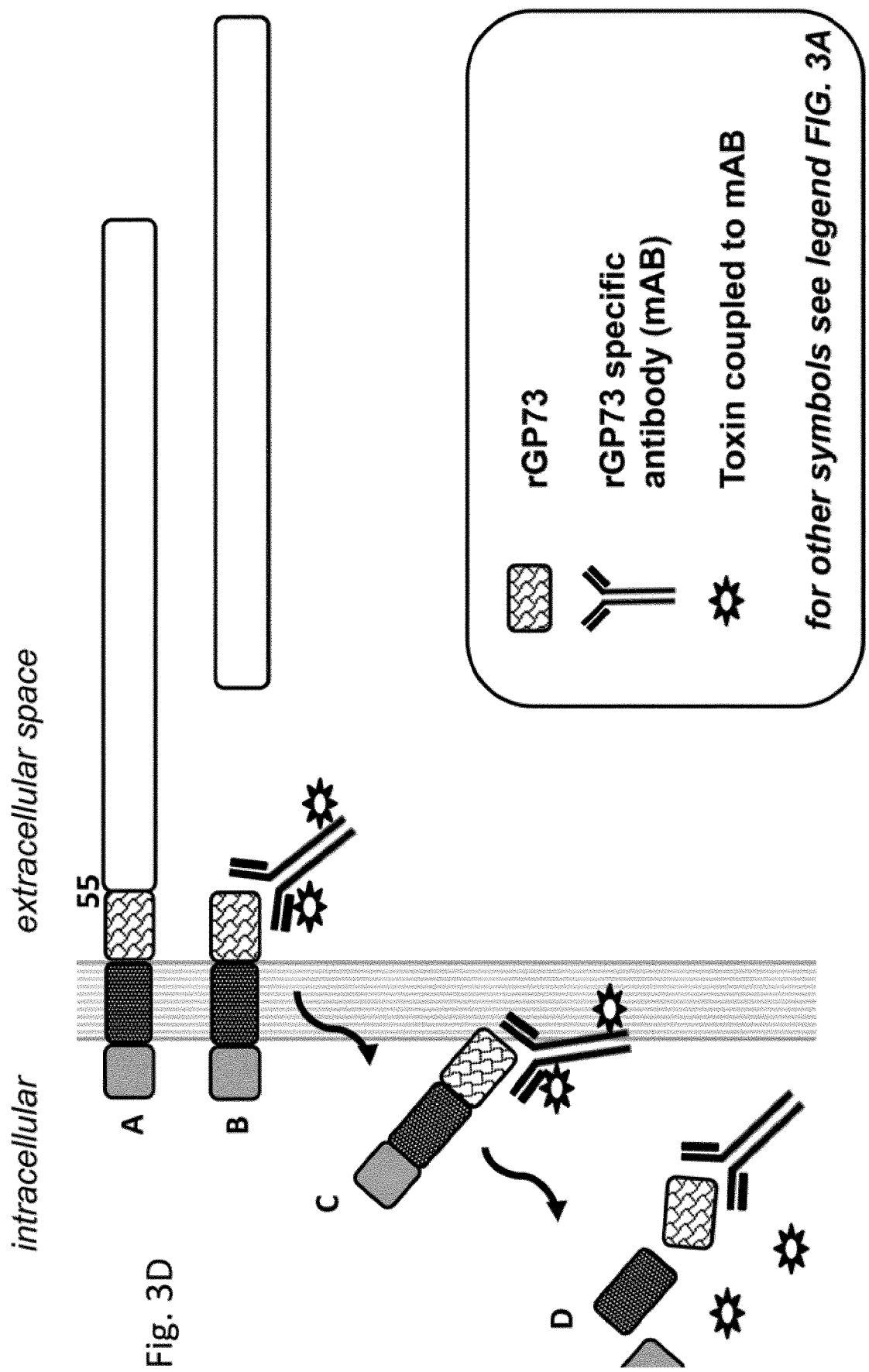

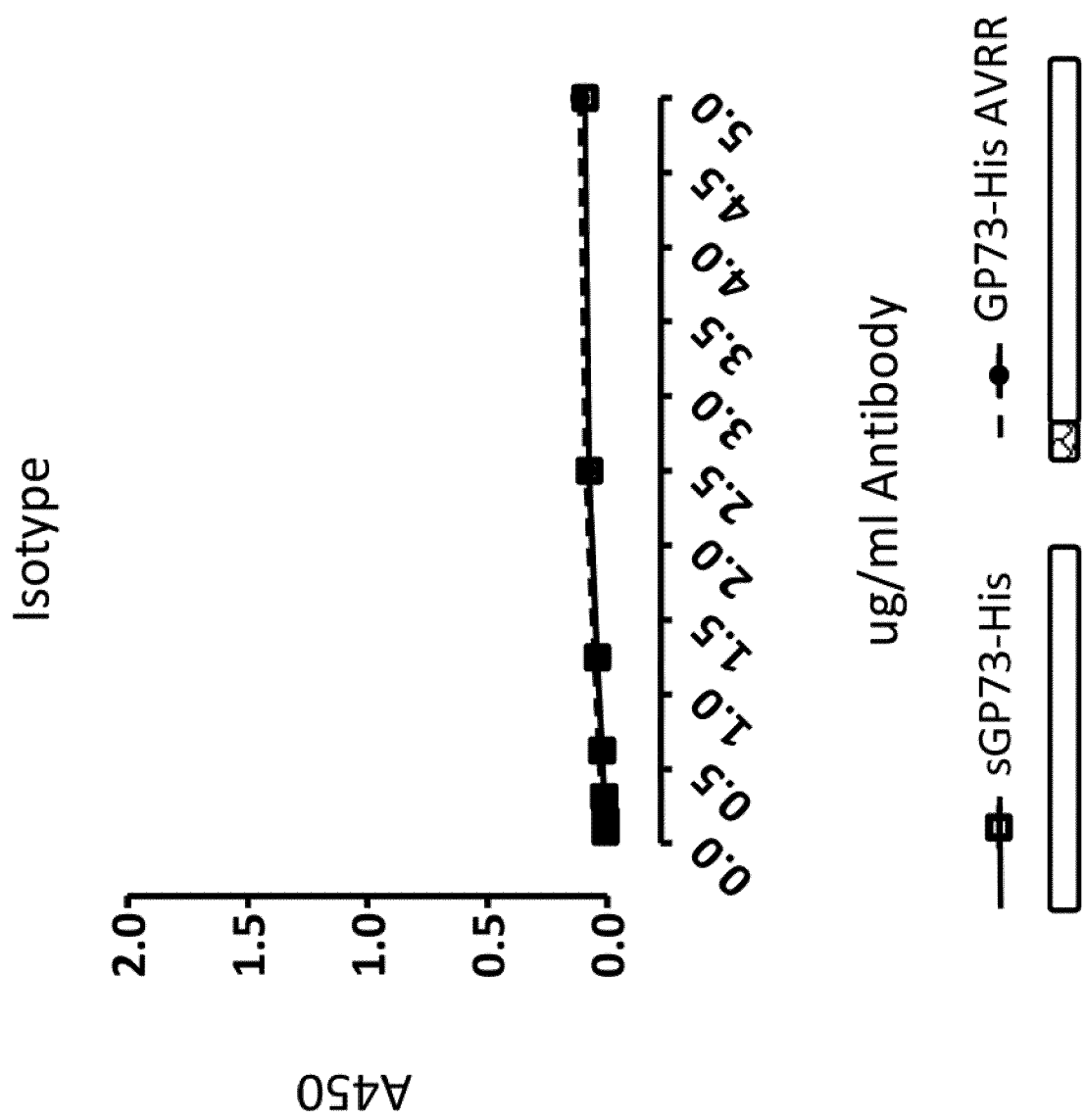

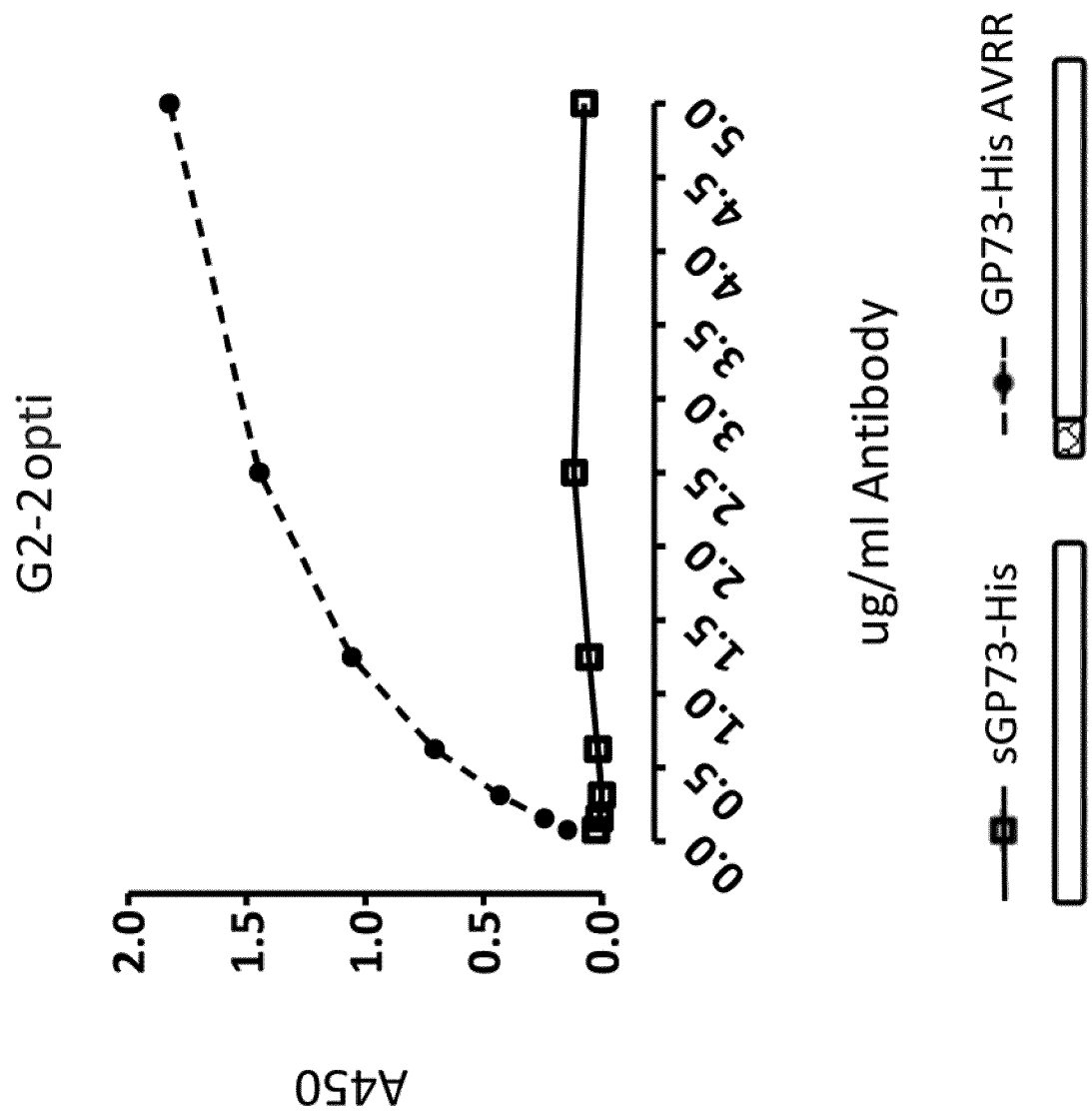

SEQUENCE LISTING

<160> NUMBER OF SEQ ID NOS: 44

<210> SEQ ID NO 1
<211> LENGTH: 401
<212> TYPE: PRT
<213> ORGANISM: Homo sapiens
<220> FEATURE:
<223> OTHER INFORMATION: GP73 UniProtKB Q8NBJ4

<400> SEQUENCE: 1

```
Met Met Gly Leu Gly Asn Gly Arg Arg Ser Met Lys Ser Pro Pro Leu
1               5                   10                  15

Val Leu Ala Ala Leu Val Ala Cys Ile Ile Val Leu Gly Phe Asn Tyr
            20                  25                  30

Trp Ile Ala Ser Ser Arg Ser Val Asp Leu Gln Thr Arg Ile Met Glu
        35                  40                  45

Leu Glu Gly Arg Val Arg Arg Ala Ala Ala Glu Arg Gly Ala Val Glu
    50                  55                  60

Leu Lys Lys Asn Glu Phe Gln Gly Glu Leu Glu Lys Gln Arg Glu Gln
65                  70                  75                  80

Leu Asp Lys Ile Gln Ser Ser His Asn Phe Gln Leu Glu Ser Val Asn
                85                  90                  95

Lys Leu Tyr Gln Asp Glu Lys Ala Val Leu Val Asn Asn Ile Thr Thr
            100                 105                 110

Gly Glu Arg Leu Ile Arg Val Leu Gln Asp Gln Leu Lys Thr Leu Gln
        115                 120                 125

Arg Asn Tyr Gly Arg Leu Gln Gln Asp Val Leu Gln Phe Gln Lys Asn
    130                 135                 140

Gln Thr Asn Leu Glu Arg Lys Phe Ser Tyr Asp Leu Ser Gln Cys Ile
145                 150                 155                 160

Asn Gln Met Lys Glu Val Lys Glu Gln Cys Glu Glu Arg Ile Glu Glu
                165                 170                 175

Val Thr Lys Lys Gly Asn Glu Ala Val Ala Ser Arg Asp Leu Ser Glu
            180                 185                 190

Asn Asn Asp Gln Arg Gln Gln Leu Gln Ala Leu Ser Glu Pro Gln Pro
        195                 200                 205

Arg Leu Gln Ala Ala Gly Leu Pro His Thr Glu Val Pro Gln Gly Lys
    210                 215                 220

Gly Asn Val Leu Gly Asn Ser Lys Ser Gln Thr Pro Ala Pro Ser Ser
225                 230                 235                 240

Glu Val Val Leu Asp Ser Lys Arg Gln Val Glu Lys Glu Glu Thr Asn
                245                 250                 255

Glu Ile Gln Val Val Asn Glu Glu Pro Gln Arg Asp Arg Leu Pro Gln
            260                 265                 270

Glu Pro Gly Arg Glu Gln Val Val Glu Asp Arg Pro Val Gly Gly Arg
        275                 280                 285

Gly Phe Gly Gly Ala Gly Glu Leu Gly Gln Thr Pro Gln Val Gln Ala
    290                 295                 300

Ala Leu Ser Val Ser Gln Glu Asn Pro Glu Met Glu Gly Pro Glu Arg
305                 310                 315                 320

Asp Gln Leu Val Ile Pro Asp Gly Gln Glu Glu Gln Glu Ala Ala
                325                 330                 335

Gly Glu Gly Arg Asn Gln Gln Lys Leu Arg Gly Glu Asp Asp Tyr Asn
            340                 345                 350

Met Asp Glu Asn Glu Ala Glu Ser Glu Thr Asp Lys Gln Ala Ala Leu
```

```
                    355                 360                 365
Ala Gly Asn Asp Arg Asn Ile Asp Val Phe Asn Val Glu Asp Gln Lys
    370                 375                 380

Arg Asp Thr Ile Asn Leu Leu Asp Gln Arg Glu Lys Arg Asn His Thr
385                 390                 395                 400

Leu

<210> SEQ ID NO 2
<211> LENGTH: 117
<212> TYPE: PRT
<213> ORGANISM: Artificial Sequence
<220> FEATURE:
<223> OTHER INFORMATION: G2-2 heavy chain variable region (VH)

<400> SEQUENCE: 2

Glu Val Gln Leu Leu Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ala Gly Met Asp Val Trp Gly Gln Gly Thr Thr
            100                 105                 110

Val Thr Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: G2-2 light chain variable region (VL)

<400> SEQUENCE: 3

Asp Ile Gln Met Thr Gln Pro Ser Ser Leu Ser Ala Ser Pro Gly Ala
1               5                   10                  15

Ser Ala Ser Leu Thr Cys Thr Leu Arg Ser Asp Ile Ser Val Gly Phe
            20                  25                  30

His Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Asp Asp Glu Ala Asp Tyr Tyr Cys
                85                  90                  95

Val Ile Trp His Thr Ser Gly Val Val Phe Gly Gly Thr Lys Val
            100                 105                 110

Glu Ile Lys
        115
```

```
<210> SEQ ID NO 4
<211> LENGTH: 8
<212> TYPE: PRT
<213> ORGANISM: Artificial Sequence
<220> FEATURE:
<223> OTHER INFORMATION: G2-2 HVR-H1

<400> SEQUENCE: 4

Gly Phe Thr Phe Ser Ser Tyr Gly
1               5

<210> SEQ ID NO 5
<211> LENGTH: 8
<212> TYPE: PRT
<213> ORGANISM: Artificial Sequence
<220> FEATURE:
<223> OTHER INFORMATION: G2-2 HVR-H2

<400> SEQUENCE: 5

Ile Ser Tyr Asp Gly Ser Asn Lys
1               5

<210> SEQ ID NO 6
<211> LENGTH: 10
<212> TYPE: PRT
<213> ORGANISM: Artificial Sequence
<220> FEATURE:
<223> OTHER INFORMATION: G2-2 HVR-H3

<400> SEQUENCE: 6

Ala Arg Glu Gly Ser Ala Gly Met Asp Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: G2-2 HVR-L1

<400> SEQUENCE: 7

Ser Asp Ile Ser Val Gly Phe His Arg
1               5

<210> SEQ ID NO 8
<211> LENGTH: 7
<212> TYPE: PRT
<213> ORGANISM: Artificial Sequence
<220> FEATURE:
<223> OTHER INFORMATION: G2-2 HVR-L2

<400> SEQUENCE: 8

Tyr Lys Ser Asp Ser Asp Lys
1               5

<210> SEQ ID NO 9
<211> LENGTH: 9
<212> TYPE: PRT
<213> ORGANISM: Artificial Sequence
<220> FEATURE:
<223> OTHER INFORMATION: G2-2 HVR-L3

<400> SEQUENCE: 9

Val Ile Trp His Thr Ser Gly Val Val
1               5

<210> SEQ ID NO 10
```

```
<211> LENGTH: 123
<212> TYPE: PRT
<213> ORGANISM: Artificial Sequence
<220> FEATURE:
<223> OTHER INFORMATION: G2-1 heavy chain variable region (VH)

<400> SEQUENCE: 10

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Tyr Asp Gly Ser Asn Lys Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Tyr Tyr Asp Ser Ser Gly Tyr Leu Phe Asp Tyr
            100                 105                 110

Trp Gly Gln Gly Thr Leu Val Thr Val Ser Ser
            115                 120

<210> SEQ ID NO 11
<211> LENGTH: 110
<212> TYPE: PRT
<213> ORGANISM: Artificial Sequence
<220> FEATURE:
<223> OTHER INFORMATION: G2-1 light chain variable region (VL)

<400> SEQUENCE: 11

Asp Ile Gln Met Thr Gln Pro His Ser Val Ser Glu Ser Val Gly Lys
1               5                   10                  15

Thr Val Ile Ile Thr Cys Thr Gly Gly Gly Ser Ile Asp Thr Asn
            20                  25                  30

Tyr Val Gln Trp Tyr Gln Gln Arg Pro Gly Ser Ala Pro Val Thr Leu
        35                  40                  45

Ile Tyr Glu Asp Asp Gln Arg Pro Phe Gly Val Pro Asp Arg Phe Ser
    50                  55                  60

Ala Ala Ile Asp Thr Ser Ser Ser Ala Ser Leu Thr Ile Ser Gly
65                  70                  75                  80

Leu Thr Ala Glu Asp Glu Ala Thr Tyr Tyr Cys Gln Ser Ser His Ser
                85                  90                  95

Thr Ala Val Val Phe Gly Gly Gly Thr Lys Val Glu Ile Lys
            100                 105                 110

<210> SEQ ID NO 12
<211> LENGTH: 8
<212> TYPE: PRT
<213> ORGANISM: Artificial Sequence
<220> FEATURE:
<223> OTHER INFORMATION: G2-1 HVR-H1

<400> SEQUENCE: 12

Gly Phe Thr Phe Ser Ser Tyr Ala
1               5

<210> SEQ ID NO 13
<211> LENGTH: 8
```

```
<212> TYPE: PRT
<213> ORGANISM: Artificial Sequence
<220> FEATURE:
<223> OTHER INFORMATION: G2-1 HVR-H2

<400> SEQUENCE: 13

Ile Ser Tyr Asp Gly Ser Asn Lys
1               5

<210> SEQ ID NO 14
<211> LENGTH: 16
<212> TYPE: PRT
<213> ORGANISM: Artificial Sequence
<220> FEATURE:
<223> OTHER INFORMATION: G2-1 HVR-H3

<400> SEQUENCE: 14

Ala Arg Gly Arg Ser Tyr Tyr Asp Ser Ser Gly Tyr Leu Phe Asp Tyr
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: G2-1 HVR-L1

<400> SEQUENCE: 15

Gly Gly Ser Ile Asp Thr Asn Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: G2-1 HVR-L2

<400> SEQUENCE: 16

Glu Asp Asp
1

<210> SEQ ID NO 17
<211> LENGTH: 8
<212> TYPE: PRT
<213> ORGANISM: Artificial Sequence
<220> FEATURE:
<223> OTHER INFORMATION: G2-1 HVR-L3

<400> SEQUENCE: 17

Gln Ser Ser His Ser Thr Ala Val
1               5

<210> SEQ ID NO 18
<211> LENGTH: 122
<212> TYPE: PRT
<213> ORGANISM: Artificial Sequence
<220> FEATURE:
<223> OTHER INFORMATION: G2-4 heavy chain variable region (VH)

<400> SEQUENCE: 18

Gln Val Gln Leu Glu Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
```

```
                35                  40                  45
Gly Phe Ile Arg Asn Lys Ala Lys Gly Tyr Thr Thr Glu Tyr Ser Ala
        50                  55                  60
Ser Val Lys Gly Arg Phe Thr Ile Ser Arg Asp Asn Ser Gln Ser Ile
65                  70                  75                  80
Leu Tyr Leu Gln Met Asn Thr Leu Arg Ala Glu Asp Ser Ala Thr Tyr
                85                  90                  95
Tyr Cys Ala Arg Asp Pro Ser Thr Asn Tyr Trp Tyr Phe Asp Val Trp
            100                 105                 110
Gly Ala Gly Thr Thr Val Thr Val Ser Ser
            115                 120

<210> SEQ ID NO 19
<211> LENGTH: 113
<212> TYPE: PRT
<213> ORGANISM: Artificial Sequence
<220> FEATURE:
<223> OTHER INFORMATION: G2-4 light chain variable region (VL)

<400> SEQUENCE: 19

Asp Ile Val Leu Thr Gln Ser Pro Ser Ser Leu Ala Val Ser Ala Gly
1               5                   10                  15
Glu Lys Val Thr Met Thr Cys Lys Ser Ser Gln Ser Leu Leu Asn Ser
                20                  25                  30
Arg Thr Arg Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Lys Gln
                85                  90                  95
Ser Tyr Asn Leu Tyr Thr Phe Gly Gly Gly Thr Lys Leu Glu Ile Lys
            100                 105                 110
Arg

<210> SEQ ID NO 20
<211> LENGTH: 7
<212> TYPE: PRT
<213> ORGANISM: Artificial Sequence
<220> FEATURE:
<223> OTHER INFORMATION: G2-4 HVR-H1

<400> SEQUENCE: 20

Gly Phe Thr Phe Thr Asp Tyr
1               5

<210> SEQ ID NO 21
<211> LENGTH: 8
<212> TYPE: PRT
<213> ORGANISM: Artificial Sequence
<220> FEATURE:
<223> OTHER INFORMATION: G2-4 HVR-H2

<400> SEQUENCE: 21

Arg Asn Lys Ala Lys Gly Tyr Thr
1               5

<210> SEQ ID NO 22
<211> LENGTH: 11
```

```
<212> TYPE: PRT
<213> ORGANISM: Artificial Sequence
<220> FEATURE:
<223> OTHER INFORMATION: G2-4 HVR-H3

<400> SEQUENCE: 22

Asp Pro Ser Thr Asn Tyr Trp Tyr Phe Asp Val
1               5                   10

<210> SEQ ID NO 23
<211> LENGTH: 17
<212> TYPE: PRT
<213> ORGANISM: Artificial Sequence
<220> FEATURE:
<223> OTHER INFORMATION: G2-4 HVR-L1

<400> SEQUENCE: 23

Lys Ser Ser Gln Ser Leu Leu Asn Ser Arg Thr Arg Lys Asn Tyr Leu
1               5                   10                  15

Ala

<210> SEQ ID NO 24
<211> LENGTH: 7
<212> TYPE: PRT
<213> ORGANISM: Artificial Sequence
<220> FEATURE:
<223> OTHER INFORMATION: G2-4 HVR-L2

<400> SEQUENCE: 24

Trp Ala Ser Thr Arg Glu Ser
1               5

<210> SEQ ID NO 25
<211> LENGTH: 8
<212> TYPE: PRT
<213> ORGANISM: Artificial Sequence
<220> FEATURE:
<223> OTHER INFORMATION: G2-4 HVR-L3

<400> SEQUENCE: 25

Lys Gln Ser Tyr Asn Leu Tyr Thr
1               5

<210> SEQ ID NO 26
<211> LENGTH: 330
<212> TYPE: PRT
<213> ORGANISM: Homo sapiens
<220> FEATURE:
<223> OTHER INFORMATION: G2-2/G2-1 heavy chain constant region (IgG1)

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 107
<212> TYPE: PRT
<213> ORGANISM: Homo sapiens
<220> FEATURE:
<223> OTHER INFORMATION: G2-2/G2-1 light chain constant region (kappa)

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 330

```
<212> TYPE: PRT
<213> ORGANISM: Mus musculus
<220> FEATURE:
<223> OTHER INFORMATION: mG2-2/mG2-1 heavy chain constant region (IgG2a)

<400> SEQUENCE: 28
```

Ala Ser Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

```
<210> SEQ ID NO 29
<211> LENGTH: 393
<212> TYPE: PRT
<213> ORGANISM: Mus musculus
<220> FEATURE:
<223> OTHER INFORMATION: GP73 UniProt Q91XA2

<400> SEQUENCE: 29
```

-continued

```
Met Met Gly Leu Gly Asn Gly Arg Arg Ser Met Lys Ser Pro Pro Leu
 1               5                  10                  15

Ile Leu Ala Ala Leu Val Ala Cys Val Ile Val Leu Gly Phe Asn Tyr
            20                  25                  30

Trp Ile Ala Ser Ser Arg Ser Val Glu Leu Gln Thr Arg Ile Val Glu
        35                  40                  45

Leu Glu Gly Arg Val Arg Ala Ala Glu Arg Gly Ala Val Glu
50                  55                  60

Leu Lys Lys Asn Glu Phe Gln Gly Glu Leu Gln Lys Gln Arg Glu Gln
65                  70                  75                  80

Leu Asp Arg Ile Gln Ser Ser His Ser Phe Leu Glu Asn Val Asn
                85                  90                  95

Lys Leu His Gln Asp Glu Lys Ala Val Leu Val Asn Asn Ile Thr Thr
                100                 105                 110

Gly Glu Lys Leu Ile Arg Asp Leu Gln Asp Gln Leu Lys Ala Leu Gln
                115                 120                 125

Arg Ser Tyr Ser Ser Leu Gln Gln Asp Ile Phe Gln Phe Gln Lys Asn
    130                 135                 140

Gln Thr Ser Leu Glu Lys Lys Phe Ser Tyr Asp Leu Asn Gln Cys Ile
145                 150                 155                 160

Ser Gln Met Thr Glu Val Lys Glu Gln Cys Asp Glu Arg Ile Glu Glu
                165                 170                 175

Val Ile Arg Lys Arg Asn Glu Ala Pro Gly Ser Arg Asp Leu Ala Glu
                180                 185                 190

Thr Asn Asn Gln His Gln Ala Leu Lys Pro Gln Pro Lys Leu Gln
                195                 200                 205

Glu Glu Val Pro Ser Glu Gln Met Pro Gln Glu Lys Gly Asp Val
210                 215                 220

Pro Arg Asn Lys Ser Gln Ile Pro Ala Pro Asn Ser Glu Ser Leu Gly
225                 230                 235                 240

Leu Lys Pro Gln Val Gln Asn Glu Glu Thr Asn Glu Ile Gln Ala Val
                245                 250                 255

Gly Glu Glu His Gln Gln Ala Ser Ile Gln Gly Gln Ala Val Ala Asp
                260                 265                 270

Gly Thr Arg Val Gly Ala Glu Lys Leu Asp Gln His Thr Gln Leu Pro
        275                 280                 285

Ala Gly Leu Leu Ala Arg Pro Glu Glu Asp Ser Gln Tyr Pro Glu Arg
        290                 295                 300

Glu Gln Leu Val Ile Arg Asp Arg Gln Glu Gln Arg Ala Ser Glu
305                 310                 315                 320

Glu Gly Gly Gly Gln Lys Asn Pro Gly Asp Glu Tyr Asp Met Asp Glu
                325                 330                 335

Asn Glu Ala Glu Ser Glu Arg Glu Lys Gln Ala Ala Leu Ala Gly Asn
                340                 345                 350

Asp Arg Asn Ile Asn Val Leu Asn Ala Asp Ala Gln Lys Arg Gly Ile
        355                 360                 365

Ile Asn Val Pro Val Gly Ser Glu Arg Gln Ser His Ile Leu Asn Gln
370                 375                 380

Val Gly Ile His Ile Pro Gln Gln Ala
385                 390

<210> SEQ ID NO 30
<211> LENGTH: 20
```

```
<212> TYPE: PRT
<213> ORGANISM: Homo sapiens
<220> FEATURE:
<223> OTHER INFORMATION: GP73 aa 36 to 55 UniProt Q8NBJ4

<400> SEQUENCE: 30

Ser Ser Arg Ser Val Asp Leu Gln Thr Arg Ile Met Glu Leu Glu Gly
1               5                   10                  15

Arg Val Arg Arg
            20

<210> SEQ ID NO 31
<211> LENGTH: 20
<212> TYPE: PRT
<213> ORGANISM: Mus musculus
<220> FEATURE:
<223> OTHER INFORMATION: GP73 aa 36 to 55 UniProt Q91XA2

<400> SEQUENCE: 31

Ser Ser Arg Ser Val Glu Leu Gln Thr Arg Ile Val Glu Leu Glu Gly
1               5                   10                  15

Arg Val Arg Arg
            20

<210> SEQ ID NO 32
<211> LENGTH: 20
<212> TYPE: PRT
<213> ORGANISM: Canis
<220> FEATURE:
<223> OTHER INFORMATION: GP73 aa 36 to 55 UniProt E2RLA5

<400> SEQUENCE: 32

Ser Ser Arg Ser Val Asp Leu Gln Thr Arg Ile Val Glu Leu Glu Gly
1               5                   10                  15

Arg Val Arg Arg
            20

<210> SEQ ID NO 33
<211> LENGTH: 11
<212> TYPE: PRT
<213> ORGANISM: Homo Sapiens
<220> FEATURE:
<223> OTHER INFORMATION: epitope of antibodies of the invention

<400> SEQUENCE: 33

Arg Ile Met Glu Leu Glu Gly Arg Val Arg Arg
1               5                   10

<210> SEQ ID NO 34
<211> LENGTH: 6
<212> TYPE: PRT
<213> ORGANISM: Homo Sapiens
<220> FEATURE:
<223> OTHER INFORMATION: epitope of antibodies of the invention

<400> SEQUENCE: 34

Glu Gly Arg Val Arg Arg
1               5

<210> SEQ ID NO 35
<211> LENGTH: 117
<212> TYPE: PRT
<213> ORGANISM: Artificial Sequence
<220> FEATURE:
<223> OTHER INFORMATION: G2-2opti (IgG1) and G2-2opti (IgG2a) heavy
      chain variable region (VH)
```

<400> SEQUENCE: 35

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ala Gly Met Asp Val Trp Gly Gln Gly Thr Thr
            100                 105                 110

Val Thr Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: G2-2opti (IgG1) and G2-2opti (IgG2a) light
      chain variable region (VL)

<400> SEQUENCE: 36

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Asp Ile Ser Val Gly Phe
            20                  25                  30

His Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Asp Asp Glu Ala Asp Tyr Tyr Cys
                85                  90                  95

Val Ile Trp His Thr Ser Gly Val Val Phe Gly Gly Gly Thr Lys Leu
            100                 105                 110

Thr Val Leu
        115

<210> SEQ ID NO 37
<211> LENGTH: 123
<212> TYPE: PRT
<213> ORGANISM: Artificial Sequence
<220> FEATURE:
<223> OTHER INFORMATION: G2-1opti (IgG1) and G2-1opti (IgG2a) heavy
      chain variable region (VH)

<400> SEQUENCE: 37

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
                35                  40                  45

Ala Val Ile Ser Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Ser Tyr Tyr Asp Ser Ser Gly Tyr Leu Phe Asp Tyr
                100                 105                 110

Trp Gly Gln Gly Thr Leu Val Thr Val Ser Ser
                115                 120

<210> SEQ ID NO 38
<211> LENGTH: 110
<212> TYPE: PRT
<213> ORGANISM: Artificial Sequence
<220> FEATURE:
<223> OTHER INFORMATION: G2-1opti (IgG1) and G2-1opti (IgG2a) light
      chain variable region (VL)

<400> SEQUENCE: 38

Asn Phe Met Leu Thr Gln Pro His Ser Val Ser Glu Ser Pro Gly Lys
 1               5                  10                  15

Thr Val Ile Ile Thr Cys Thr Gly Gly Gly Ser Ile Asp Thr Asn
                 20                  25                  30

Tyr Val Gln Trp Tyr Gln Gln Arg Pro Gly Ser Ala Pro Val Thr Leu
                 35                  40                  45

Ile Tyr Glu Asp Asp Gln Arg Pro Phe Gly Val Pro Asp Arg Phe Ser
 50                  55                  60

Ala Ala Ile Asp Thr Ser Ser Ser Ala Ser Leu Thr Ile Ser Gly
 65                  70                  75                  80

Leu Thr Ala Glu Asp Glu Ala Asp Tyr Tyr Cys Gln Ser Ser His Ser
                 85                  90                  95

Thr Ala Val Val Phe Gly Gly Gly Thr Lys Leu Thr Val Leu
                100                 105                 110

<210> SEQ ID NO 39
<211> LENGTH: 330
<212> TYPE: PRT
<213> ORGANISM: Artificial Sequence
<220> FEATURE:
<223> OTHER INFORMATION: G2-2opti (IgG2a)/ G2-1opti (IgG2a) heavy chain
      constant region (IgG2a)

<400> SEQUENCE: 39

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

-continued

```
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 40
<211> LENGTH: 357
<212> TYPE: PRT
<213> ORGANISM: Artificial Sequence
<220> FEATURE:
<223> OTHER INFORMATION: GP73 aa 56 to 401-His (sGP73)

<400> SEQUENCE: 40

Ala Ala Ala Glu Arg Gly Ala Val Glu Leu Lys Lys Asn Glu Phe Gln
1               5                   10                  15

Gly Glu Leu Glu Lys Gln Arg Glu Gln Leu Asp Lys Ile Gln Ser Ser
            20                  25                  30

His Asn Phe Gln Leu Glu Ser Val Asn Lys Leu Tyr Gln Asp Glu Lys
        35                  40                  45

Ala Val Leu Val Asn Asn Ile Thr Thr Gly Glu Arg Leu Ile Arg Val
50                  55                  60

Leu Gln Asp Gln Leu Lys Thr Leu Gln Arg Asn Tyr Gly Arg Leu Gln
65                  70                  75                  80

Gln Asp Val Leu Gln Phe Gln Lys Asn Gln Thr Asn Leu Glu Arg Lys
                85                  90                  95

Phe Ser Tyr Asp Leu Ser Gln Cys Ile Asn Gln Met Lys Glu Val Lys
            100                 105                 110

Glu Gln Cys Glu Glu Arg Ile Glu Glu Val Thr Lys Lys Gly Asn Glu
        115                 120                 125
```

Ala Val Ala Ser Arg Asp Leu Ser Glu Asn Asn Asp Gln Arg Gln Gln
            130                 135                 140

Leu Gln Ala Leu Ser Glu Pro Gln Pro Arg Leu Gln Ala Ala Gly Leu
145                 150                 155                 160

Pro His Thr Glu Val Pro Gln Gly Lys Gly Asn Val Leu Gly Asn Ser
                165                 170                 175

Lys Ser Gln Thr Pro Ala Pro Ser Ser Glu Val Val Leu Asp Ser Lys
                180                 185                 190

Arg Gln Val Glu Lys Glu Thr Asn Glu Ile Gln Val Val Asn Glu
                195                 200                 205

Glu Pro Gln Arg Asp Arg Leu Pro Gln Glu Pro Gly Arg Glu Gln Val
210                 215                 220

Val Glu Asp Arg Pro Val Gly Gly Arg Gly Phe Gly Gly Ala Gly Glu
225                 230                 235                 240

Leu Gly Gln Thr Pro Gln Val Gln Ala Ala Leu Ser Val Ser Gln Glu
                245                 250                 255

Asn Pro Glu Met Glu Gly Pro Gly Arg Asp Gln Leu Val Ile Pro Asp
                260                 265                 270

Gly Gln Glu Glu Glu Gln Glu Ala Ala Gly Gly Arg Asn Gln Gln
                275                 280                 285

Lys Leu Arg Gly Glu Asp Asp Tyr Asn Met Asp Glu Asn Glu Ala Glu
290                 295                 300

Ser Glu Thr Asp Lys Gln Ala Ala Leu Ala Gly Asn Asp Arg Asn Ile
305                 310                 315                 320

Asp Val Phe Asn Val Glu Asp Gln Lys Arg Asp Thr Ile Asn Leu Leu
                325                 330                 335

Asp Gln Arg Glu Lys Arg Asn His Thr Leu Ala His His His His
                340                 345                 350

His His His His His
            355

<210> SEQ ID NO 41
<211> LENGTH: 377
<212> TYPE: PRT
<213> ORGANISM: Artificial Sequence
<220> FEATURE:
<223> OTHER INFORMATION: GP73 aa 36 to 401 (R52A)-His (GP73-His AVRR)

<400> SEQUENCE: 41

Ser Ser Arg Ser Val Asp Leu Gln Thr Arg Ile Met Glu Leu Glu Gly
1               5                   10                  15

Ala Val Arg Arg Ala Ala Ala Glu Arg Gly Ala Val Glu Leu Lys Lys
                20                  25                  30

Asn Glu Phe Gln Gly Glu Leu Glu Lys Gln Arg Glu Gln Leu Asp Lys
            35                  40                  45

Ile Gln Ser Ser His Asn Phe Gln Leu Glu Ser Val Asn Lys Leu Tyr
50                  55                  60

Gln Asp Glu Lys Ala Val Leu Val Asn Asn Ile Thr Thr Gly Glu Arg
65                  70                  75                  80

Leu Ile Arg Val Leu Gln Asp Gln Leu Lys Thr Leu Gln Arg Asn Tyr
                85                  90                  95

Gly Arg Leu Gln Gln Asp Val Leu Gln Phe Gln Lys Asn Gln Thr Asn
            100                 105                 110

Leu Glu Arg Lys Phe Ser Tyr Asp Leu Ser Gln Cys Ile Asn Gln Met
            115                 120                 125

Lys Glu Val Lys Glu Gln Cys Glu Glu Arg Ile Glu Glu Val Thr Lys
130                 135                 140

Lys Gly Asn Glu Ala Val Ala Ser Arg Asp Leu Ser Glu Asn Asn Asp
145                 150                 155                 160

Gln Arg Gln Gln Leu Gln Ala Leu Ser Glu Pro Gln Pro Arg Leu Gln
            165                 170                 175

Ala Ala Gly Leu Pro His Thr Glu Val Pro Gln Gly Lys Gly Asn Val
            180                 185                 190

Leu Gly Asn Ser Lys Ser Gln Thr Pro Ala Pro Ser Ser Glu Val Val
            195                 200                 205

Leu Asp Ser Lys Arg Gln Val Glu Lys Glu Glu Thr Asn Glu Ile Gln
210                 215                 220

Val Val Asn Glu Glu Pro Gln Arg Asp Arg Leu Pro Gln Glu Pro Gly
225                 230                 235                 240

Arg Glu Gln Val Val Glu Asp Arg Pro Val Gly Gly Arg Gly Phe Gly
                245                 250                 255

Gly Ala Gly Glu Leu Gly Gln Thr Pro Gln Val Gln Ala Ala Leu Ser
            260                 265                 270

Val Ser Gln Glu Asn Pro Glu Met Glu Gly Pro Glu Arg Asp Gln Leu
            275                 280                 285

Val Ile Pro Asp Gly Gln Glu Glu Gln Glu Ala Ala Gly Glu Gly
290                 295                 300

Arg Asn Gln Gln Lys Leu Arg Gly Glu Asp Asp Tyr Asn Met Asp Glu
305                 310                 315                 320

Asn Glu Ala Glu Ser Glu Thr Asp Lys Gln Ala Ala Leu Ala Gly Asn
                325                 330                 335

Asp Arg Asn Ile Asp Val Phe Asn Val Glu Asp Gln Lys Arg Asp Thr
            340                 345                 350

Ile Asn Leu Leu Asp Gln Arg Glu Lys Arg Asn His Thr Leu Ala His
            355                 360                 365

His His His His His His His His
    370                 375

<210> SEQ ID NO 42
<211> LENGTH: 21
<212> TYPE: PRT
<213> ORGANISM: Artificial Sequence
<220> FEATURE:
<223> OTHER INFORMATION: Endosomal escape domain (EED)

<400> SEQUENCE: 42

Met Val Asp Arg Gly Trp Gly Asn Gly Cys Gly Leu Phe Gly Lys Gly
1               5                   10                  15

Gly Ile Val Gly Ser
            20

<210> SEQ ID NO 43
<211> LENGTH: 6
<212> TYPE: PRT
<213> ORGANISM: Artificial Sequence
<220> FEATURE:
<223> OTHER INFORMATION: EED Linker

<400> SEQUENCE: 43

Ser Ala Ala Ala Gly Thr
1               5

<210> SEQ ID NO 44

```
<211> LENGTH: 9
<212> TYPE: PRT
<213> ORGANISM: Artificial Sequence
<220> FEATURE:
<223> OTHER INFORMATION: G2-1 HVR-L3 variant

<400> SEQUENCE: 44

Gln Ser Ser His Ser Thr Ala Val Val
1               5
```

ANTI-GP73 ANTIBODIES AND IMMUNOCONJUGATES

The present invention relates to antigen-binding molecules, preferably antibodies or antigen-binding fragments thereof, that specifically bind to a GP73, or to an antigenic portion thereof, wherein the antigen-binding molecule binds to an epitope within the extracellular part of GP73 that is internalized into a cell usually subsequent to proteolytic cleavage. The invention further relates to immunoconjugates comprising the antigen-binding molecules, in particular the anti-GP73 antibodies, or antigen-binding fragments thereof. The antigen-binding molecules and immunoconjugates of the invention may be administered alone, as a therapeutic conjugate or in combination with other naked antibodies, or with therapeutic agents, or with other immunoconjugates or as a diagnostic conjugate. The present invention also relates to nucleotide sequences encoding anti GP73 antibodies, and immunoconjugates, vectors and host cells containing the nucleotide sequences, and methods of making anti-GP73-antibodies. The antigen-binding molecules, antibodies and compositions of the invention are useful in diagnostic and therapeutic applications for diseases in which expression of GP73 is altered, in particular in which GP73 is overexpressed, such as cancer.

BACKGROUND OF THE INVENTION

Golgi protein-73 (GP73), alternatively named Golgi Membrane Protein 1 (GOLM1), or Golgi-associated-Phosphoprotein 2 (GOLPH2) is a single pass transmembrane type II protein. Its genuine function is unknown. The genomic sequence of GP73 predicts 11 exons and two splicing variants. The transcript variant 1 (NM_016548.3) is 3100 nt in length and contains exons 2 to 11, while transcript variant 2 (NM_177937.2) is 3092 nt in length and contains exons 1, and 3 to 11. Both variants encode the same open reading frame. The biological significance of these variants is currently not clear; see Kim et al., Golgi phosphoprotein 2 in physiology and in diseases. *Cell & Bioscience* 2012 2:31. Under steady-state conditions GP73 is an integral membrane protein of the cis- and medial-Golgi apparatus. However, GP73 can cycle out of the cis Golgi to endosomes and the cell surface; see Puri S et al. Cycling of early Golgi proteins via the cell surface and endosomes upon lumenal pH disruption *Traffic* 2002, 3:641-653. There is evidence that the endosomal trafficking of GP73 allows for proprotein convertase furin mediated cleavage, resulting in its release into the extracellular space, and provides a molecular explanation for its presence as a serum biomarker for HCC; see Bachert C et al., Endosomal trafficking and proprotein convertase cleavage of cis Golgi protein GP73 produces marker for hepatocellular carcinoma *Traffic* 2007, 8:1415-1423; Marrero J A et al., GP73, a resident Golgi glycoprotein, is a novel serum marker for hepatocellular carcinoma *J Hepatol* 2005, 43:1007-1012; Mao Y et al., Golgi protein 73 (GOLPH2) is a valuable serum marker for hepatocellular carcinoma *Gut* 2010, 59:1687-1693); Li X et al., Serum golgi phosphoprotein 2 level: a better marker than alpha-fetoprotein for diagnosing early hepatocellular carcinoma *Hepatology* 2009, 50:1682 or Zhu et al., Biomarkers for hepatocellular carcinoma: progression in early diagnosis, prognosis, and personalized therapy *Biomark Res* 2013, 1:10. GP73 has been shown to be highly expressed in several malignancies including hepatocellular, cholangiocellular, esophageal, renal, prostate and various other carcinomas but not in adjacent non-tumor tissue. Patients with GP73-positive HCC have a higher tumor grade than patients with GP73-negative HCCs. In bile duct carcinomas (BDC) GP73 expression correlates with better overall survival whereas in HCC GP73 overexpression has been found to be associated with increased risk of metastasis, a higher probability of recurrence and a worse survival; see Riener et al. Golgi phosphoprotein 2 (GOLPH2) expression in liver tumors and its value as a serum marker in hepatocellular carcinomas. *Hepatology* 2009, 49:1602-1609 and Ye et al. 2016, Cancer Cell 30, 444-458 Sep. 12, 2016. Antibodies for targeting GP73 have been described in WO 2014/144355 A2, CN105699653 A and CN105734059 A. The use of antibodies to inhibit GP73 to enhance cell-mediated immunity in cancer patients has been described in WO2012/112798 A1. GP73 has been proposed as a biomarker for diagnosis of lung cancer WO 2011/093675 A2 or as a test in systemic inflammatory conditions e.g. sepsis WO2013/083781 A2. Recently, GP73 (GOLM1) has been described to interact with EGFR/RTK by this promoting growth and metastasis of tumor cells; see Ye et al. 2016, Cancer Cell 30, 444-458 Sep. 12, 2016.

Accordingly, there is a need for agents that target GP73 for the diagnosis and treatment of conditions and diseases that involve altered expression of GP73, such as cancer and infection. The above technical problem is solved by the embodiments as defined in the claims.

SUMMARY OF THE INVENTION

The invention relates to

1. An antigen-binding molecule that specifically binds to GP73, or to an antigenic portion thereof, wherein the antigen-binding molecule binds to an epitope within the amino acid sequence
   a) SSRSVDLQTRIMELEGRVRR SEQ ID NO: 30
   b) SSRSVELQTRIVELEGRVRR SEQ ID NO: 31; and/or
   c) SSRSVDLQTRIVELEGRVRR SEQ ID NO: 32.
2. The antigen-binding molecule of embodiment 1, wherein the epitope is within the amino acid sequence RIMELEGRVRR (SEQ ID NO: 33), preferably EGRVRR (SEQ ID NO: 34).
3. The antigen-binding molecule of embodiment 1 or 2, wherein the antigen-binding molecule is an antibody, an antigen-binding fragment thereof, a bispecific antibody, a designed ankyrin repeat protein (DARPIN), an aptamer or another antibody mimetic.
4. The antigen-binding molecule of embodiment 3, wherein the antibody is a monoclonal antibody, a chimeric antibody, a recombinant antibody, an antigen-binding fragment of a recombinant antibody, a humanized antibody, or an antibody displayed upon the surface of a phage or displayed upon the surface of a chimeric antigen receptor (CAR) T cell.
5. The antigen-binding molecule of embodiment 4, wherein the antibody is an IgG1, IgG2a or IgG2b, IgG3 or IgG4 antibody.
6. The antigen-binding molecule of embodiments 3, 4 or 5, wherein the antibody comprises a variable heavy (VH) chain comprising CDR3 as defined in SEQ ID NO: 6 and a variable light (VL) chain comprising CDR3 as defined in SEQ ID NO: 9.

7. The antigen-binding molecule of any one of embodiments 3 to 6, wherein the antibody
   a) comprises a variable heavy (VH) chain comprising CDR1 as defined in SEQ ID NO: 4, CDR2 as defined in SEQ ID NO: 5 and CDR3 as defined in SEQ ID NO: 6 and a variable light (VL) chain comprising CDR1 as defined in SEQ ID NO: 7, CDR2 as defined in SEQ ID NO: 8 and CDR3 as defined in SEQ ID NO: 9; or
   b) is an antibody binding to the same epitope as an antibody of (a).
8. The antigen-binding molecule of any one of embodiments 3 to 7, wherein the antibody
   a) comprises a variable heavy (VH) chain sequence comprising the amino acid sequence of SEQ ID NO: 2 or SEQ ID NO: 35 or a sequence having 90%, preferably 95% sequence identity to SEQ ID NO: 2 or SEQ ID NO: 35; and
      a variable light (VL) chain sequence comprising the amino acid sequence of SEQ ID NO: 3 or SEQ ID NO: 36 or a sequence having 90%, preferably 95% sequence identity to SEQ ID NO: 3 or SEQ ID NO: 36; or
   b) is an antibody binding to the same epitope as an antibody of (a).
9. The antigen-binding molecule of embodiments 3, 4 or 5, wherein the antibody comprises a variable heavy (VH) chain comprising CDR3 as defined in SEQ ID NO: 14 and a variable light (VL) chain sequence comprising CDR3 as defined in SEQ ID NO: 17.
10. The antigen-binding molecule of embodiments 3, 4, 5 or 9, wherein the antibody
    a) comprises a variable heavy (VH) chain comprising CDR1 as defined in SEQ ID NO: 12, CDR2 as defined in SEQ ID NO: 13 and CDR3 as defined in SEQ ID NO: 14 and a variable light (VL) chain sequence comprising CDR1 as defined in SEQ ID NO: 15, CDR2 as defined in SEQ ID NO: 16 and CDR3 as defined in SEQ ID NO: 17; or
    b) is an antibody binding to the same epitope as an antibody of (a).
11. The antigen-binding molecule of embodiments 3, 4, 5, 9 or 10, wherein the antibody
    a) comprises a variable heavy (VH) chain sequence comprising the amino acid sequence of SEQ ID NO: 10 or of SEQ ID NO: 37 or a sequence having 90%, preferably 95% sequence identity SEQ ID NO: 10 or SEQ ID NO: 37; and
       a variable light (VL) chain sequence comprising the amino acid sequence of SEQ ID NO: 11 or of SEQ ID NO: 38 or a sequence having 90%, preferably 95% sequence identity to SEQ ID NO: 11 or SEQ ID NO: 38; or
    b) is an antibody binding to the same epitope as an antibody of (a).
12. The antigen-binding molecule of embodiment 3, wherein the antigen-binding fragment is a Fab fragment, a F(ab')2 fragment or a Fv fragment.
13. The antigen-binding molecule of any of the preceding embodiments, wherein the antigen-binding molecule is internalized into a cell.
14. A polynucleotide that encodes at least one of a variable heavy (VH) chain sequence and/or a variable light (VL) chain sequence of an antibody that specifically binds to GP73, or to an antigenic portion thereof, wherein the antibody binds to an epitope within the amino acid sequence a)
   SEQ ID NO: 30
   SSRSVDLQTRIMELEGRVRR b)
   SEQ ID NO: 31
   SSRSVELQTRIVELEGRVRR;
   and/or c)
   SEQ ID NO: 32
   SSRSVDLQTRIVELEGRVRR.

15. A host cell comprising the polynucleotide of embodiment 14.
16. A method for producing an antibody comprising culturing the host cell of embodiment 15.
17. A method for producing an antibody that specifically binds to a polypeptide or to an antigenic portion thereof, comprising administering to a subject a polypeptide selected from a)
   SEQ ID NO: 30
   SSRSVDLQTRIMELEGRVRR b)
   SEQ ID NO: 31
   SSRSVELQTRIVELEGRVRR;
   and c)
   SEQ ID NO: 32
   SSRSVDLQTRIVELEGRVRR.

18. An immunoconjugate comprising the antibody of any of the preceding embodiments and a cytotoxic agent or a prodrug of a cytotoxic agent.
19. The immunoconjugate of embodiment 18 having the formula Ab(-L-D)p, wherein:
    a) Ab is the antibody of any of the preceding embodiments;
    b) L is a linker;
    c) D is a cytotoxic agent; and
    d) p ranges from 1-8.
20. The immunoconjugate of embodiments 18 or 19, wherein the cytotoxic agent is selected from a maytansinoid, a calicheamicin, a pyrrolobenzodiazepine and a nemorubicin derivative.
21. The immunoconjugate of embodiment 19, wherein D is a pyrrolobenzodiazepine of Formula A:

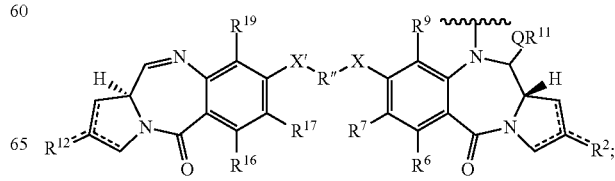

A and salts (e.g., pharmaceutically acceptable salt) and solvates (e.g., pharmaceutically acceptable solvates) thereof, wherein:

the wavy line indicates the covalent attachment site to the linker;

the dotted lines indicate the optional presence of a double bond (the double bond may, e.g., be between C1 and C2 or C2 and C3);

$R^2$ and $R^{12}$ are each independently selected from —H, —OH, =O, =CH$_2$, —CN, —R, —OR, =CH—R$^D$, =C(R$^D$)$_2$, —O—SO$_2$—R, —CO$_2$R, —COR, and -halogen, wherein R$^D$ is independently selected from —H, —CO$_2$R, —C(O)R, CHO, CO$_2$H, —R, —OH, —OR, —SH, —SR, —NH$_2$, —NHR, —NRR', —NO$_2$, Me$_3$Sn— and -halogen;

$R^6$, $R^9$, $R^{16}$ and $R^{19}$ are independently selected from —H, —R, —OH, —OR, —SH, —SR, —NH$_2$, —NHR, —NRR', —NO$_2$, Me$_3$Sn— and -halogen;

$R^7$ and $R^{17}$ are independently selected from —H, —R, —OH, —OR, —SH, —SR, —NH$_2$, —NHR, —NRR', —NO$_2$, Me$_3$Sn— and -halogen;

Q is independently selected from —O—, —S— and —N(H)—;

$R^{11}$ is either —H or —R or, in the case where Q is —O—, $R^{11}$ may be —SO$_3$M, wherein M is an alkali metal or alkaline earth metal cation;

R and R' are each independently selected from optionally substituted $C_{1-12}$ alkyl, $C_{3-8}$ heterocyclyl, $C_{3-20}$ heterocycle and $C_{5-20}$ aryl groups, and, if R and R' are bound to the same nitrogen atom, R and R' may form, together with the nitrogen atom to which they are attached, an optionally substituted 4-, 5-, 6- or 7-membered heterocyclic ring;

R" is a $C_{3-12}$ alkylene group, in which one or more carbon atoms may be replaced by heteroatoms, selected from O, NH and S, and/or aromatic rings that are optionally substituted;

wherein the aromatic rings comprise 5 or 6 carbon atoms and one or two heteroatoms selected from N or NH, and X and X' are independently selected from O, S, and N(H).

22. The immunoconjugate of embodiment 21 wherein D has the structure:

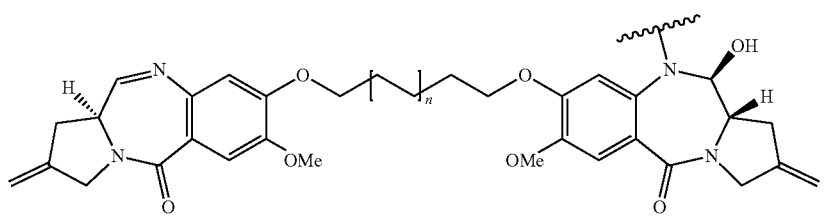

wherein n is 0 or 1.

23. The immunoconjugate of embodiment 19, wherein D is a nemorubicin derivative.

24. The immunoconjugate of embodiment 23, wherein D has a structure selected from:

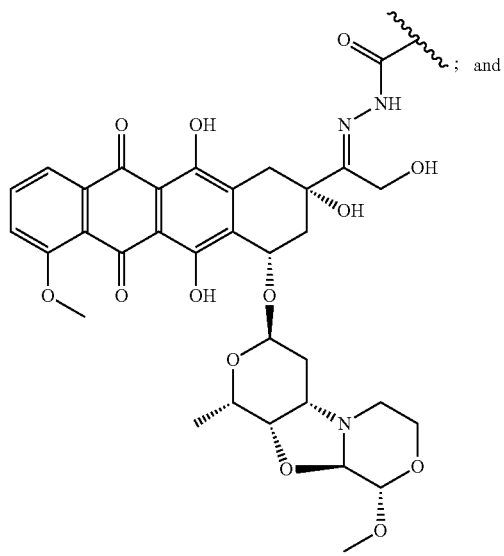

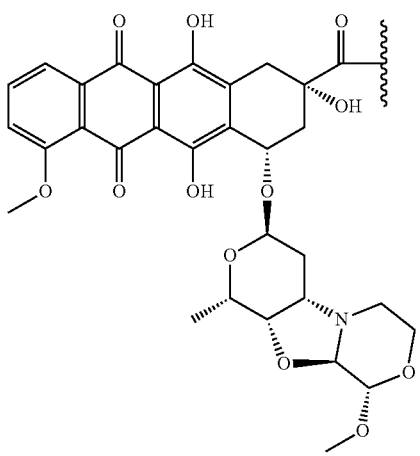

25. The immunoconjugate of any one of embodiments 19 to 24, wherein the linker is cleavable by a protease, is acid-labile and/or comprises hydrazone.

26. The immunoconjugate of embodiment 19 having a formula selected from:

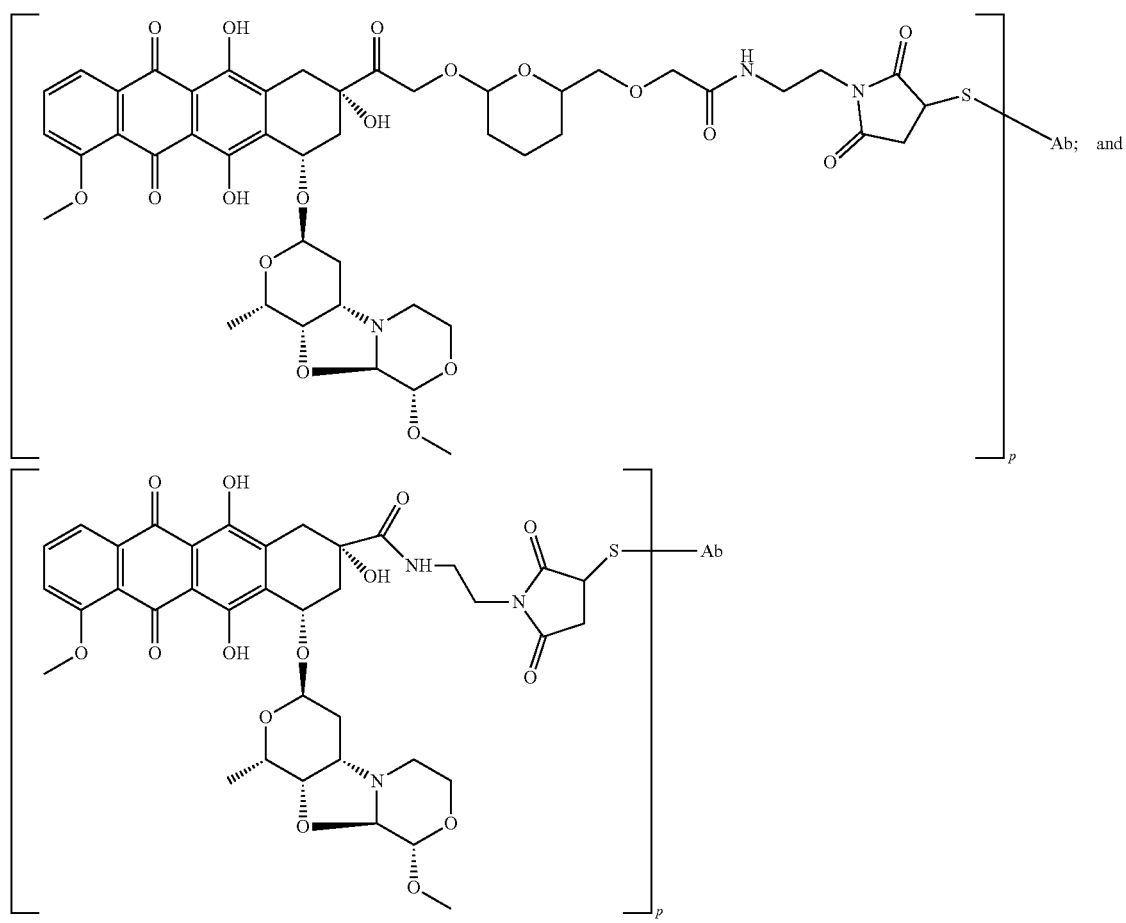

27. The immunoconjugate of embodiment 19 to 26, wherein p ranges from 2-5.
28. An immunoconjugate comprising the antibody of any one of embodiments 1 to 17 and a functional agent, wherein the functional agent preferably is an endosomal escape domain (EED) peptide.
29. The immunoconjugate of embodiment 28 having the formula Ab(-EEDL-EED peptide), wherein Ab is the antibody of any one of embodiments 1 to 17 and EEDL is an EED linker.
30. The immunoconjugate of embodiment 28 or 29, wherein the EED peptide is a Dengue Virus EED peptide comprising the amino acid sequence of SEQ ID NO: 42 and the EED linker comprises the amino acid sequence of SEQ ID NO: 43.
31. A pharmaceutical composition comprising the immunoconjugate of any one of embodiments 18 to 30 and a pharmaceutically acceptable carrier.
32. The pharmaceutical composition of embodiment 31, comprising a further therapeutic agent.
33. A pharmaceutical composition comprising the antigen-binding molecule of any one of embodiments 1 to 13 and a pharmaceutically acceptable carrier.
34. The pharmaceutical composition of embodiment 33, comprising a further therapeutic agent.
35. A method of treating a subject having a GP73-positive cancer, the method comprising administering to the subject an effective amount of the antigen-binding molecule of any one of embodiments 1 to 13, the immunoconjugate of any one of embodiments 18 to 30 or the pharmaceutical composition of any one of embodiments 31 to 34.
36. The method of embodiment 35, wherein the GP73-positive cancer is liver cancer.
37. The method of embodiments 35 or 36 further comprising administering an additional therapeutic agent to the individual.
38. The method of embodiment 35 to 37, wherein administering is intravenous, intraperitoneal, intramuscular, intrasternal, intratumoral, intravesical, intrauterine, intraarticular, intranasal, subcutaneous, topical, as clyster, or as gastric lavage.
39. A method of inhibiting proliferation of a GP73-positive cell, the method comprising exposing the cell to the antigen-binding molecule of any one of embodiments 1 to 13 or the immunoconjugate of any one of embodiments 18 to 30 under conditions permissive for binding of antigen-binding molecule or immunoconjugate to GP73 on the surface of the cell, thereby inhibiting proliferation of the cell.
40. The method of embodiment 39, wherein the cell is a liver cancer cell.
41. A method of detecting human GP73 in a biological sample comprising contacting the biological sample with the antigen-binding molecule of any one of embodiments 1 to 13 under conditions permissive for binding of the antigen-binding molecule to a naturally occurring human GP73, and detecting whether a complex is formed between the antigen-binding molecule and a naturally occurring human GP73 in the biological sample.

42. The method of embodiment 41, wherein the detecting comprises immunohistochemistry, immunofluorescence imaging, enzyme-linked immunosorbent assay (ELISA), and fluorescence-activated cell sorting (FACS), Western Blot, immunoprecipitation, or radiographic imaging.

43. A method for identifying a subject as having disease, comprising determining the level, in a sample from the subject, of specific binding of the antigen-binding molecule of any one of embodiments 1 to 13 with a GP73 polypeptide or with an antigenic portion thereof, wherein detecting an altered level of the specific binding relative to a control sample identifies the subject as having disease.

44. The method of embodiment 43, wherein the disease is cancer.

45. The method of embodiment 43, wherein the cancer is selected from the group of liver cancer, ovarian cancer, endometrium carcinoma, malignant melanoma, prostate cancer, gastric cancer, colorectal carcinoma, lung cancer, leukemia and breast cancer.

46. An RNA aptamer, capable of binding to an epitope within amino acids 36 to 55 of human GP73.

47. A chimeric antigen receptor CAR T-cell, capable of binding to an epitope within amino acids 36 to 55 of human GP73.

48. An antigen-binding molecule that binds to the furin cleavage consensus sequence EGRVRR and inhibits the proteolytic cleavage of GP73 proteins.

49. A composition comprising the antigen-binding molecule of any one of embodiments 1 to 13 and an EGFR antibody or small molecules inhibiting EGFR signaling for use in the treatment of cancer.

50. A bispecific antibody targeting GP73 and EGFR and blocks the EGFR signalling in susceptible cancer cells.

51. An antibody that binds GP73 but not soluble GP73 (sGP73) and is thus not inhibited or neutralized by circulating sGP73.

52. The antigen-binding molecule of any one of embodiments 1 to 13, the immunoconjugate of any one of embodiments 18 to 30 or the pharmaceutical composition of any one of embodiments 31 to 34 for use in treating a disease related to abnormal expression of GP73.

53. The antigen-binding molecule, immunoconjugate or pharmaceutical composition for use according to embodiment 52, wherein the disease is cancer, preferably wherein the cancer is liver cancer, ovarian cancer, endometrium carcinoma, melanoma, prostate cancer, colorectal carcinoma lung cancer, leukemia and breast cancer.

54. The antigen-binding molecule of any one of embodiments 1 to 13, the immunoconjugate of any one of embodiments 18 to 30 or the pharmaceutical composition of any one of embodiments 31 to 34 that reduces the level of circulating, soluble GP73 (sGP73) in the plasma.

55. A method for monitoring the response to treatment of a subject with the antigen-binding molecule of any one of embodiments 1 to 13, the immunoconjugate of any one of embodiments 18 to 30 or the pharmaceutical composition of any one of embodiments 31 to 34, the method comprising measuring the level of circulating sGP73 in the plasma at one or more time points before and at one or more time points after treatment of the subject.

56. The method according to embodiment 55, wherein detecting a reduced level of circulating sGP73 at a time point after treatment relative to a time point before treatment in the plasma of the subject identifies the subject as being responsive to the treatment.

Accordingly, the invention relates to an antigen-binding molecule that specifically binds to GP73, or to an antigenic portion thereof, wherein the antigen-binding molecule binds to an epitope within the amino acid sequence SSRSVDLQTRIMELEGRVRR (SEQ ID NO: 30); SSRSVELQTRIVELEGRVRR (SEQ ID NO: 31); and/or SSRSVDLQTRIVELEGRVRR (SEQ ID NO: 32). Accordingly, the invention provides antigen-binding molecules, in particular antibodies that bind to a particular epitope in the extracellular portion of GP73.

That is, the present invention is based, at least in part, on the surprising discovery that antibodies and antibody-drug conjugates (ADCs) comprising an antibody or antigen-binding fragment thereof that specifically bind GP73 or a processed fragment thereof conjugated to but not limited to e.g. nemorubicin and its derivatives, e.g. PNU-159682 or auristatin e.g. MMAF can be used to kill and/or inhibit proliferation of GP73-expressing cancer cells, and to treat GP73-expressing cancers. Without being bound by theory, it is believed that antigen-binding molecules of the invention bind to a region in the extracellular part of GP73 that is internalized into a cell rather than cleaved off. GP73 is structured in a short cytoplasmic domain, a transmembrane domain and a long extracellular part. This extracellular portion comprises a short region adjacent to the transmembrane domain, named rGP73, that ends in a putative protein cleavage domain at amino acid R55 and the C-terminal part of GP73 named sGP73. The binding-molecules of the present invention target rGP73. Two antibodies were identified that show peak binding activity to rGP73 despite proximity to the cell membrane and the immediate vicinity of protease interaction within this twenty amino acids comprising region.

Accordingly, the invention relates to antigen-binding molecules that specifically bind to said region, i.e. rGP73, in the extracellular part of GP73. In a particular embodiment, the invention relates to an antigen-binding molecule wherein at least part of the binding epitope is within the amino acid sequence EGRVRR within SSRSVDLQTRIMELEGRVRR (SEQ ID NO: 30); SSRSVELQTRIVELEGRVRR (SEQ ID NO: 31); and/or SSRSVDLQTRIVELEGRVRR (SEQ ID NO: 32) of GP73. Again without being bound by theory, it is believed that the amino acid sequence EGRVRR (SEQ ID NO:33) is a putative furin recognition motif. Thus, one potential mode of action of the antigen-binding molecules, in particular antibodies, provided herein is competition with the furin cleavage as shown in FIG. 12 and FIG. 23. The binding of the herein described antibodies, e.g. G2-2, G2-2opti, G2-1, and G2-1opti leads to reduced processing of membrane bound GP73 by furin protease. The expected result is a decrease of soluble GP73, comprising the C-terminal part of the protein, in the environment and in the blood stream as shown in FIG. 23. The interference and disturbance of this furin protease process by the respective antibody binding and blockage of the furin site is likely to be responsible for the proliferation inhibition shown in FIG. 13 and FIG. 24. The novel contribution by the antigen-binding molecules of the invention, e.g. antibodies G2-2, G2-2opti, G2-1 and G2-1opti described herein is the binding at an extracellular part of a shredded protein that remains at the cell surface after processing and secretion of the main portion of GP73 protein. In contrast to hitherto known antibodies that bind circulating sGP73 and would be neutralized by this binding complex, the antigen-binding molecules of the invention, in particular the antibodies disclosed herein are unaffected by sGP73 and reach the cell of origin where they bind the remnant of GP73 and the full length protein of GP73 proximal of the furin cleavage site. This effect is illustrated in FIG. 11. Conditioned media containing sGP73 reduces antibody binding to cell surface of GP73 positive HUH7 cells in case of the distal of the furin cleavage site binding antibody named G2-4. The proximal of the furin cleavage site binding antibody G2-2 is unaffected by the presence of soluble GP73 in the supernatant.

Recently, antibodies that bind to sGP73 have been described in WO 2014/144355 A2. In particular, WO 2014/144355 A2 describes antibodies that bind distal of the furin cleavage site within amino acids 307-339, 276-287, 344-363, or 63-96 of GP73 Similarly, CN105699653 A discloses antibodies that bind within amino acids 56-67 of GP73, i.e. sGP73.

CN105734059 A describes antibodies that bind to GP73 without defining the epitope to which the disclosed antibodies bind to. As shown in the appended Examples, in order to determine binding specificities of antibodies of CN105734059 A, the antibody of CN105734059 A was generated and tested for binding of GP73 with and without the epitope region GP73 AA 36 to 55 as well as for binding of a peptide encompassing the epitope or an unrelated control peptide. As is shown in FIG. 21 and FIG. 22, the epitope of CN105734059 A does not overlap with the epitope of the present invention.

Accordingly, the antibodies of the present invention are advantageous over those known in the art since they are able to bind rGP73 and reach the cell of origin through internalization. This unique property of the antibodies of the present invention allows for specific targeting of tumor cells.

In accordance with the above, the antigen-binding molecules, particular antibodies, of the invention that bind to GP73 have one or more of the following characteristics:
a) bind to an epitope within amino acids 36-55 of human GP73 (SEQ ID NO:1);
b) bind to an epitope spanning the putative furin cleavage recognition motif at amino acids E50 to R55 of human GP73;
c) bind to recombinant human GP73;
d) bind to endogenous GP73 on the surface of a cancer cell;
e) bind to endogenous GP73 on the surface of hepatocellular carcinoma cells;
f) bind to endogenous GP73 on the surface of cells of a cell line selected from HepG2, Hep3B, HuH7, JHH-4, Alexander (PLC/PRF/5), HLE, HuCCT1;
g) bind to endogenous murine GP73 on the surface of cells of a cell line selected from Hep-55.1C, Hepa1-6 (CRL-1830), BpRc1 (CRL-2217), B7IFi1 (CRL-2711), 4T1 (breast cancer);
h) bind to endogenous human GP73 on the surface of cells of a cell line selected from PC3 and DU145 (prostate cancer), MDA-468 (breast cancer), SK-BR-3 (breast cancer), CaCo2, SW480 and HCT 113 (colorectal carcinoma), H1975 (Lung cancer);
i) bind to endogenous human GP73 on the surface of human tumor tissue cells;
j) bind to endogenous human GP73 on the surface of human tumor tissue cells selected from malignant melanoma, endometrium carcinoma, ovarian carcinoma, gastric cancer;
k) bind to endogenous GP73 on the surface of white blood cells, especially but not restricted to granulocytes, lymphocytes, macrophages and dendritic cells;
l) bind to endogenous GP73 on the surface of myeloid cells including myeloid leukemic cells from cell line THP-1; and/or m) bind to uncleaved GP73 on the surface of GP73 expressing cells (mentioned under a-l).

Within the present invention, human GP73 has the amino acid sequence of SEQ ID NO: 1 (full length GP73 variant 1) or human GP73 comprises amino acids 11-401 of SEQ ID NO: 1 (full length GP73 variant 2). SEQ ID NO:1 comprises SEQ ID NO:30, whereas SEQ ID NO:31 and SEQ ID NO:32 are derived from the murine and canine form, respectively, of GP73.

In some embodiments, the antigen-binding molecule of the invention is an antibody, or an antigen-binding portion thereof, a bispecific antibody, or an antigen-binding portion thereof, a designed ankyrin repeat protein (DARPIN), an aptamer or another antibody mimetic, such as affibody molecules, affilins, affimers, affitins, alphabodies, anticalins, avimers, DARPins, fynomers, kunitzdomain peptides, monobodies.

The antibody of the invention can be, inter alia, a monoclonal antibody, a chimeric antibody, a recombinant antibody, an antigen-binding fragment of a recombinant antibody, a humanized antibody, or an antibody displayed upon the surface of a phage or displayed upon the surface of a chimeric antigen receptor (CAR) T cell.

The antibody of the invention can furthermore be an IgG1, IgG2a, IgG2b, IgG3 or IgG4 antibody. In accordance with the above, the antibody of the invention binds to an epitope within amino acids 36-55 of human GP73. In some embodiments, the antibody binds to murine GP73 and/or to canine GP73. Thus, in one embodiment, the invention relates to an antibody comprising a variable heavy (VH) chain comprising CDR3 as defined in SEQ ID NO:6 and a variable light (VL) chain comprising CDR3 as defined in SEQ ID NO:9. The antibodies of the invention may comprise a VH chain comprising CDR1 as defined in SEQ ID NO: 4, CDR2 as defined in SEQ ID NO: 5 and CDR3 as defined in SEQ ID NO: 6 and a VL chain comprising CDR1 as defined in SEQ ID NO: 7, CDR2 as defined in SEQ ID NO: 8 and CDR3 as defined in SEQ ID NO: 9. In some embodiments, the antibody of the invention comprises (a) a VH chain sequence comprising the amino acid sequence of SEQ ID NO: 2, preferably of SEQ ID NO: 35 or a sequence having at least 90%, in particular 95% sequence identity to the amino acid sequence of SEQ ID NO: 2 or SEQ ID NO: 35; and (b) a VL sequence comprising the amino acid sequence of SEQ ID NO: 3, preferably of SEQ ID NO: 36 or a sequence having at least 90%, in particular 95% sequence identity to the amino acid sequence of SEQ ID NO: 3 or SEQ ID NO: 36. In a further embodiment, the present invention relates to an antibody wherein the antibody comprises a variable heavy (VH) chain comprising CDR3 as defined in SEQ ID NO: 14 and a variable light (VL) chain sequence comprising CDR3 as defined in SEQ ID NO: 17. CDR3 of the variable light chain may also be as defined in SEQ ID NO: 44. In a particular embodiment, the antibody may comprise a variable heavy (VH) chain comprising CDR1 as defined in SEQ ID NO: 12, CDR2 as defined in SEQ ID NO: 13 and CDR3 as defined in SEQ ID NO: 14 and a variable light (VL) chain sequence comprising CDR1 as defined in SEQ ID NO: 15, CDR2 as defined in SEQ ID NO: 16 and CDR3 as defined in SEQ ID NO: 17. Again, CDR3 of the VL chain sequence may also be as defined in SEQ ID NO: 44. In a yet further embodiment, the antibody comprises a variable heavy (VH) chain sequence comprising the amino acid sequence of SEQ ID NO: 10, preferably of SEQ ID NO: 37 or a sequence having 90%, in particular 95% sequence identity to SEQ ID NO: 10 or SEQ ID NO: 37; and a variable light (VL) chain sequence comprising the amino acid sequence of SEQ ID NO: 11, preferably of SEQ ID NO: 38 or a sequence having 90%, in particular 95% sequence identity to SEQ ID NO: 11 or SEQ ID NO: 38.

In any of the embodiments described herein, the antibody may be a monoclonal antibody. In any of the embodiments described herein, the antibody may be human, humanized, or chimeric antibody. In any of the embodiments described herein, the antibody may be an antibody fragment that binds GP73. In any of the embodiments described herein, the antibody may be an IgG1, IgG2a or IgG2b, IgG3, IgG4, IgM, IgA1, IgA2, IgAsec, IgD, IgE. As used herein, "isotype" refers to the antibody class (e.g., IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')2 fragment and a Fv fragment.

In certain embodiments, the antibody comprises a heavy chain constant region sequence comprising the amino acid sequence of SEQ ID NO: 28, preferably of SEQ ID NO: 39 (which is a modified version of SEQ ID NO: 28 in order to optimize the expression in mammalian cells) or a sequence having 90%, in particular 95% sequence identity to SEQ ID NO: 28 or SEQ ID NO: 39.

The invention furthermore relates to a polynucleotide encoding an antigen-binding molecule, in particular an antibody, of the invention. In a particular embodiment, the polynucleotide of the invention encodes at least one of a variable heavy (VH) chain sequence and/or a variable light (VL) chain sequence of an antibody that specifically binds to GP73, or to an antigenic portion thereof, wherein the antibody binds to an epitope within the amino acid sequence SSRSVDLQTRIMELEGRVRR (SEQ ID NO: 30); SSRS-VELQTRIVELEGRVRR (SEQ ID NO: 31); and/or SSRSVDLQTRIVELEGRVRR (SEQ ID NO: 32).

The invention furthermore relates to a host cell comprising the polynucleotide of the invention. Furthermore, the invention relates to a method of producing an antibody comprising culturing the host cell of the invention, wherein the host cell comprises the polynucleotide of the invention. In a particular embodiment, the method of producing an antibody comprises culturing the host cell of the invention under conditions suitable to allow efficient production of the antibody of the invention.

The invention furthermore relates to a method for producing an antibody that specifically binds to a polypeptide or to an antigenic portion thereof, comprising administering to a subject a polypeptide selected from SSRSVDLQTRIMELEGRVRR (SEQ ID NO: 30); SSRS-VELQTRIVELEGRVRR (SEQ ID NO: 31); and SSRSVDLQTRIVELEGRVRR (SEQ ID NO: 32).

The invention also relates to an immunoconjugate, comprising the antigen-binding molecule, in particular the antibody, of the invention and an EED peptide, or a cytotoxic agent or a prodrug of a cytotoxic agent.

In some embodiments, the immunoconjugate comprising the antigen-binding molecule and an EED peptide has the formula Ab(-EEDL-EED peptide), wherein Ab is the antibody of the invention and EEDL is a linker. In a preferred embodiment, the EED peptide is a Dengue Virus EED comprising the amino acid sequence of SEQ ID NO: 42. In a certain embodiment, the antigen-binding molecule is attached to the EED peptide through an EED linker comprising the amino acid sequence of SEQ ID NO: 43.

In some embodiments, the immunoconjugate has the formula

Ab(-L-D)$_p$ wherein
Ab is the antibody of the invention;
L is a linker;
D is a cytotoxic agent; and
p is an integer from 1 to 8, preferably an integer from 1 to 6, more preferably an integer from 2 to 5.

The cytotoxic agent is preferably selected from a maytansinoid, a calicheamicin, a dolastatin derivative, which can be an auristatin, e.g. MMAF (also referred to herein as monomethylauristatin F), and a nemorubicin derivative.

A GP73 antibody drug conjugate of the invention (also referred to herein as "GP73 ADC" or "ADC") comprises a human monoclonal antibody to GP73, in particular an antibody of the invention, conjugated to a toxin via a valine-citrulline linker.

D can be a pyrrolobenzodiazepine of Formula A:

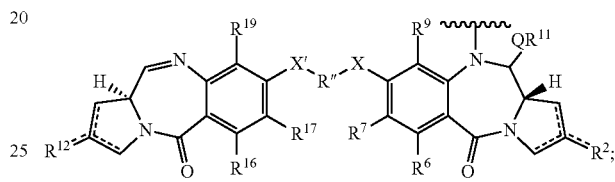

and salts (e.g., pharmaceutically acceptable salt) and solvates (e.g., pharmaceutically acceptable solvates) thereof, wherein:
the wavy line indicates the covalent attachment site to the linker;
the dotted lines indicate the optional presence of a double bond (the double bond may, e.g., be between C1 and C2 or C2 and C3);
$R^2$ and $R^{12}$ are each independently selected from —H, —OH, =O, =CH$_2$, —CN, —R, —OR, =CH—R$^D$, =C(R$^D$)$_2$, —O—SO$_2$—R, —CO$_2$R, —COR, —O—SO$_2$—H, —CO$_2$H, —COH, and -halogen, wherein R$^D$ is independently selected from —H, —CO$_2$R, —C(O)R, CHO, CO$_2$H, —R, —OH, —OR, —SH, —SR, —NH$_2$, —NHR, —NRR', —NO$_2$, Me$_3$Sn— and -halogen;
$R^6$, $R^9$, $R^{16}$ and $R^{19}$ are independently selected from —H, —R, —OH, —OR, —SH, —SR, —NH$_2$, —NHR, —NRR', —NO$_2$, Me$_3$Sn— and -halogen;
$R^7$ and $R^{17}$ are independently selected from —H, —R, —OH, —OR, —SH, —SR, —NH$_2$, —NHR, —NRR', —NO$_2$, Me$_3$Sn— and -halogen;
Q is independently selected from —O—, —S— and —N(H)—;
$R^{11}$ is either —H or —R or, in the case where Q is —O—, $R^{11}$ may be —SO$_3$M, wherein M is an alkali metal or alkaline earth metal cation;
R and R' are each independently selected from optionally substituted C$_{1-12}$ alkyl, C$_{3-8}$ heterocyclyl, C$_{3-20}$ heterocycle and C$_{5-20}$ aryl groups, and, if R and R$^1$ are bound to the same nitrogen atom, R and R' may form, together with the nitrogen atom to which they are attached, an optionally substituted 4-, 5-, 6- or 7-membered heterocyclic ring;
R" is a C$_{3-12}$ alkylene group, in which one or more carbon atoms may be replaced by heteroatoms, selected from O, NH and S, and/or aromatic rings that are optionally substituted;
wherein the aromatic rings comprise 5 or 6 carbon atoms and one or two heteroatoms selected from N or NH, and
X and X' are independently selected from O, S, and N(H).

More preferably, D has the structure

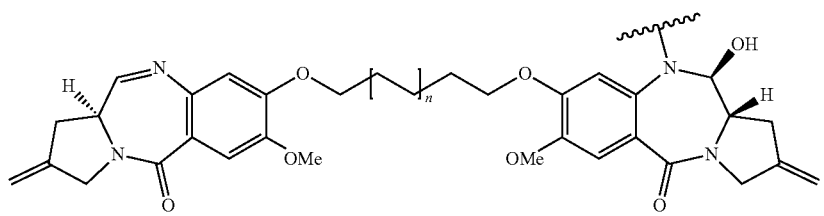

wherein n is 0 or 1.

D may also be a nemorubicin derivate. In this case, D has preferably a structure selected from

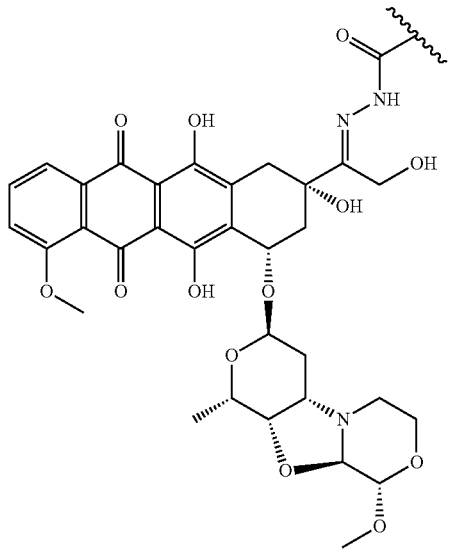

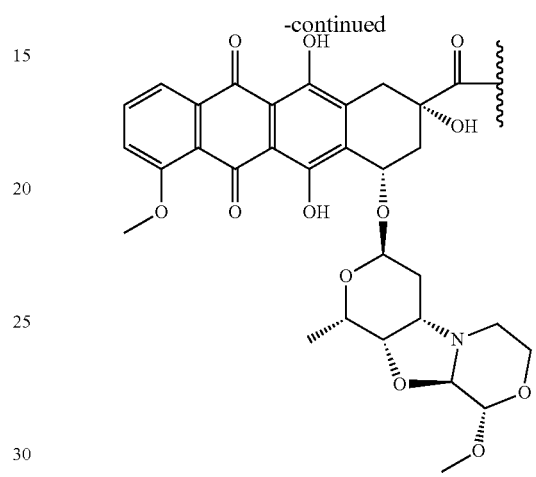

The immunoconjugate of the invention may comprise a linker, wherein the linker is cleavable by a protease. Alternatively, the linker can be acid-labile and/or comprise a hydrazone.

An immunoconjugate comprising an antibody described herein is provided, wherein the immunoconjugate has a formula selected from:

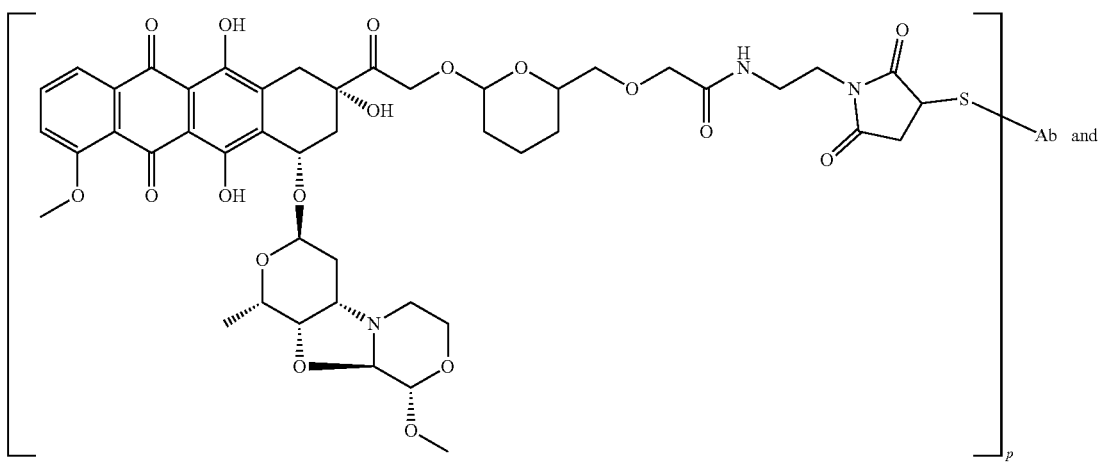

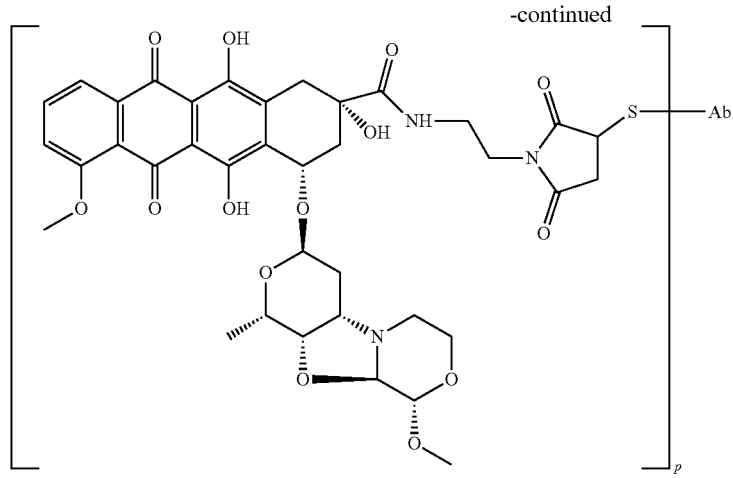

wherein p ranges from 1 to 8, preferably 2 to 5, and Ab is as defined above.

The present invention furthermore relates to a pharmaceutical composition comprising the immunoconjugate of the invention and a pharmaceutically acceptable carrier. In some embodiments, the pharmaceutical formulation comprises an additional therapeutic agent.

In a further embodiment, a pharmaceutical composition is provided comprising the antigen-binding molecule of the invention and a pharmaceutical acceptable carrier. In a particular embodiment, the pharmaceutical composition comprises a further therapeutic agent.

In another aspect, a method for treating a subject having a GP73-positive cancer is provided, comprising administering to the subject an effective amount of the antigen-binding molecule, preferably the antibody, of the invention, or the immunoconjugate of the invention or the pharmaceutical composition of the invention. In a particular embodiment, the immunoconjugate used in such methods comprises the antibody of the invention conjugated to Monomethy Auristatin F (MMAF) or Nemorbicin or a Nemorubicin Metabolite (PNU) or Pyrrolobenzodiazepine (PDB) or another toxin In particular embodiments, the GP73-positive cancer is liver cancer. The method may further comprise administering an additional therapeutic agent to the individual, for example but not restricted to potentially synergistic antibodies like Cetuximab, Trastuzumab or small molecules like Sorafenib, Sunitinib, Regorafinib. Furthermore, combination of the antibodies with conventional chemotherapy effective for the respective GP73 positive tumor may be advantageous. Lastly, the antibodies may be added in the course of interventions, for example surgical resection or tumor embolization procedures as transcatheter arterial chemoembolization (TACE).

Furthermore, the antigen-binding molecule, preferably the antibody, of the invention, or the immunoconjugate of the invention or the pharmaceutical composition of the invention are provided for use in treating a GP73-positive cancer.

In some embodiments, methods of inhibiting proliferation of a GP73-positive cell are provided. Such methods may comprise administering to the individual an effective amount of an antigen-binding molecule of the invention or an immunoconjugate of the invention under conditions permissive for binding of the antigen-binding molecule or immunoconjugate to GP73 on the surface of the cell, thereby inhibiting proliferation of the cell. In some embodiments, inhibition of proliferation may be detected by a method selected from enzyme-linked immunosorbent assay (ELISA), fluorescence-activated cell sorting (FACS) and Western Blot. In some embodiments, the GP73-positive cell is a liver cancer cell.

In some embodiments, methods of detecting human GP73 in a biological sample are provided. The method comprises contacting the biological sample with the antigen-binding molecule of the invention under conditions permissive for binding of the antigen-binding molecule to a naturally occurring human GP73 and detecting whether a complex is formed between the antigen-binding molecule and a naturally occurring human GP73 in the biological sample. In some embodiments detecting may involve a method selected from immunohistochemistry, immunofluorescence imaging, enzyme-linked immunosorbent assay (ELISA), and fluorescence-activated cell sorting. In some embodiments, the biological sample may be a sample comprising liver cancer cells, endometrium carcinoma cells, ovarian carcinoma cells or melanoma cells.

BRIEF DESCRIPTION OF THE FIGURES

FIG. 2 Epitope across species: Shown are homologies of the GP73 antigen in different species FIG. 3A Scheme of organization of GP73 protein. The intracellular part of GP73 is denoted as iGP73. The transmembrane part of GP73 is denoted as tGP73. rGP73 marks a remnant of GP73 that resides in the extracellular space bound to the cell membrane after proteolytic cleavage and is later internalized into the cell. This is the specific epitope of the antigen-binding molecules, in particular antibodies, of the invention. sGP73 is the cleaved and soluble part of GP73. Putative secondary modification sites at amino acids N109, N144, C159, C170, O218, O235 and N398 are marked.

A peptide ELISA was performed using horse radish peroxidase labeled G2-1 (G2-1-HRP) or G2-2 (G2-2-HRP) as binding antibodies and G2-1 or G2-2 as competing antibodies. Competitive inhibition is shown for G2-1 with G2-2-HRP and G2-2 with G2-1-HRP (filled triangles). Binding to peptide AA 36-55 of GP73 served as positive control (filled circle), negative control was binding to an unrelated peptide (filled diamond) as described in Example 5.

Figure 9:
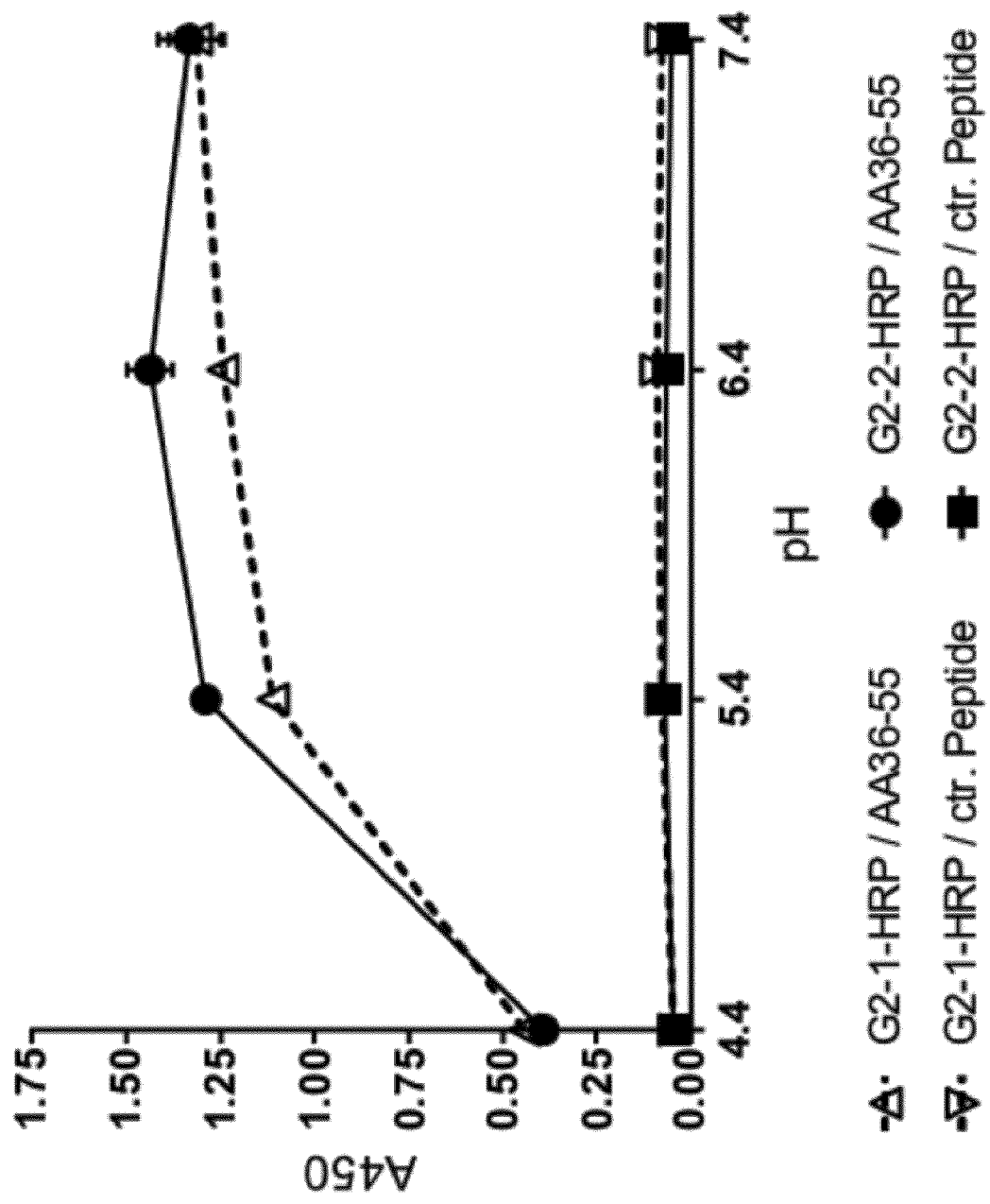

FIG. 9 pH dependent peptide binding of G2-1 and G2-2

A peptide ELISA was performed to test for pH dependency of binding to peptide AA 36-55 of GP73. Stable binding for both antibodies G2-1 and G2-2 is demonstrated in a pH range of 7.4 to 5.4 as described in Example 5.

Figure 10:
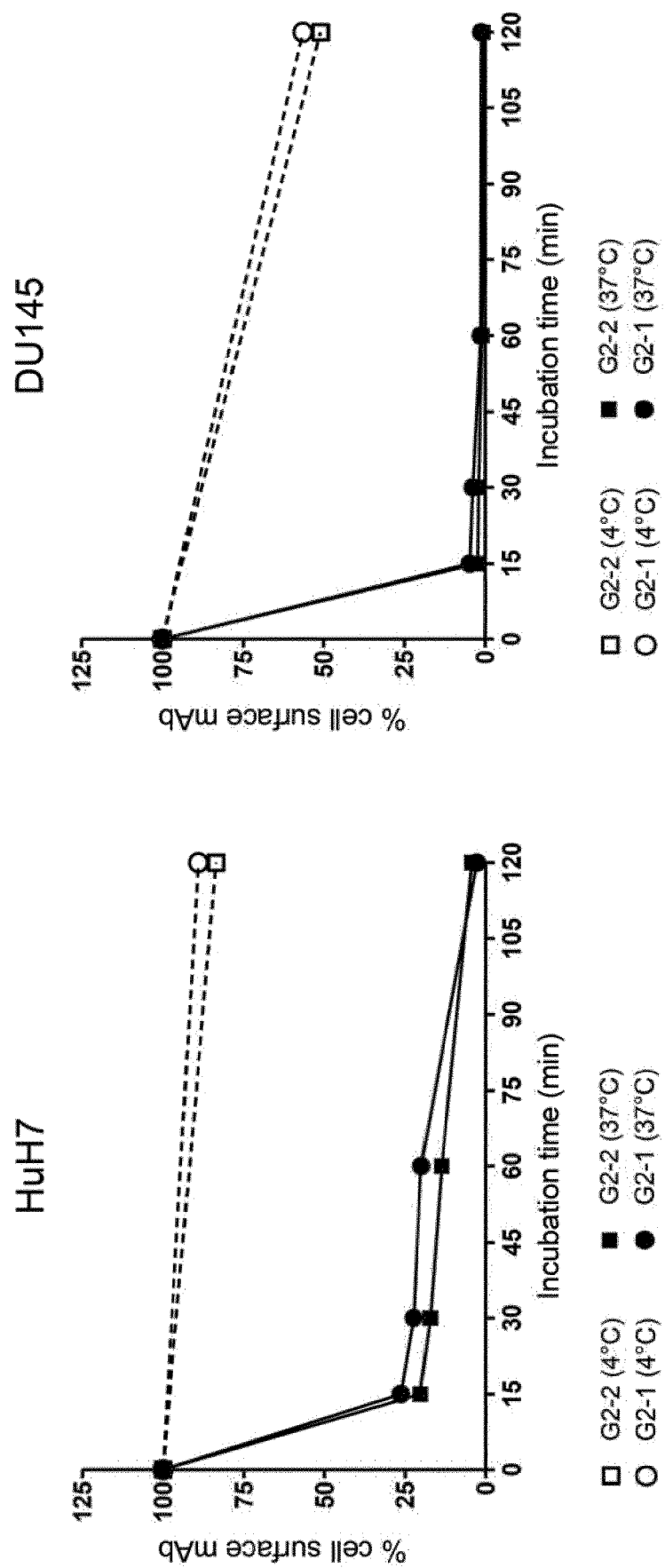

FIG. 10 Internalization experiment of G2-2 and G2-1 by flow cytometry

Internalization of G2-2 into the murin hepatoma cell line and the human prostate cancer cell line DU145 is tested by flow cytometry. After 15 minutes cell surface detection of G2-2 and G2-1 dropped under 30% indicating rapid internalization at 37° C. as described in Example 6.

Figure 11:
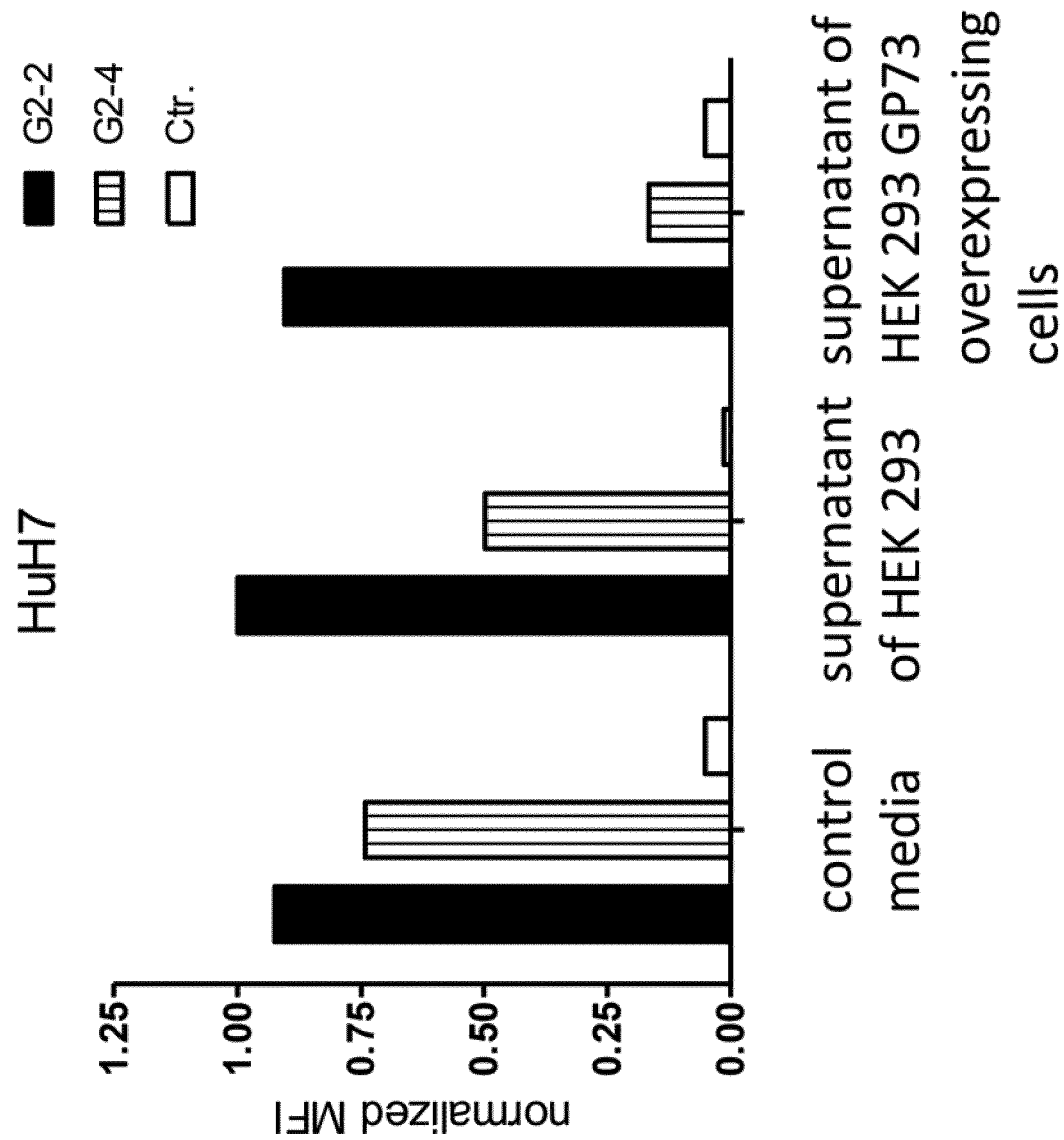

FIG. 11 Internalization of G2-2 and controls depending on cell environment

Antibody internalization was measured by FACS using the pH-sensitive dye pHrodo Green coupled to each antibody. The dye exhibits fluorescence only under pH 5.4 ie after internalization and translocation of the antibody to endosomes. Preincubation with conditioned media containing soluble GP73 reduces internalization of G2-4, an antibody that binds to the c-terminal part of sGP73. The internalization of G2-2 that binds to rGP73 is not altered as described in Example 6.

Figure 12:
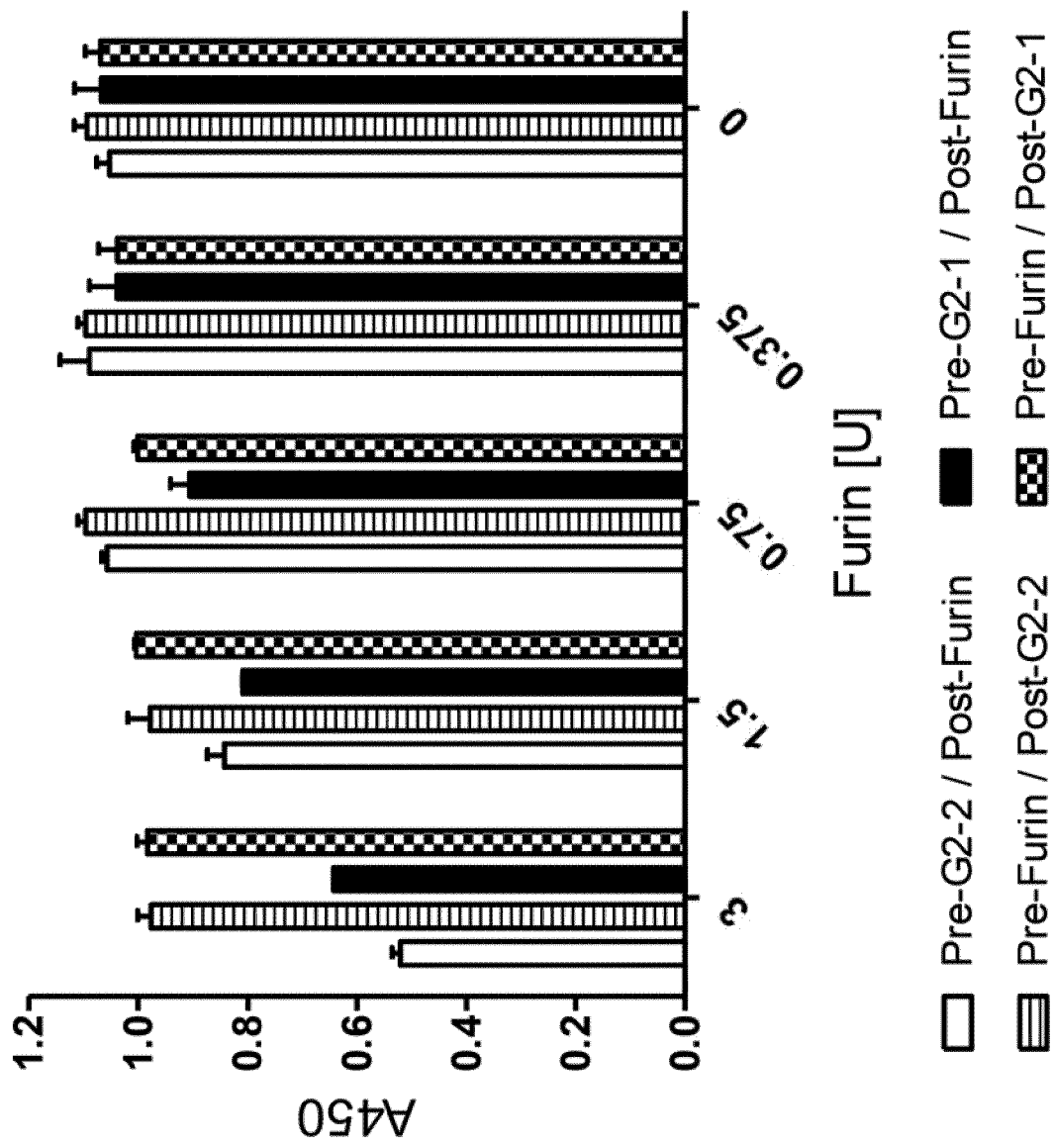

FIG. 12 Furin cleavage quantification depending on G2-2 or G2-1 binding to GP73

Measurements of Furin cleavage of GP73 using a range from 0 units to 3 units of Furin are depicted. Preincubation with G2-2 or G2-1 leads to a significant reduction in Furin cleavage (3 U and 1.5 U) as described in Example 7.

Figure 13A:
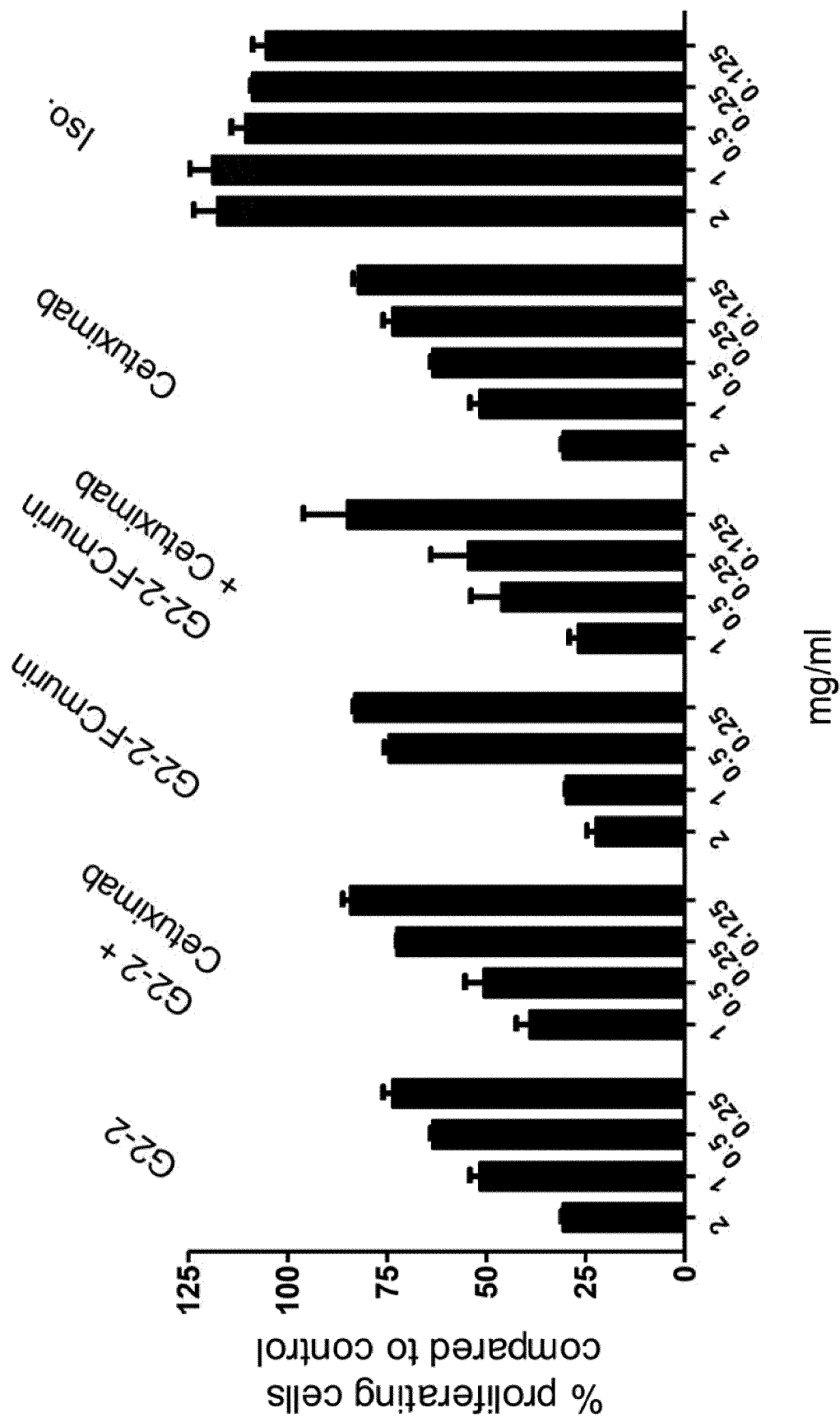
Figure 13:
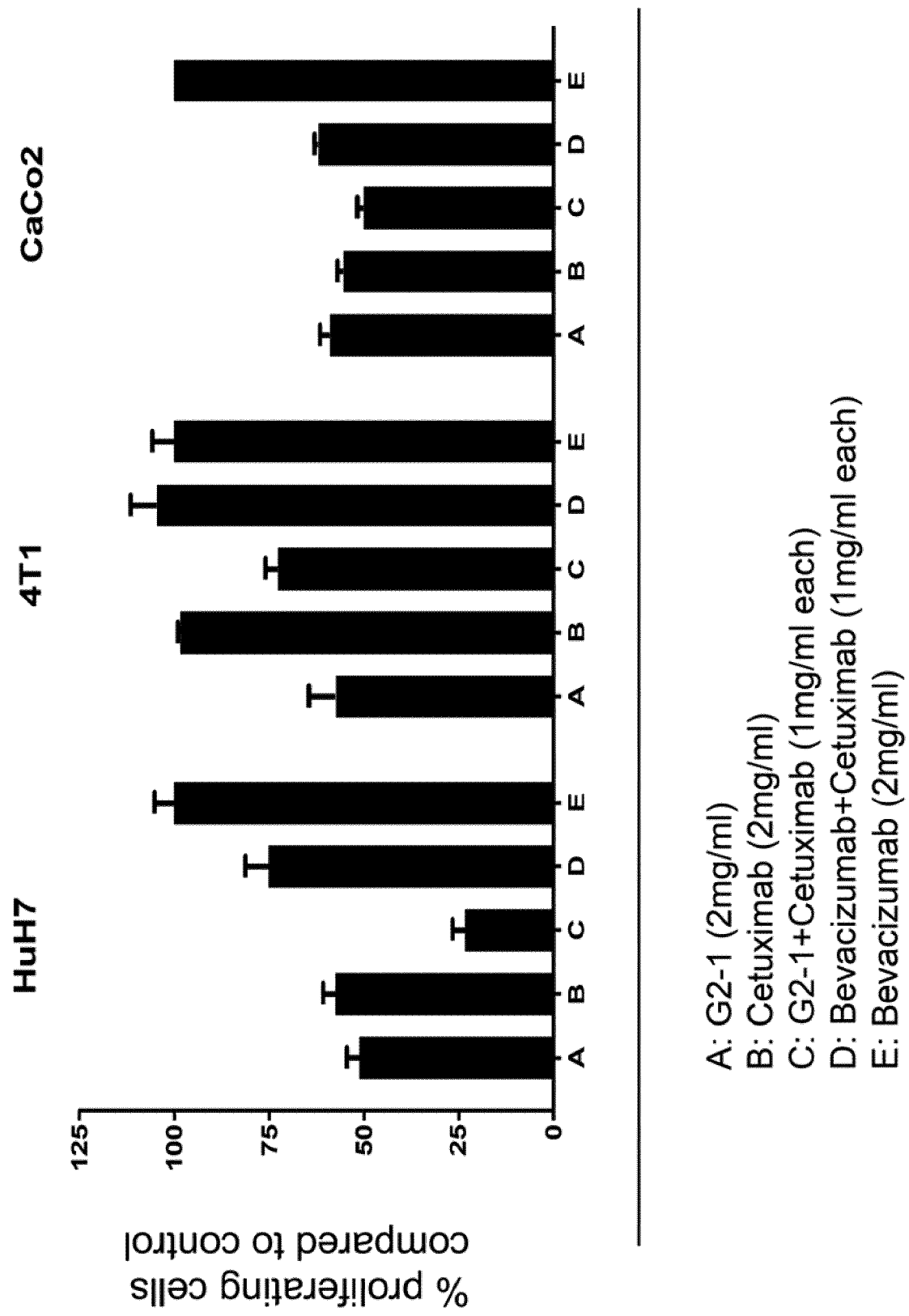

FIG. 13A Proliferation of HuH7 cells (human hepatocellular carcinoma) after treatment with different antibodies. HuH7 cells were treated with G2-2, G2-2 plus Cetuximab, mG2-2, mG2-2 plus Cetuximab, Cetuximab or control antibody each in increasing concentrations from 0.125 mg/ml to 2 mg/ml. Proliferating cells were measured after 72 hrs. Cell proliferation was reduced depending on antibody concentration. This effect was independent of the Fc part i.e. human IgG1 in G2-2 or murin IgG2a in mG2-2 as described in Example 8.

FIG. 13B Proliferation of HuH7 cells (human hepatocellular carcinoma), 4T1 cells (murin breast carcinoma) and CaCo2 cells (human colorectal carcinoma) after treatment with different antibodies. The three cell lines were treated with G2-1, G2-1 plus Cetuximab, Cetuximab, Bevacizumab or Bevacizumab plus Cetuximab 2 mg/ml total. Proliferating cells were measured after 72 hrs. There is a additive effect of G2-1 and Cetuximab in HuH7 cells as described in Example 8.

Figure 14:
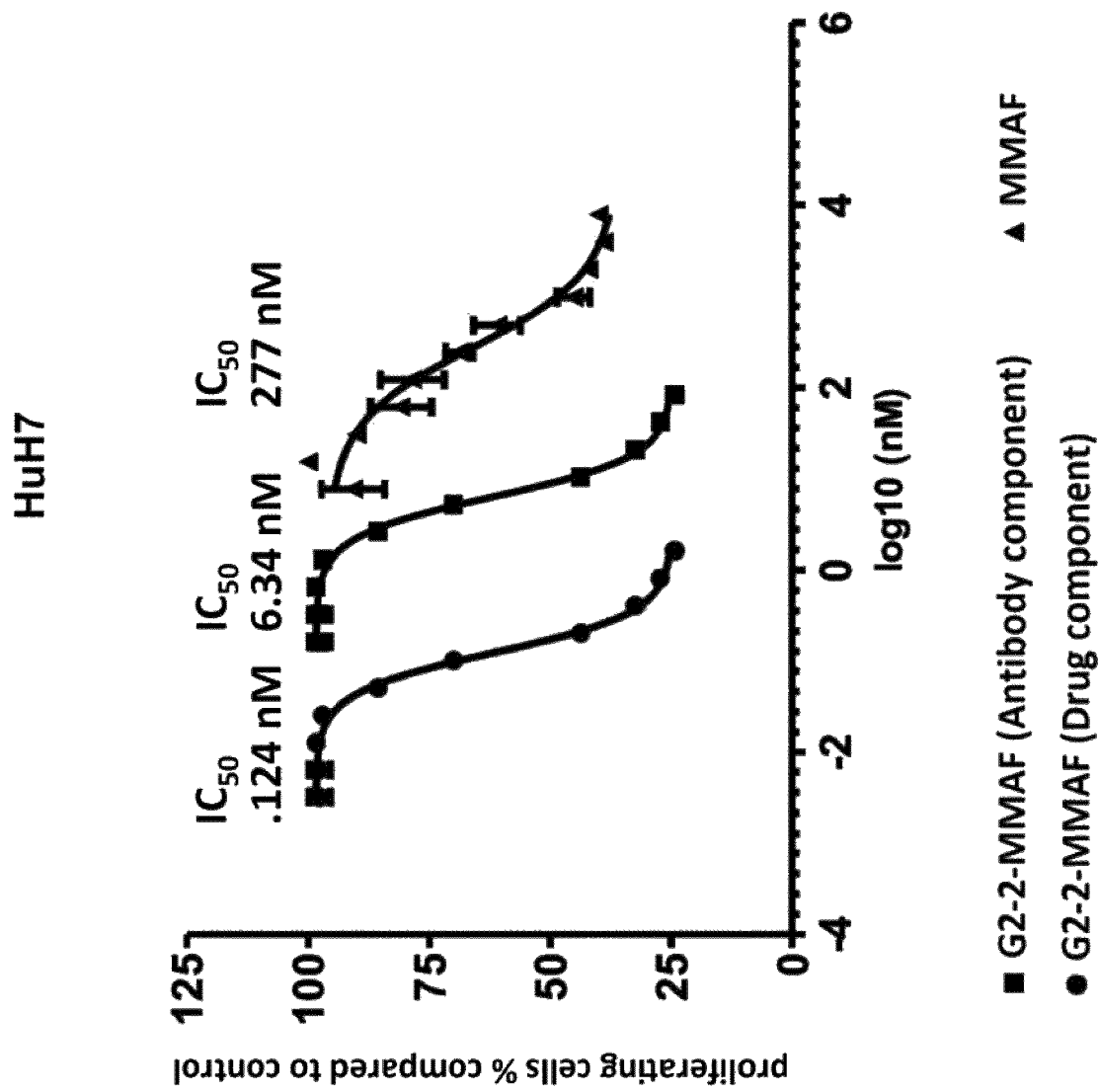

FIG. 14 An antibody drug conjugate consisting of MMAF attached to a Malamide exchange linker linked to G2-2 was added to HuH7 cells. The right curve (triangles) shows toxicity of MMAF as determined by drug component IC50 277 nM. The middle curve (squares) shows G2-2-Mal-VC-PAB-MMAF with an IC50 of 6.34 nM as determined by antibody component. The left curve (circles) shows G2-2-Mal-VC-PAB-MMAF with an IC50 of 0.124 nM as determined by drug component as described in Example 9 and 10.

Figure 15:
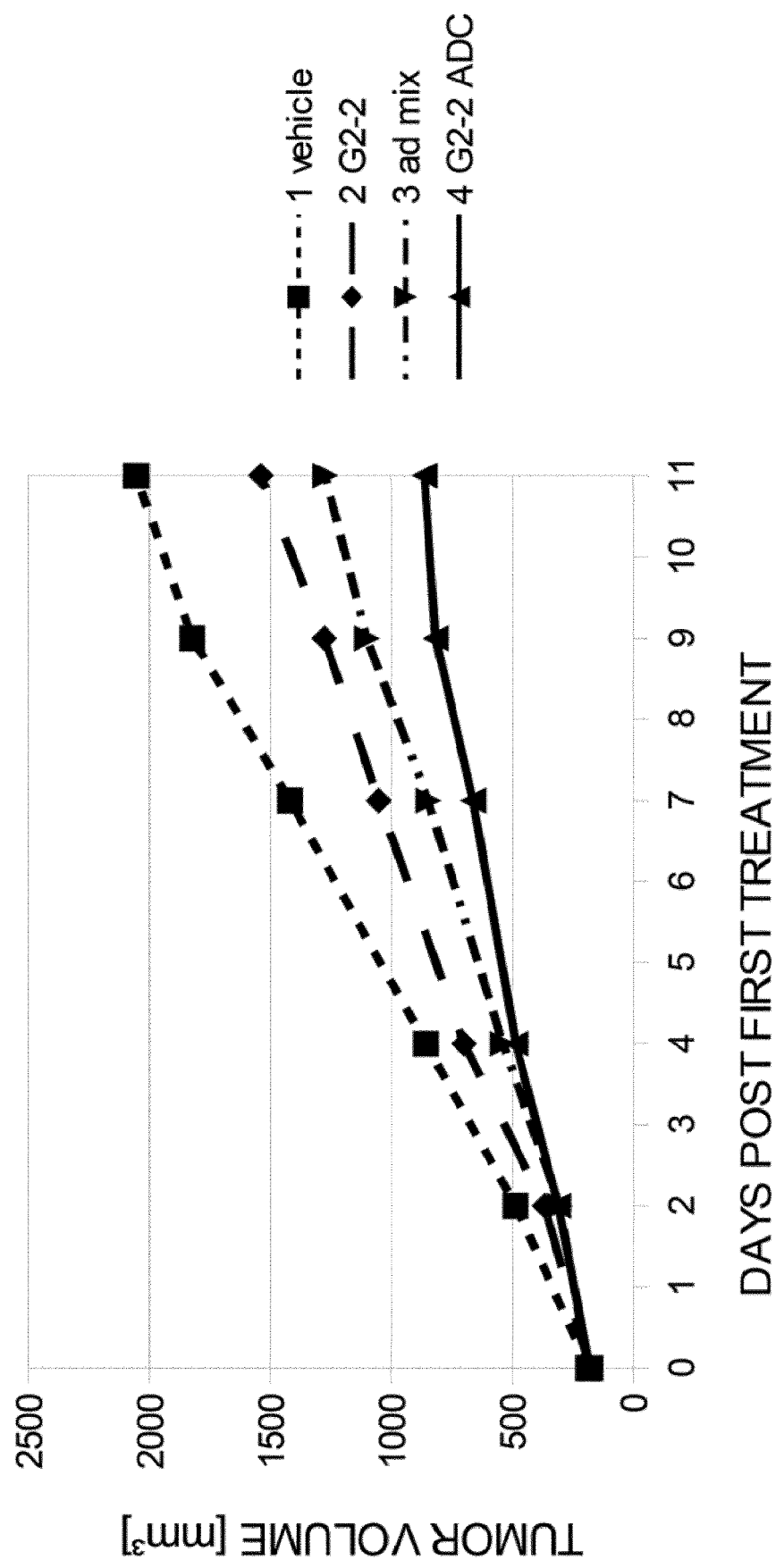

FIG. 15 Tumor growth model of HuH7 xenograft mouse model. Bulb/c naked mice bearing subcutaneous human hepatocellular carcinoma (HuH7) were treated with 2 mg/kg G2-2-PNU (ADC) at day 0 and 1 mg/kg G2-2-PNU on day 7, 2 mg/g G2-2 on day 0 and day 7 (naked mAB), G2-2 (naked mAB) and PNU (ad mix) or PBS (vehicle) twice, on day 1 and day 7. The difference in tumor growth between ADC and vehicle group is statistically significant at day 21 (one-way ANOVA p=0.5; SPSS 18.0) as described in Example 11.

Figure 16:
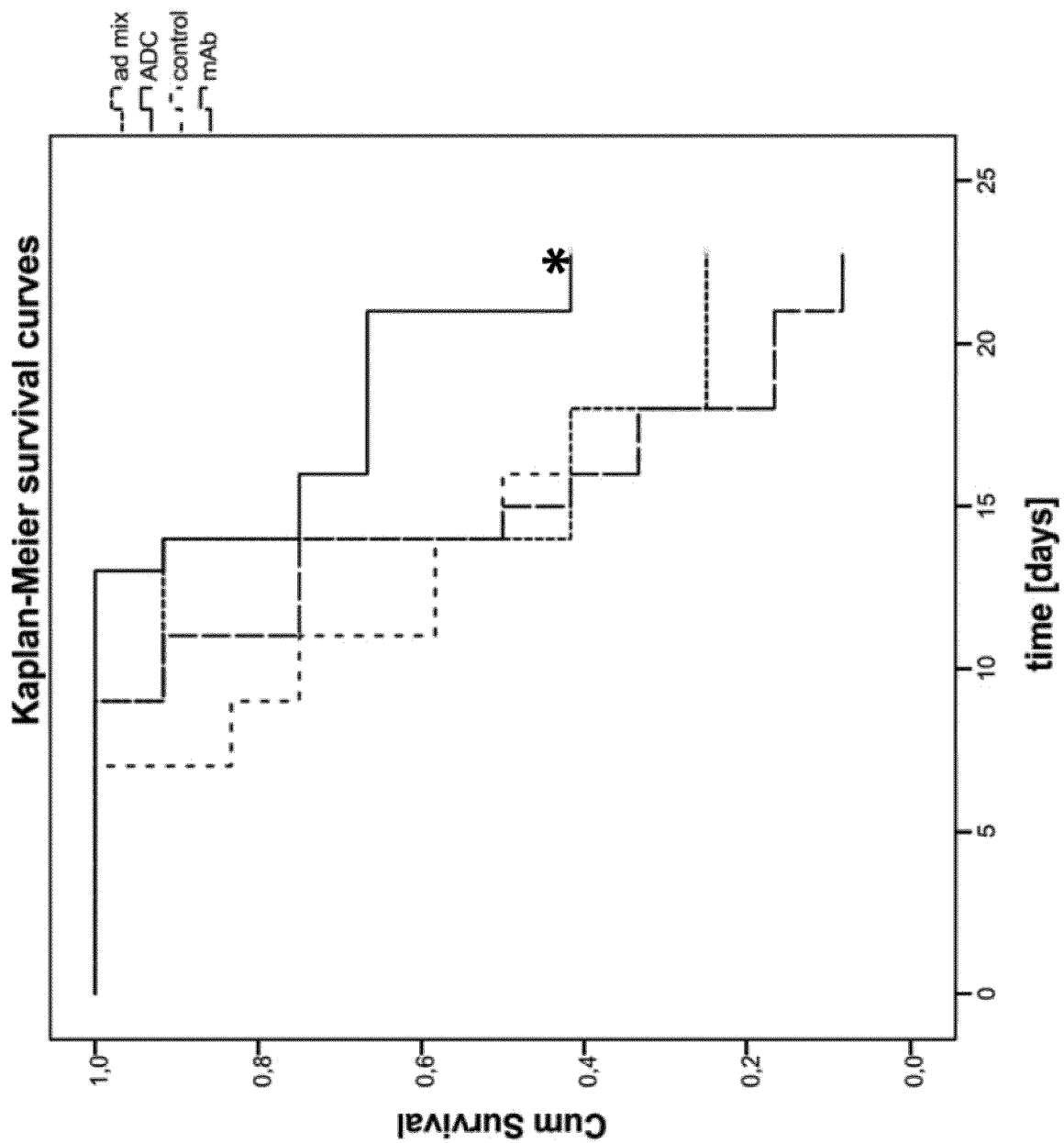

FIG. 16 Kaplan Meyer Survival Curves of the HUH7 xenograft mouse model. The difference in survival between ADC and vehicle group is statistically significant (Log Rank/Breslow/Tarone-Ware p=0.02; SPSS 18.0)

Figure 17:
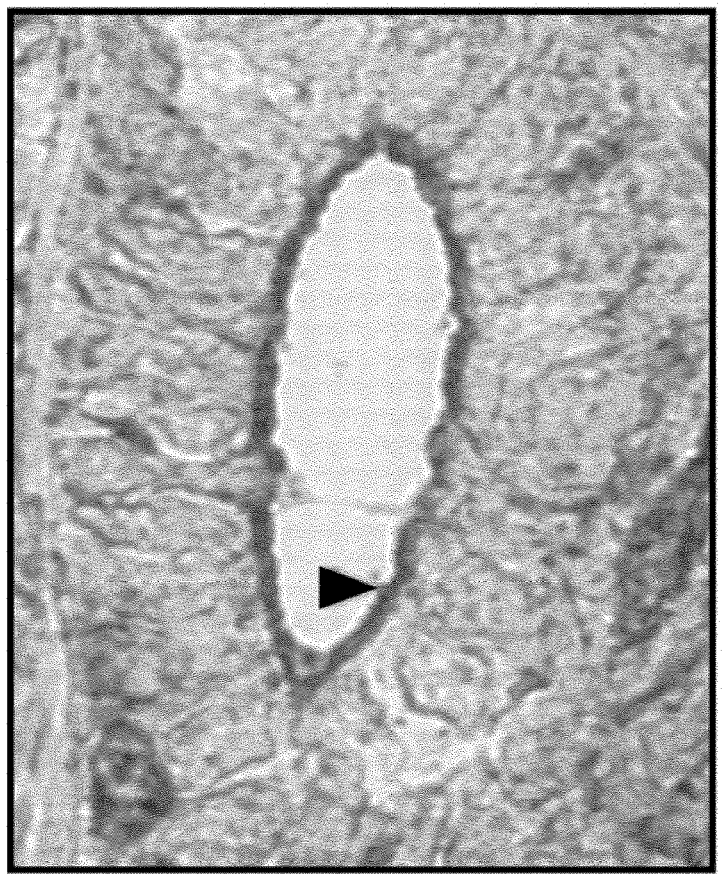
Figure 17:

FIG. 17 Immunohistochemistry: Ovarian carcinoma stained with anti-GP73 antibody MO6 (Sigma) and mG2-2 followed by secondary staining with anti-mouse antibodies and examination under a microscope at 100× magnification as described in Example 3.

Figure 18:
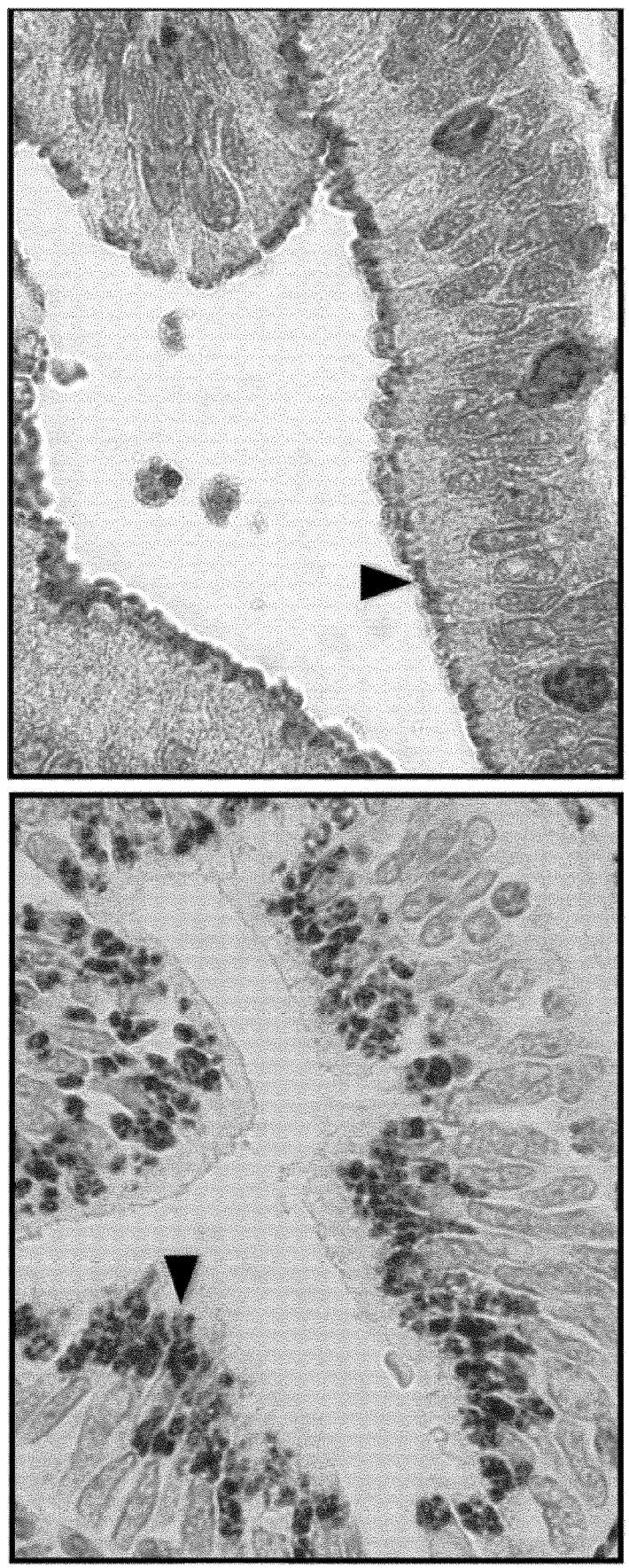

FIG. 18 Immunohistochemistry: Endometrium carcinoma stained with M06 and mG2-2 followed by secondary staining with anti-mouse antibodies and examination under a microscope at 100× magnification as described in Example 3.

Figure 19:
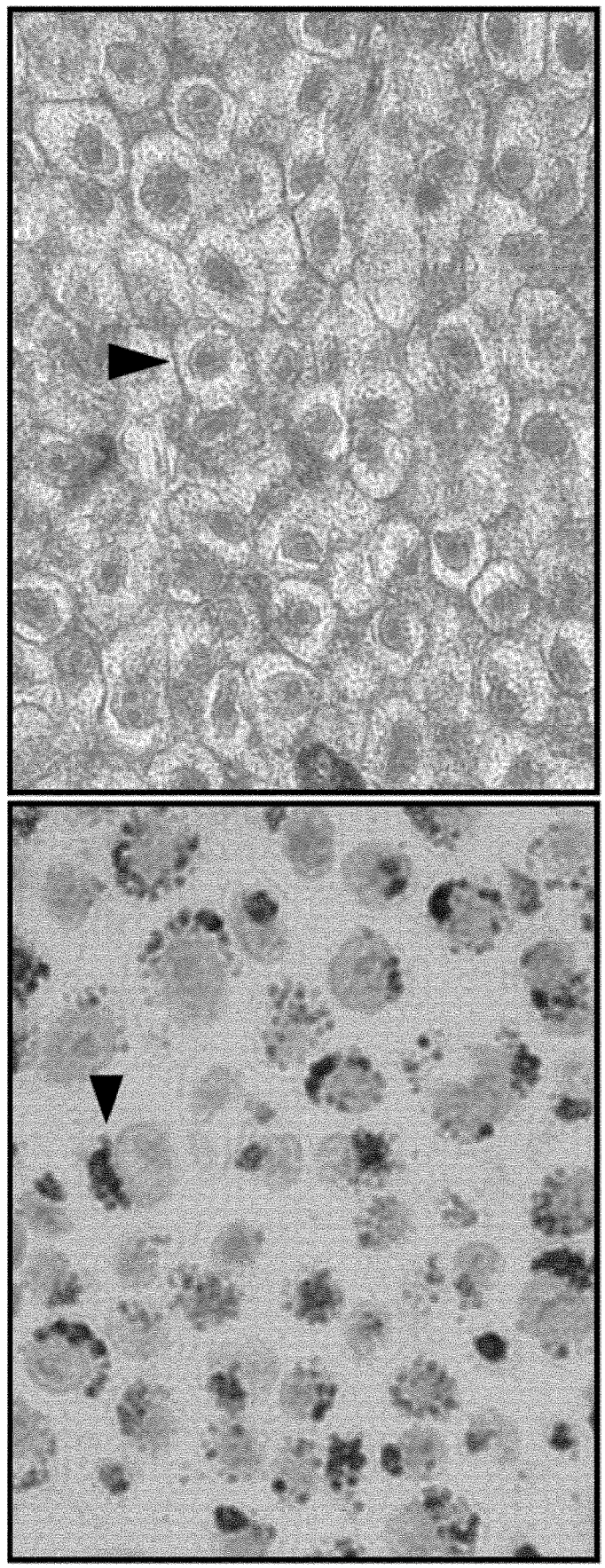

FIG. 19 Immunohistochemistry: Melanoma stained with M06 and mG2-2 followed by secondary staining with an anti-mouse antibody and examination under a microscope at 40× magnification as described in Example 3.

Figure 20:
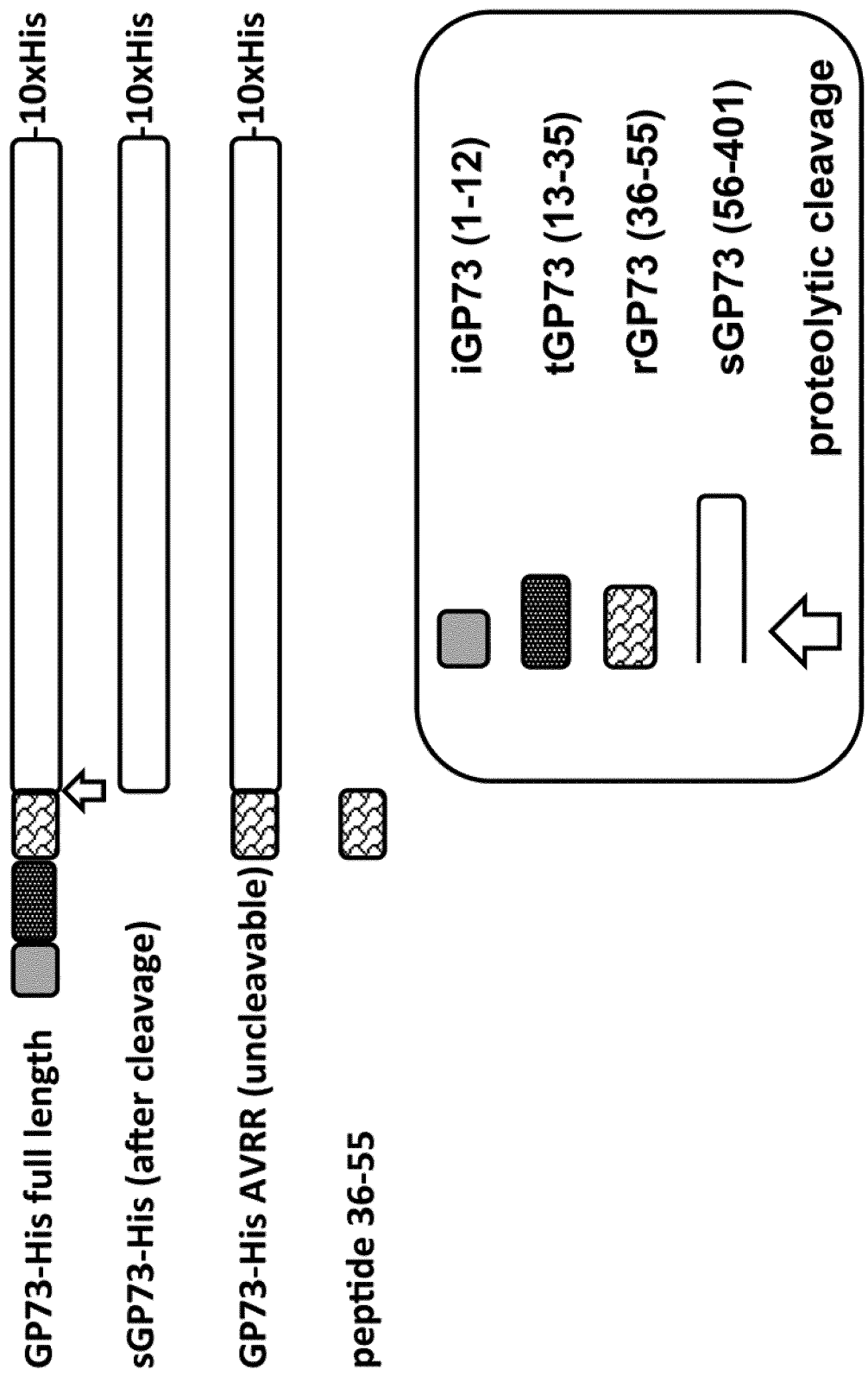

FIG. 20 The scheme depicts the recombinant proteins and the peptide used for the binding assays described in Example 13. Full length GP73 (AA 1-401) with C-terminal 10×His-Tag is secreted as sGP73-His after proteolytic cleavage at AA 55. Thus, sGP73-His encompasses AA 56 to 401 with a C-terminal 10×His-Tag. In contrast, GP73 AVRR, a mutated variant (R52A) lacking the intracellular part (iGP73 AA 1-12) and the transmembrane domain (tGP73 AA 13-35) is secreted but not cleaved, therefore it encompasses AA36 to 401 and a C-terminal 10×His-Tag.

Figure 21:
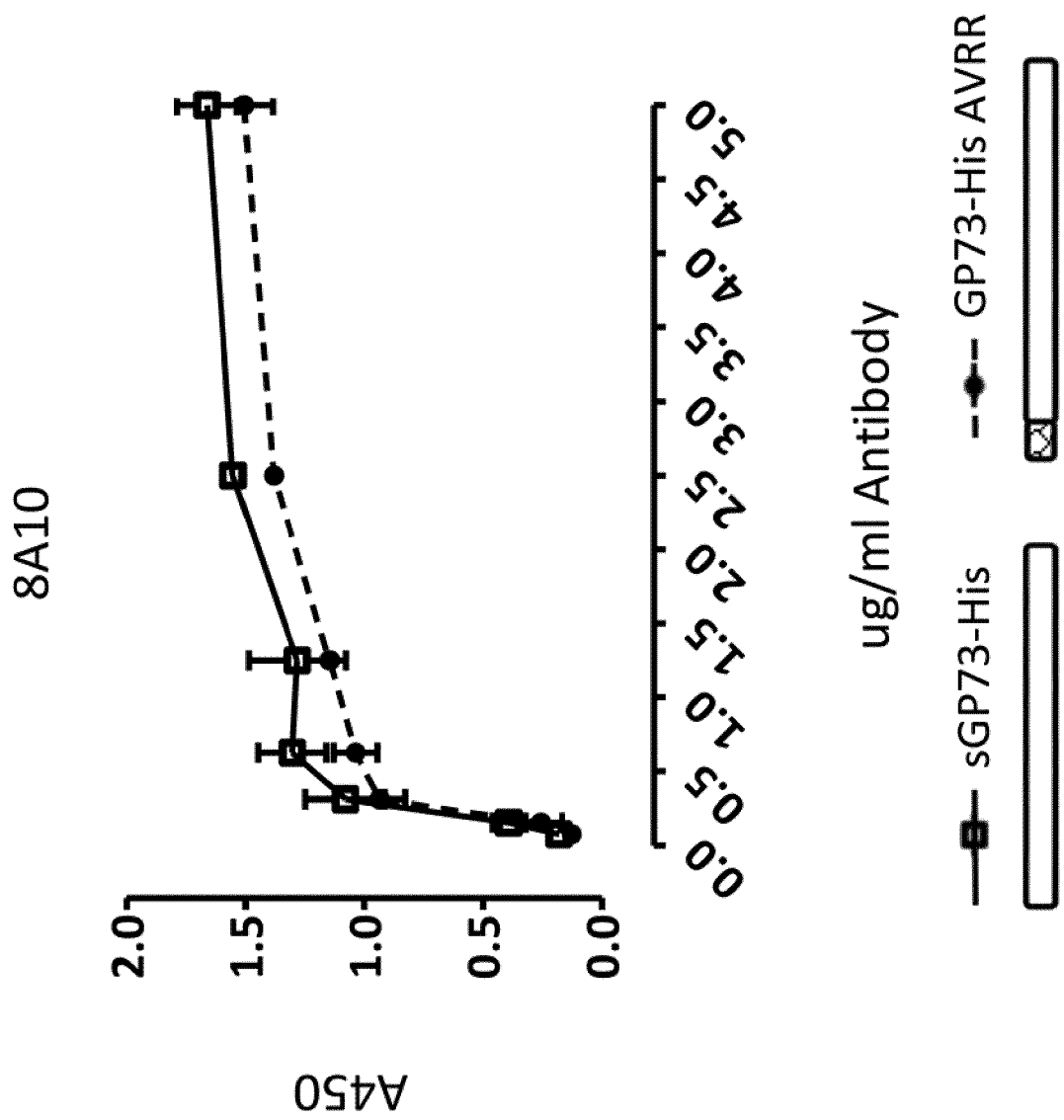

FIG. 21(A-C) Binding curves of an Isotype control antibody (A), 8A10 (IgG2a), a monoclonal murine antibody as described in patent CN105734059A (B) and G2-2opti (IgG2a) (C) on sGP73-HIS versus GP73-His AVRR, only the latter encompasses GP73 including the claimed epitope AA 36 to 55 as described in Example 13.

Figure 22:
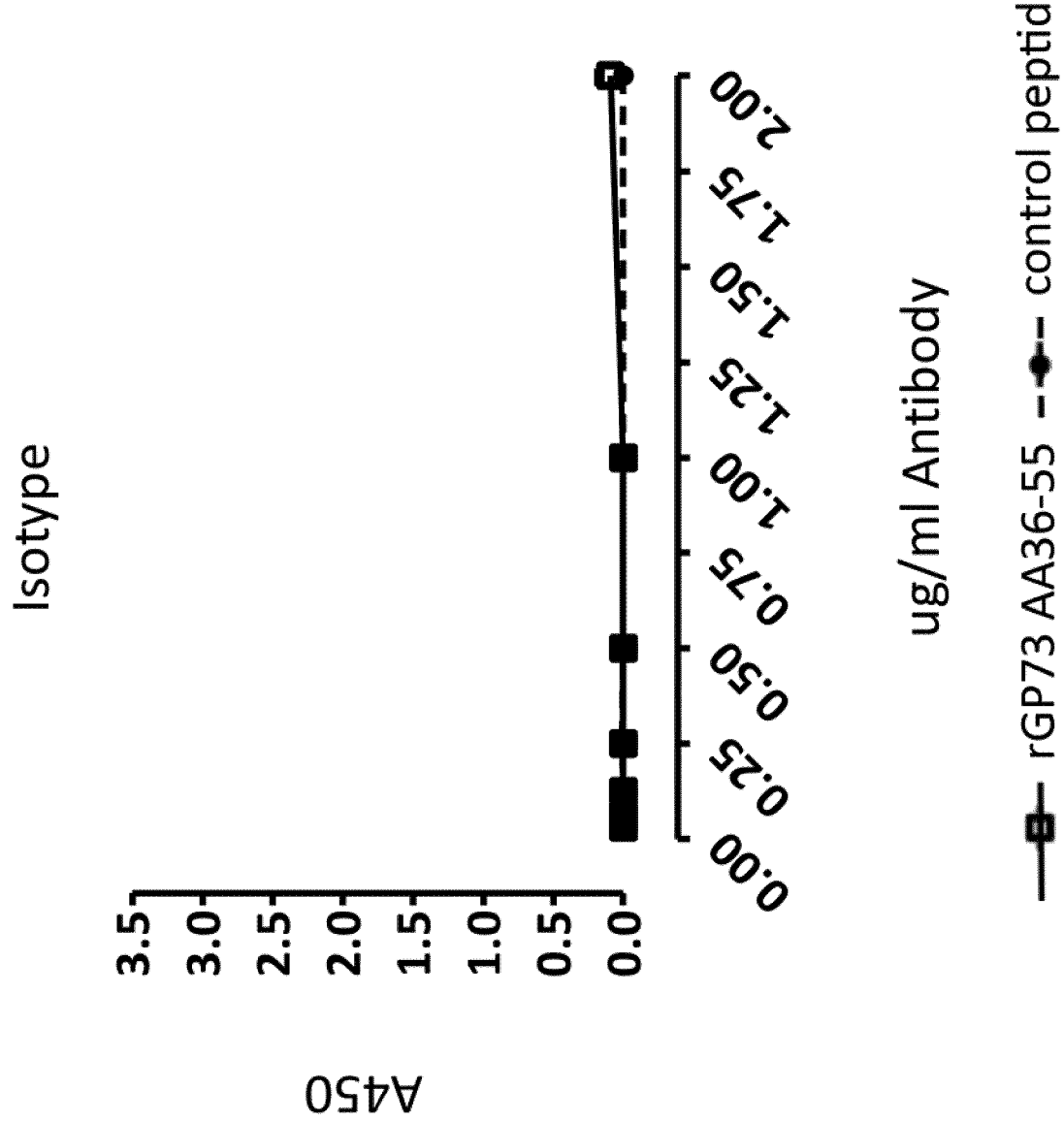
Figure 22:
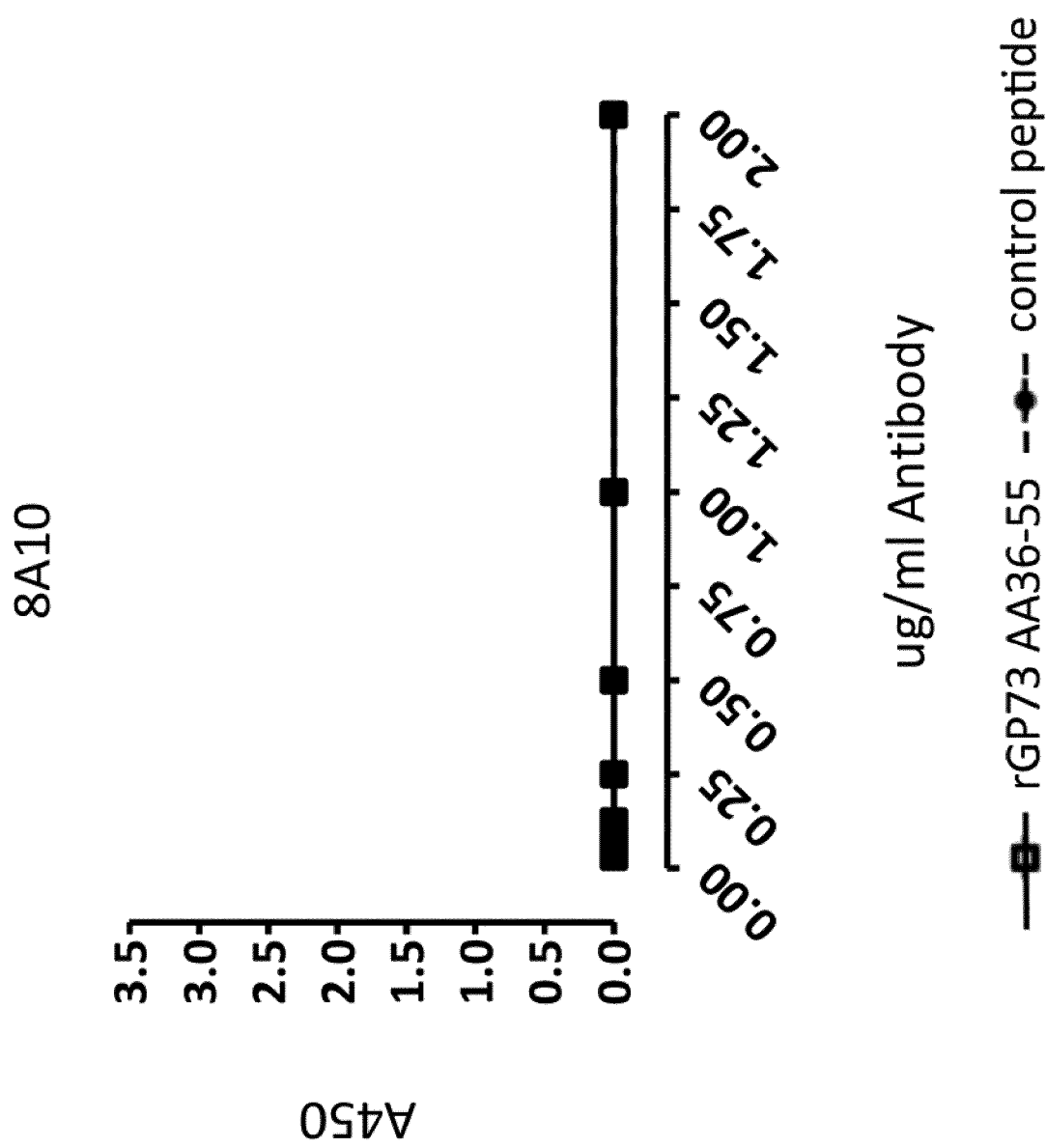
Figure 22:
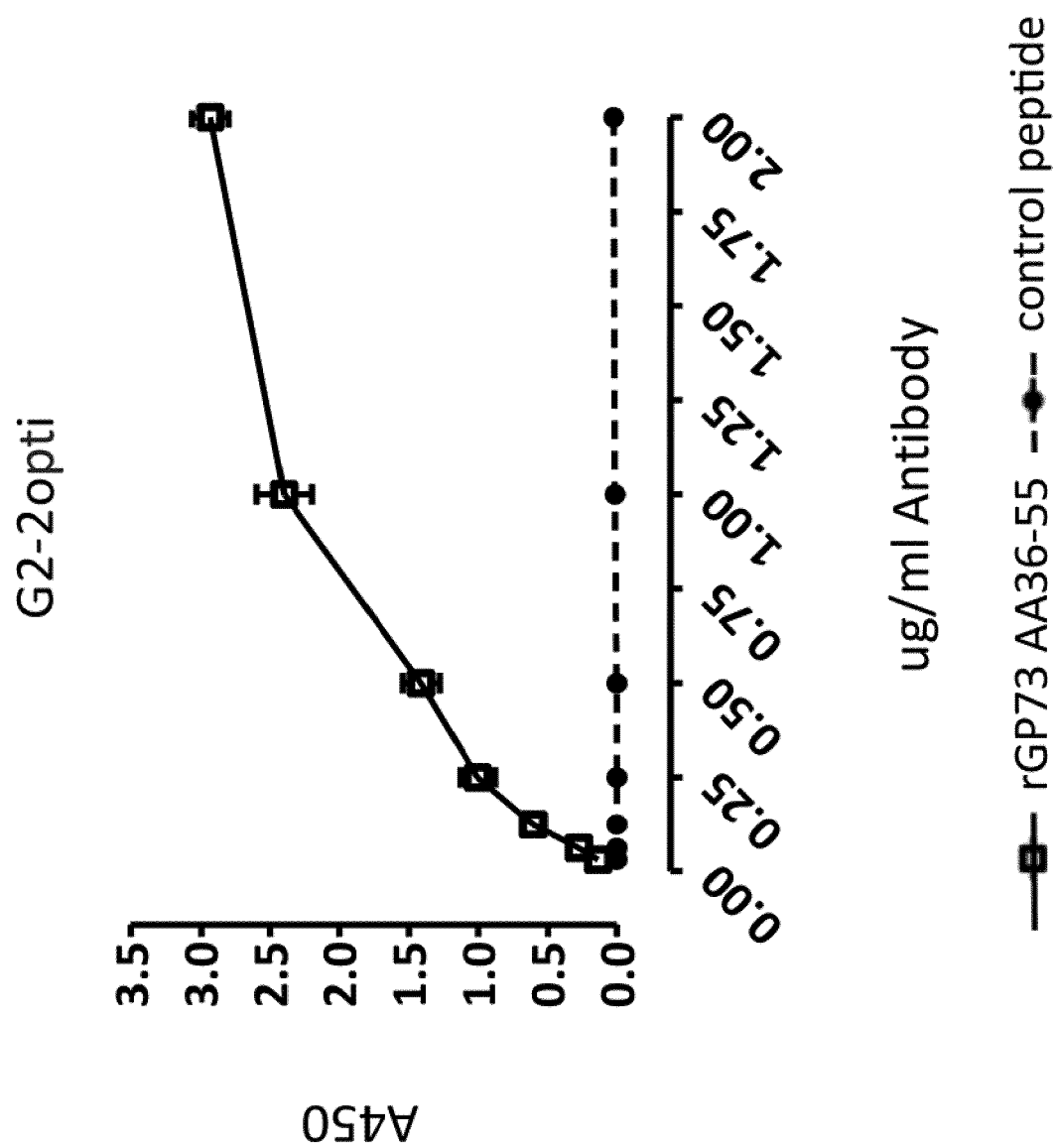

FIG. 22(A-C) Binding curves of Isotype control antibody (A), 8A10 (IgG2a), a monoclonal murine antibody as described in patent CN105734059A (B) and G2-2opti (IgG2a) (C) on peptide rGP73 (GP73 AA 36 to 55), the claimed epitope, versus an unrelated control peptide as described in Example 13.

Figure 23:
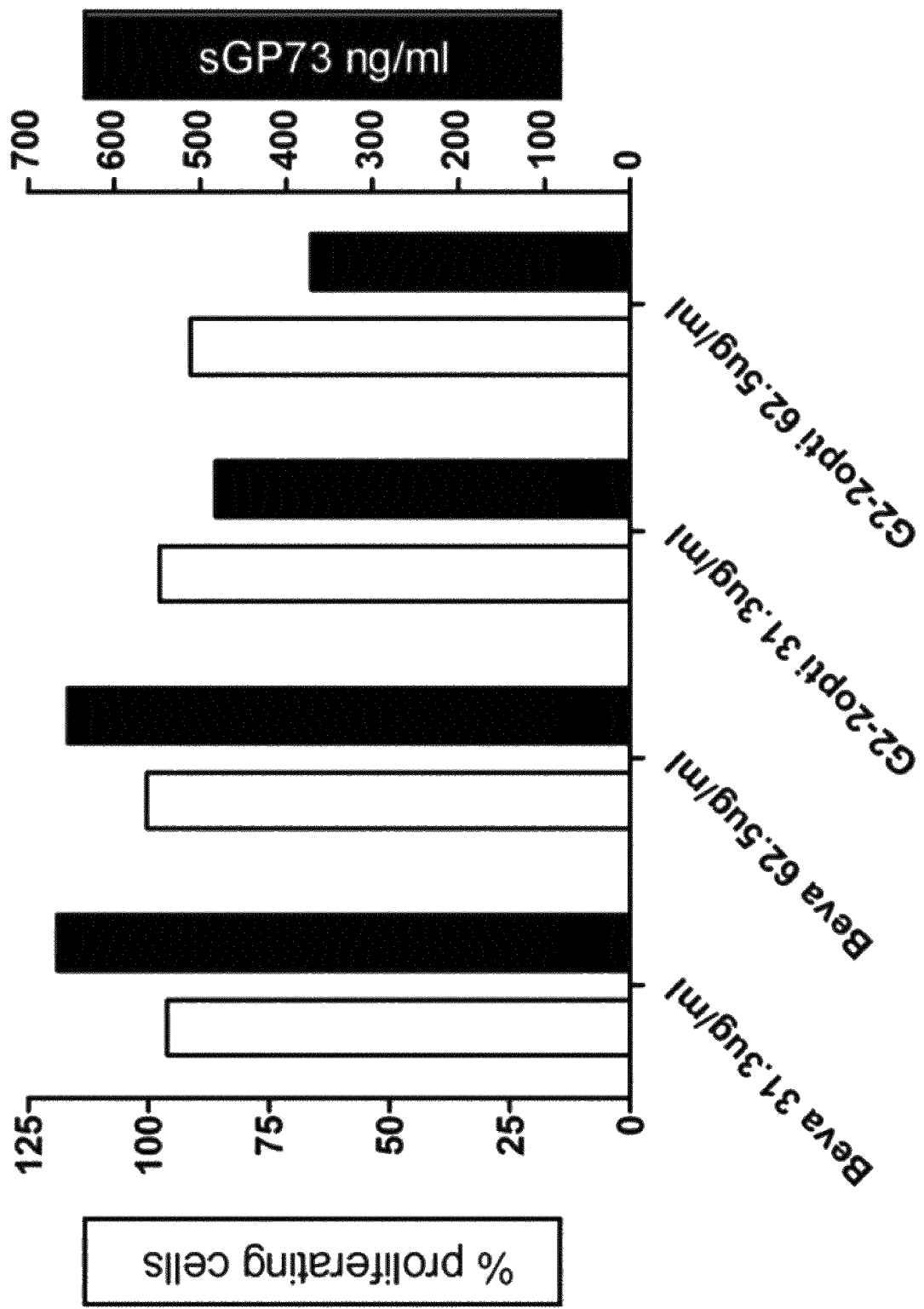

FIG. 23 Measurement of sGP73 in cell culture supernatant after treatment of 293HEK GP73-His full length cells with Bevacizumab or G2-2opti (IgG1). Furin cleavage is a prerequisite for sGP73 to appear in the supernatant. Increasing concentrations of G2-2opti (IgG1) block Furin cleavage and reduce GP73 concentration as described in Example 14.

Figure 24:
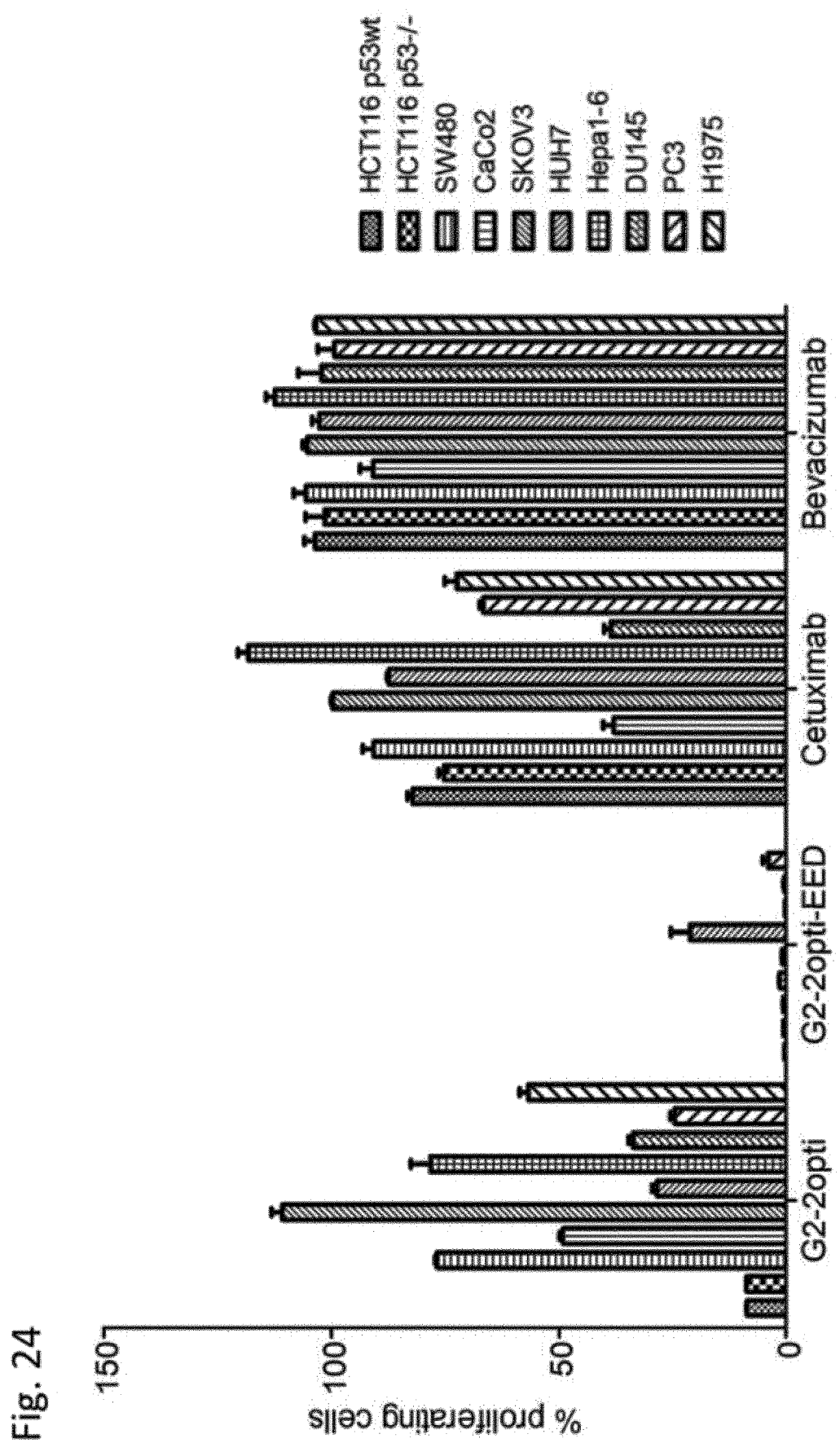

FIG. 24 Cell lines from different human cancers were treated with 1 mg/ml of antibody G2-2opti (IgG1) or G2-2opti-EED (IgG1) or Cetuximab or Bevacizumab for 96 hours. Shown is relative (%) proliferation compared to the proliferation of untreated controls. Tested cancer entities are colorectal cancer (HCT116, SW40 with K-Ras mutation G12V, CaCo2), ovarian cancer (SKOV3), liver cancer (HUH7, Hepa1-6), prostate cancer (DU145, PC3) and lung cancer (H1975 with EGFR mutations T790M, L858R) as described in Example 15.

DETAILED DESCRIPTION

An "antigen binding molecule," as used herein, is any molecule that can specifically or selectively bind to an antigen. A binding molecule may include or be an antibody or a fragment thereof. An anti-GP73 binding molecule is a molecule that binds to the GP73 antigen, such as an anti-GP73 antibody or fragment thereof, at a specific recognition site, epitope as detailed further above. That is, antigen-binding molecules of the invention bind to an epitope within the amino acid sequence of any one of SEQ ID NOs 30, 31 and/or 32. Other anti-GP73 binding molecules may also include multivalent molecules, multi-specific molecules (e.g., diabodies), fusion molecules, aptimers, avimers, or other naturally occurring or recombinantly created molecules. Illustrative antigen-binding molecules useful in the present invention include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), Adnectin (WO 2002/032925) and fynomers (WO 2013/135588).

The terms "anti-GP73 antibody" and "an antibody that binds to GP73" or simply "antibody" as used herein refer to an antibody that is capable of binding GP73 with sufficient affinity such that the antibody is useful as a diagnostic and/or therapeutic agent in targeting GP73. In one embodiment, the extent of binding of an anti-GP73 antibody to an unrelated, non-GP73 protein is less than about 10% of the binding of the antibody to GP73 as measured, e.g., by a radioimmunoassay (RIA). In certain embodiments, an antibody that binds to GP73 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-GP73 antibody binds to an epitope of GP73 that is conserved among GP73 from different species. As detailed further above, the antibody of the invention binds to a defined epitope within the GP73 extracellular part. In particular, the antibody of the invention binds to an epitope within the amino acid sequence of SEQ ID NO: 30, 31 and/or 32. In general, the term "antibody" is used herein in the broadest sense and encompasses various antibody structures, including but not limited to monoclonal antibodies, polyclonal antibodies, multispecific antibodies (e.g., bispecific antibodies), fully-human antibodies and antibody fragments so long as they exhibit the desired antigen-binding activity. Antibodies within the present invention may also be chimeric antibodies, recombinant antibodies, antigen-binding fragments of recombinant antibodies, humanized antibodies or antibodies displayed upon the surface of a phage or displayed upon the surface of a chimeric antigen receptor (CAR) T cell.

An "antigen-binding fragment" of an antibody refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to an epitope" within a defined region of a protein is an antibody that requires the presence of one or more of the amino acids within that region for binding to the protein.

In certain embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 20% of the binding to unaltered protein. In some embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. In certain embodiments, binding of the antibody is determined by FACS, WB or by a suitable binding assay such as ELISA.

The antibody or antigen-binding fragment thereof as provided in the context of the present invention is not particularly limited as long as it is an "anti-GP73 antibody or an antigen-binding fragment thereof" as defined above. Thus, the antibody may be any antibody which specifically binds to/specifically recognizes/interacts with an epitope within the amino acid sequences of SEQ ID NO: 30, 31 and/or 32. Accordingly, the invention also provides antibodies binding to the same epitope as any of the specific antibodies provided herein.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of GP73. Said binding/interaction is also understood to define a "specific recognition". The term "specifically recognizing" means in accordance with this invention that the antibody is capable of specifically interacting with and/or binding to at least two amino acids of GP73 as defined herein, in particular interacting with/binding to at least two amino acids within the amino acid sequences of SEQ ID NOs: 30, 31 and/or 32.

The term "specific interaction" as used in accordance with the present invention means that the antibody or antigen-binding fragment thereof of the invention does not or does not essentially cross-react with (poly) peptides of similar structures. Accordingly, the antibody or antigen-binding fragment thereof of the invention specifically binds to/interacts with structures of GP73 formed by particular amino acid sequences within the amino acid sequences of SEQ ID NOs: 30, 31 and/or 32. Specific examples of such molecules are provided herein.

Cross-reactivity of antigen-binding molecules, in particular a panel of antibodies or antigen-binding fragments thereof under investigation may be tested, for example, by assessing binding of said panel of antibodies or antigen-binding fragments thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, antigen-binding fragments thereof and the like) that bind to the certain structure of GP73 as defined herein, e.g., a specific epitope or (poly) peptide/protein of GP73 as defined herein but do not or do not essentially bind to any of the other epitope or (poly) peptides of the same GP73, are considered specific for the epitope or (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIAcoreO), analytical ultracentrifugation, isothermal titration calorimetry, fluorescence anisotropy, fluorescence spectroscopy or by radiolabeled ligand binding assays.

Accordingly, specificity can be determined experimentally by methods known in the art and methods as described herein. Such methods comprise, but are not limited to Western Blots, ELISA-, RIA-, ECL-, IRMA-tests and peptide scans.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies", refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant (human) antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "heterohybrid antibody" refers to an antibody having light and heavy chains of different organismal origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: JonesNature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins.

"Single-chain Fv" or "scFv" antibody fragments have, in the context of the invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Pluckthun in The Pharmacology of Monoclonal Antibodies, Rosenburg and Moore eds. Springer-Verlag, N.Y. (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the antibody molecule described herein above is selected from the group consisting of a full antibody (immunoglobulin, like an IgG1, an IgG2, an IgG2a, an IgG2b, an IgA1, an IgGA2, an IgG3, an IgG4, an IgA, an IgM, an IgD or an IgE), F(ab)-, Fab'-SH—, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art, see e.g. (LoBuglio, Proceedings of the American Society of Clinical Oncology Abstract (1997), 1562 and Khor, Proceedings of the American Society of Clinical Oncology Abstract (1997), 847).

Accordingly, in the context of this invention, antibody molecules or antigen-binding fragments thereof are provided, which are humanized and can successfully be employed in pharmaceutical compositions.

The specificity of the antibody or antigen-binding fragment of the present invention may not only be expressed by the nature of the amino acid sequence of the antibody or the antigen-binding fragment as defined above but also by the epitope to which the antibody is capable of binding to. Thus, the present invention relates, in one embodiment, to an anti-GP73 antibody or an antigen-binding fragment thereof which recognizes the same epitope as an antibody of the invention, preferably antibody G2-2opti. As shown in the Examples section, the epitope is a linear epitope located within the amino acid sequences of SEQ ID NOs: 30, 31 and/or 31, i.e. SSRSVDLQTRIMELEGRVRR (SEQ ID NO: 30), SSRSVELQTRIVELEGRVRR (SEQ ID NO: 31) and/or SSRSVDLQTRIVELEGRVRR SEQ ID NO: 32, of GP73 as defined by SEQ ID N0:1. In a preferred embodiment, the epitope bound by the antibodies of the invention is within the amino acid sequence RIMELEGRVRR of SEQ ID NO: 30, more preferably within the amino acid sequence EGRVRR.

It may be understood by a person skilled in the art that the epitopes may be comprised in the GP73 protein, but may also be comprised in a degradation product thereof or may be a chemically synthesized peptide. The amino acid positions are only indicated to demonstrate the position of the corresponding amino acid sequence in the sequence of the GP73 protein. The invention encompasses all peptides comprising the epitope. The peptide may be a part of a polypeptide of more than 100 amino acids in length or may be a small peptide of less than 100, preferably less than 50, more preferably less than 25 amino acids, even more preferably less than 16 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophore), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane.

In order to test whether an antibody in question and the antibody of the present invention recognize the same epitope, the following competition study may be carried out: Vero cells infected with 3 moi (multiplicity of infection) are incubated after 20 h with varying concentrations of the antibody in question as the competitor for 1 hour. In a second incubation step, the antibody of the present invention is applied in a constant concentration of 100 nM and its binding is flow-cytometrically detected using a fluorescence-labelled antibody directed against the constant domains of the antibody of the invention. Binding that conducts anti-proportional to the concentration of the antibody in question is indicative for that both antibodies recognize the same epitope. However, many other assays are known in the art which may be used.

The present invention also relates to the production of specific antibodies against native polypeptides and recombinant polypeptides of GP73. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of GP73 can be subcloned into an appropriated vector, wherein the recombinant polypeptide is to be expressed in an organism being able for an expression, for example in bacteria. Thus, the expressed recombinant protein can be intra-peritoneally injected into a mice and the resulting specific antibody can be, for example, obtained from the mice serum being provided by intra-cardiac blood puncture. The present invention also envisages the production of specific antibodies against native polypeptides and recombinant polypeptides by using a DNA vaccine strategy as exemplified in the appended examples. DNA vaccine strategies are well-known in the art and encompass liposome-mediated delivery, by gene gun or jet injection and intramuscular or intradermal injection. Thus, antibodies directed against a polypeptide or a protein or an epitope of GP73, in particular the epitope of the antibodies provided herein, can be obtained by directly immunizing the animal by directly injecting intramuscularly the vector expressing the desired polypeptide or a protein or an epitope of GP73, in particular the epitope of the antibodies of the invention, which lies within the amino acid sequences of SEQ ID NOs: 30, 31 and/or 32. The amount of obtained specific antibody can be quantified using an ELISA, which is also described herein below. Further methods for the production of antibodies are well known in the art, see, e.g. Harlow and Lane, "Antibodies, A Laboratory Manual", CSH Press, Cold Spring Harbor, 1988.

Thus, under designated assay conditions, the specified antibodies and the corresponding epitope of GP73 bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Shepherd and Dean (2000), Monoclonal Antibodies: A Practical Approach, Oxford University Press and/or Howard and Bethell (2000) Basic Methods in Antibody Production and Characterization, Crc. Pr. Inc. for a description of immunoassay formats and conditions that can be used to determine specific immunoreactivity. Typically a specific or selective reaction will be at least twice background signal to noise and more typically more than 10 to 100 times greater than background. The person skilled in the art is in a position to provide for and generate specific binding molecules directed against the novel polypeptides. For specific binding-assays it can be readily employed to avoid undesired cross-reactivity, for example polyclonal antibodies can easily be purified and selected by known methods (see Shepherd and Dean, loc. cit.).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "endosomal escape domain" (EED) as used herein refers to a peptide that disrupts the endosomal cycling process in a cell, releases endosomal content in the cytoplasm and thereby inhibits or prevents a cellular function and/or causes cell death or destruction. EED include, but are not limited to, dengue virus and other virus derived EED and variants thereof, bacterial derived EED and peptides containing two aromatic indole rings or one indole ring and two aromatic phenyl groups (WO 2016/015621; WO 2016/037985; Kiesgen et al., Protein Eng Des Sel. 27(10):331-7 (2014) and Lohn et al., Sci Rep. 6:32301 (2016).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non human primates such as macaques), rabbits, and rodents (e.g., mice and rats). In certain embodiments, the individual or subject is a human.

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extra chromosomally or at a chromosomal location that is different from its natural chromosomal location.

"Isolated nucleic acid encoding an anti-GP73 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "GP73," as used herein, refers to any native GP73. The term includes GP73 from any vertebrate source, including mammals such as primates (e.g. humans and rhesus macaques) and rodents (e.g., mice and rats), unless otherwise indicated. The term also includes naturally occurring variants of GP73, e.g., splice variants or allelic variants. The amino acid sequence of an exemplary human GP73 protein is shown in SEQ ID NO: 1. The amino acid sequence of nonlimiting exemplary mouse GP73 protein is shown in SEQ ID NO: 29.

The term "GP73-positive cancer" refers to a cancer comprising cells that express GP73 on their surface. In some embodiments, expression of GP73 on the cell surface is determined, for example, using antibodies to GP73 in a method such as immunohistochemistry, FACS, etc. Alternatively, GP73 mRNA expression is considered to correlate to GP73 expression on the cell surface and can be determined by a method selected from in situ hybridization and RT-PCR (including quantitative RT-PCR).

The terms "cancer" and "cancerous" refer to or describe the physiological condition in mammals that is typically characterized by unregulated cell growth/proliferation. Examples of cancer include, but are not limited to, carcinoma, liver cancer, hepatocellular cancer, gastric cancer, lung cancer, esophageal cancer, breast cancer, prostate cancer, lymphoma (e.g., Hodgkin's and non-Hodgkin's lymphoma), blastoma, sarcoma, and leukemia.

The term "GP73-positive cell" refers to a cell that expresses full length or partial GP73 on its surface.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Monovalent Groups

As used herein, the term "alkyl" refers to a monovalent saturated hydrocarbon group which may be linear, branched or cyclic. Preferably the term "alkyl" refers to a monovalent saturated hydrocarbon group which may be linear or branched and is not cyclic. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl).

Unless otherwise indicated, "alkyl" is a monovalent saturated hydrocarbon group which may be linear, branched or cyclic and contains from 1 to 18 carbon atoms, i.e. 1, 2, 3, 4, 5, 6, 7, 8, 9, 10, 11, 12, 13, 14, 15, 16, 17 or 18 carbon atoms, i.e. "$C_1$-$C_{18}$ alkyl".

Examples thereof are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl ($CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl ($CH(CH_3)CH_2CH(CH_3)_2$), 3-methyl-3-pentyl (—$C(CH_3)(CH_2CH_3)_2$), 2-methyl-3-pentyl ($CH(CH_2CH_3)CH(CH_3)_2$), 2,3-dimethyl-2-butyl (—$C(CH_3)_2CH(CH_3)_2$) and 3,3-dimethyl-2-butyl ($CH(CH_3)C(CH_3)_3$).

A preferred example of an "alkyl" is a "$C_1$-$C_{12}$ alkyl" which refers to a monovalent saturated hydrocarbon group which may be linear, branched or cyclic and contains from 1 to 12 carbon atoms, i.e. 1, 2, 3, 4, 5, 6, 7, 8, 9, 10, 11 or 12 carbon atoms. A more preferred example of an "alkyl" is a "$C_1$-$C_8$ alkyl" which refers to a monovalent saturated hydrocarbon group which may be linear, branched or cyclic and contains from 1 to 8 carbon atoms, i.e. 1, 2, 3, 4, 5, 6, 7 or 8 carbon atoms.

Representative "$C_1$-$C_8$ alkyl" groups include, but are not limited to, -methyl, -ethyl, -n-propyl, -n-butyl, -n-pentyl, -n-hexyl, -n-heptyl and -n-octyl.

Branched "$C_1$-$C_8$ alkyl" includes, but is not limited to, -isopropyl, -sec-butyl, -isobutyl, -tert-butyl, -isopentyl, 2-methylbutyl.

An even more preferred example of an "alkyl" is a "$C_1$-$C_6$ alkyl" which refers to a monovalent saturated hydrocarbon group which may be linear, branched or cyclic and contains from 1 to 5 carbon atoms, i.e. 1, 2, 3, 4, 5 or 6 carbon atoms.

Representative "$C_1$-$C_6$ alkyl" groups include, but are not limited to, -methyl, -ethyl, -n-propyl, -n-butyl, -n-pentyl, and -n-hexyl.

Branched "$C_1$-$C_6$ alkyl" includes, but is not limited to, -isopropyl, -sec-butyl, -isobutyl, -tert-butyl, -isopentyl, and 2-methylbutyl;

The term "$C_1$-$C_4$ alkyl," as used herein refers to a monovalent saturated hydrocarbon group which may be linear, branched or cyclic and contains from 1 to 4 carbon atoms, i.e. 1, 2, 3 or 4 carbon atoms.

Representative "$C_1$-$C_4$ alkyl" groups include, but are not limited to, -methyl, -ethyl, -n-propyl, -n-butyl. Branched "$C_1$-$C_4$ alkyl" includes, but is not limited to, -isopropyl, -sec-butyl, -isobutyl, -tert-butyl;

As used herein, the term "alkenyl" refers to a monovalent unsaturated hydrocarbon group which may be linear, branched or cyclic and comprises one or more (e.g., one or two) carbon-to-carbon double bonds while it does not comprise any carbon-to-carbon triple bond.

Unless otherwise indicated, "alkenyl" is a $C_2$-$C_{18}$ monovalent unsaturated hydrocarbon group, containing from 2 to 18 carbon atoms, i.e. 2, 3, 4, 5, 6, 7, 8, 9, 10, 11, 12, 13, 14, 15, 16, 17 or 18 carbon atoms, which may be linear, branched or cyclic and comprises one or more (e.g., one or two) carbon-to-carbon double bonds while it does not comprise any carbon-to-carbon triple bond.

A preferred example of "alkenyl" is a "$C_2$-$C_8$ alkenyl" which denotes an alkenyl group having 2 to 8 carbon atoms, i.e. 2, 3, 4, 5, 6, 7 or 8 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Further examples include, but are not limited to ethylene or vinyl (—CH=$CH_2$), allyl (—$CH_2$CH=$CH_2$), -1-butenyl, -2-butenyl, -isobutylenyl, -1-pentenyl, -2-pentenyl, -3-methyl-1-butenyl, -2-methyl-2-butenyl, cyclopentenyl (—$C_5H_7$), 1-hexenyl, 2-hexenyl, 3-hexenyl, 5-hexenyl (—$CH_2CH_2CH_2CH_2$CH=$CH_2$) and -2,3-dimethyl-2-butenyl.

Examples of $C_2$-$C_6$ alkenyl include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexenyl, 2-hexenyl, and 3-hexenyl.

A more preferred example of "alkenyl" is a "$C_2$-$C_4$ alkenyl" which denotes an alkenyl group having 2 to 4 carbon atoms. Examples therefore are -vinyl, -allyl, -1-butenyl, -2-butenyl, and -isobutylenyl.

As used herein, the term "alkynyl" refers to a monovalent unsaturated hydrocarbon group which may be linear, branched or cyclic and comprises one or more (e.g., one or two) carbon-to-carbon triple bonds and optionally one or more carbon-to-carbon double bonds.

Unless defined otherwise, the term "alkynyl" refers to "$C_{2-8}$ alkynyl" which denotes an alkynyl group having 2 to 8 carbon atoms. Preferred exemplary alkynyl groups are acetylenyl, propynyl, 1-butynyl, 2-butynyl, 1-pentynyl, 2-pentynyl, cyclopentenyl, 3-methyl-1-butynyl, 5-hexenyl, vinyl, ethylene.

Preferred alkynyl groups are "$C_{2-6}$ alkynyl" which denotes an alkynyl group having 2 to 6 carbon atoms and "$C_{2-4}$ alkynyl" which denotes an alkynyl group having 2 to 4 carbon atoms.

The term "alkoxy" refers to a group represented by "—O-alkyl", wherein "alkyl" is as defined above, including the preferred examples of Alkyl.

Exemplary alkoxy groups include, but are not limited to, methoxy (—$OCH_3$) and ethoxy (—$OCH_2CH_3$).

A preferred example of "alkoxy" is a "$C_1$-$C_5$ alkoxy" which is an alkoxy group with 1 to 5 carbon atoms, and can be described as "—O—$C_1$-$C_5$ Alkyl".

As used herein, the term "carbocyclyl" refers to a ring group, including monocyclic rings as well as bridged ring, spiro ring and/or fused ring systems (which may be composed, e.g., of two or three rings), wherein one or more carbon ring atoms may optionally be oxidized (i.e., to form an oxo group), and further wherein said ring group may be saturated, partially unsaturated (i.e., unsaturated but not aromatic) or aromatic. Preferred examples of the "carbocyclyl" group correspond to the definition of the "carbocycle" given below wherein one hydrogen atom is abstracted.

The term "carbocycle" preferably refers to a saturated or unsaturated monocycle having 3 to 7 carbon atoms or a bicycle having 7 to 12 carbon atoms. Monocyclic carbocycles have preferably 3 to 6 ring atoms, more preferably 5 or 6 ring atoms and include phenyl as defined below. Bicyclic carbocycles typically have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocyclo" refers to a $C_3$-$C_8$ carbocycle group defined above wherein one of the carbocycle groups' hydrogen atoms is replaced with a bond.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), anthracenyl, or phenanthrenyl.

Unless defined otherwise, the term "aryl" refers to "$C_5$-$C_{20}$ aryl" which is an aryl group with 5 to 20 carbon atoms in the carbocyclic aromatic rings.

A more preferred example of an aryl group is a "$C_5$-$C_{14}$ aryl" which is an aryl group with 5 to 14 carbon atoms in the carbocyclic aromatic rings.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S, P and N, and the remaining ring atoms are carbon atoms, wherein one or more P ring atoms (if present) and/or S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. Unless defined otherwise, "heterocyclyl" preferably refers to heteroaryl.

A preferred example of "heterocyclyl" is "$C_3$-$C_8$ heterocyclyl" which refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

Exemplary heterocycles are described, e.g., in Paquette, Leo A., "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, ß-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrirnidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S, P and N, and the remaining ring atoms are carbon atoms, wherein one or more S ring atoms (if present) and/or one or more P ring atoms (if present) and/or one or more N ring atoms (if present) may optionally be oxidized, and further wherein one or more carbon ring atoms may optionally be oxidized (i.e., to form an oxo group). "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromenyl, xanthenyl, phenoxathiinyl, pyrrolyl (e.g., 2H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolizinyl, isoindolyl, indolyl (e.g., 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, furazanyl, phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzoxazolyl, benzisoxazolyl, benzimidazolyl, 1H-tetrazolyl, 2H-tetrazolyl, coumarinyl, or chromonyl.

Unless defined otherwise, a "heteroaryl" preferably refers to a 5 to 14 membered (more preferably 5 to 10 membered) monocyclic ring or fused ring system comprising one or more (e.g., one, two, three or four) ring heteroatoms independently selected from O, S, P and N, wherein one or more S ring atoms and/or one or more P ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S, P and N, wherein one or more S ring atoms and/or one or more P ring atoms (if present) and/or one or more N ring atoms (if present) are optionally oxidized, and wherein one or more carbon ring atoms are optionally oxidized.

Preferred heteroaryl groups comprise 3 to 20 carbon atoms and 1 to 3 heteroatoms selected from N, O, P, and S. Other preferred heteroaryl groups may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

The term "arylalkyl" refers to a group represented by "-(alkylene)-(aryl)", "-(alkenylene)-(aryl)" and "-(alkynylene)-(aryl)", wherein "alkylene", "alkenylene" and "alkynylene" are as defined below, and "aryl" is as defined above. The alkylene is preferably a $C_1$-$C_6$ alkylene and is preferably acyclic. The aryl group is preferably a $C_5$-$C_{14}$ aryl group. In other words, the term "arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkyl, alkenyl or alkynyl groups, of the arylalkyl group is 1 to 6 carbon atoms and the aryl moiety is 5 to 14 carbon atoms.

The term "heteroarylalkyl" refers to a group represented by "-(alkylene)-(heteroaryl)", "-(alkenylene)-(heteroaryl)" and "-(alkynylene)-(heteroaryl)", wherein "alkylene", "alkenylene" and "alkynylene" are as defined below, and aryl is as defined above. In other words, "heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Divalent Groups

As used herein the term "alkylene" refers to a divalent group which corresponds to the term "alkyl" wherein one of the hydrogens is removed and typically replaced by a bond. Unless otherwise specified, the term "alkylene" preferably refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethylene (—CH$_2$CH$_2$—), 1,3-propylene (—CH$_2$CH$_2$CH$_2$—) and 1,4-butylene (—CH$_2$CH$_2$CH$_2$CH$_2$—).

A preferred example of an "alkylene" is a "C$_1$-C$_{10}$ alkylene" which is a straight chain, saturated hydrocarbon group of the formula —(CH$_2$)$_{1-10}$—. Examples of a "C$_1$-C$_{10}$ alkylene" include methylene, ethylene, propylene, butylene, pentylene, hexylene, heptylene, ocytylene, nonylene and decalene.

As used herein the term "alkenylene" refers to a divalent group which corresponds to the term "alkenyl" wherein one of the hydrogens is removed and typically replaced by a bond. Unless otherwise specified, the term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Preferred alkenylenes comprise 2 to 12 carbon atoms, 2 to 8 carbon atoms or 2 to 4 carbon atoms. Typical alkenylene radicals include, but are not limited to 1,2-ethylene (—CH═CH—).

As used herein the term "alkynylene" refers to a divalent group which is corresponds to the term "alkynyl" wherein one of the hydrogens is removed and typically replaced by a bond. Unless otherwise specified, the term "alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Preferred alkynylenes comprise 2 to 12 carbon atoms, 2 to 8 carbon atoms or 2 to 4 carbon atoms. Typical alkynylene radicals include, but are not limited to acetylene (—C≡C—), propargyl (—CH$_2$C≡C—), and 4-pentynyl (—CH$_2$CH$_2$CH$_2$C≡C—).

As used herein the term "arylene" refers to a divalent group which is corresponds to the term "aryl" wherein one of the hydrogens is removed any typically replaced by a bond. The valencies may be at any position within the in the aromatic hydrocarbon ring group. As an example, in a phenylene group, the valencies may be in the ortho, meta, or para positions as shown in the following structures:

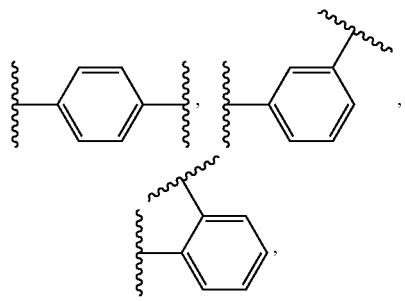

Substituents

Various groups are referred to as being "optionally substituted" or "substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

Substituents of alkyl, aryl, arylalkylene, arylalkyl, alkylene, alkenylene, and alkynylene include, but are not limited to, —X, —R, —OH, —OR, —SR, —SH, —NR$_2$, —NR$_3$, ═NR, —CX$_3$, —CN, —OCN, —SON, —N═C═O, —NCS, —NO, —NO$_2$, ═N$_2$, —N$_3$, NC(═O)R, —C(═O)R, —C(═O)NR$_2$, —SO$_3^-$, —SO$_3$H, —S(═O)$_2$R, —OS(═O)$_2$OR, —S(═O)$_2$NR, —S(═O)R, —OP(═O)(OR)$_2$, —P(═O)(OR)$_2$, —P(OH)$_3$, —PO$_3$H$_2$, —C(═O)R, —C(═O)X, —C(═S)R, —CO$_2$R, —CO$_2^-$, —C(═S)OR, —C(═O)SR, —C(═S)SR, —C(═O)NR$_2$, —C(═S)NR$_2$, —C(═NR)NR$_2$, wherein each X is independently a halogen selected from F, Cl, Br, and I; and each R is independently —H, C$_1$-C$_{18}$ alkyl, C$_6$-C$_{20}$ aryl, C$_3$-C$_{14}$ heterocyclyl, protecting group or prodrug moiety.

Preferred substituents of the alkyl, aryl, arylalkylene, arylalkyl, alkylene, alkenylene, and alkynylene include, but are not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$, —NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —C$_1$-C$_8$ alkyl and aryl.

Unless otherwise defined, substituents include, but are not limited to, $C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$, —NHC(O)R', —SO$_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

It is preferred that the substituent of an alkyl group does not comprise an alkyl group.

A phenyl group which is described as being substituted preferably contains from 1 to 4 of the substituents defined above. A $C_3$-$C_8$ heterocyclyl group which is described as being substituted preferably contains from 1 to 7 of the substituents defined above. A $C_3$-$C_8$ heterocyclo group which is described as being substituted preferably contains from 1 to 6 of the substituents defined above. A $C_3$-$C_{20}$ heterocycle group which is described as being substituted preferably contains from 1 to 7 of the substituents defined above. A $C_3$-$C_8$ carbocycle group which is described as being substituted preferably contains from 1 to 7 of the substituents defined above.

As used herein, the term "halogen" refers to fluoro (—F), chloro (—Cl), bromo (—Br), or iodo (—I).

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

The term "Linker" refers to a chemical moiety comprising a covalent bond or a chain of atoms that covalently attaches an antibody to a drug moiety. Examples of linkers include a divalent radical such as an alkylene, an arylene, a heteroarylene or —(CR$_2$)$_n$O(CR$_2$)$_n$— or repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terns* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethyloxycarbonyl (Fmoc). For a general description of protecting groups and their use, see T. W. Greene, Protective Groups in Organic Synthesis, John Wiley & Sons, New York, 1991, or a later edition.

The scope of the invention embraces all pharmaceutically acceptable salt forms of the compounds disclosed herein which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Preferred pharmaceutically acceptable salts of the compounds disclosed herein include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compounds disclosed herein is a hydrochloride salt. Accordingly, it is preferred that the compounds disclosed herein are in the form of a hydrochloride salt, a hydrobromide salt, a mesylate salt, a sulfate salt, a tartrate salt, a fumarate salt, an acetate salt, a citrate salt, or a phosphate salt, and it is particularly preferred that the compound of formula (I) is in the form of a hydrochloride salt.

Moreover, the scope of the invention embraces the compounds disclosed herein in any solvated form, including, e.g., solvates with water, for example hydrates, or with organic solvents such as, e.g., methanol, ethanol or acetonitrile, i.e., as a methanolate, ethanolate or acetonitrilate, respectively, or in the form of any polymorph. It is to be understood that such solvates of the compounds disclosed herein also include solvates of pharmaceutically acceptable salts of the compounds disclosed herein.

All publications, patent applications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document is authoritative.

In one aspect, the invention is based, in part, on antibodies that bind to GP73 and immunoconjugates comprising such antibodies. Antibodies and immunoconjugates of the invention are useful, e.g., for the diagnosis or treatment of GP73-positive cancers.

Figure 1:
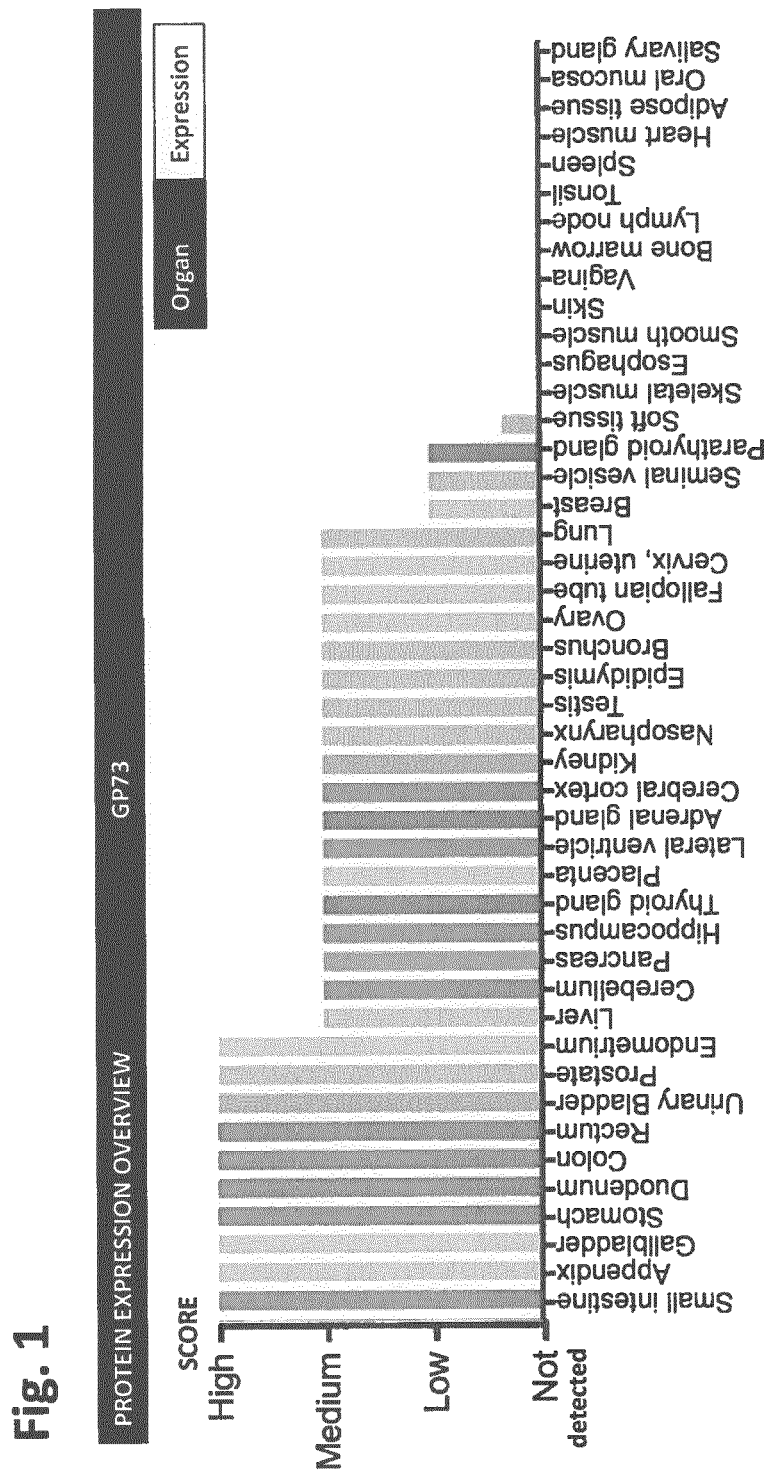
FIG. 1 shows expression of GP73 in normal and diseased and tumor tissues GP73 expression was determined by polyclonal rabbit and polyclonal goat antibodies from Sigma and Santa Cruz.
Figure 3A:
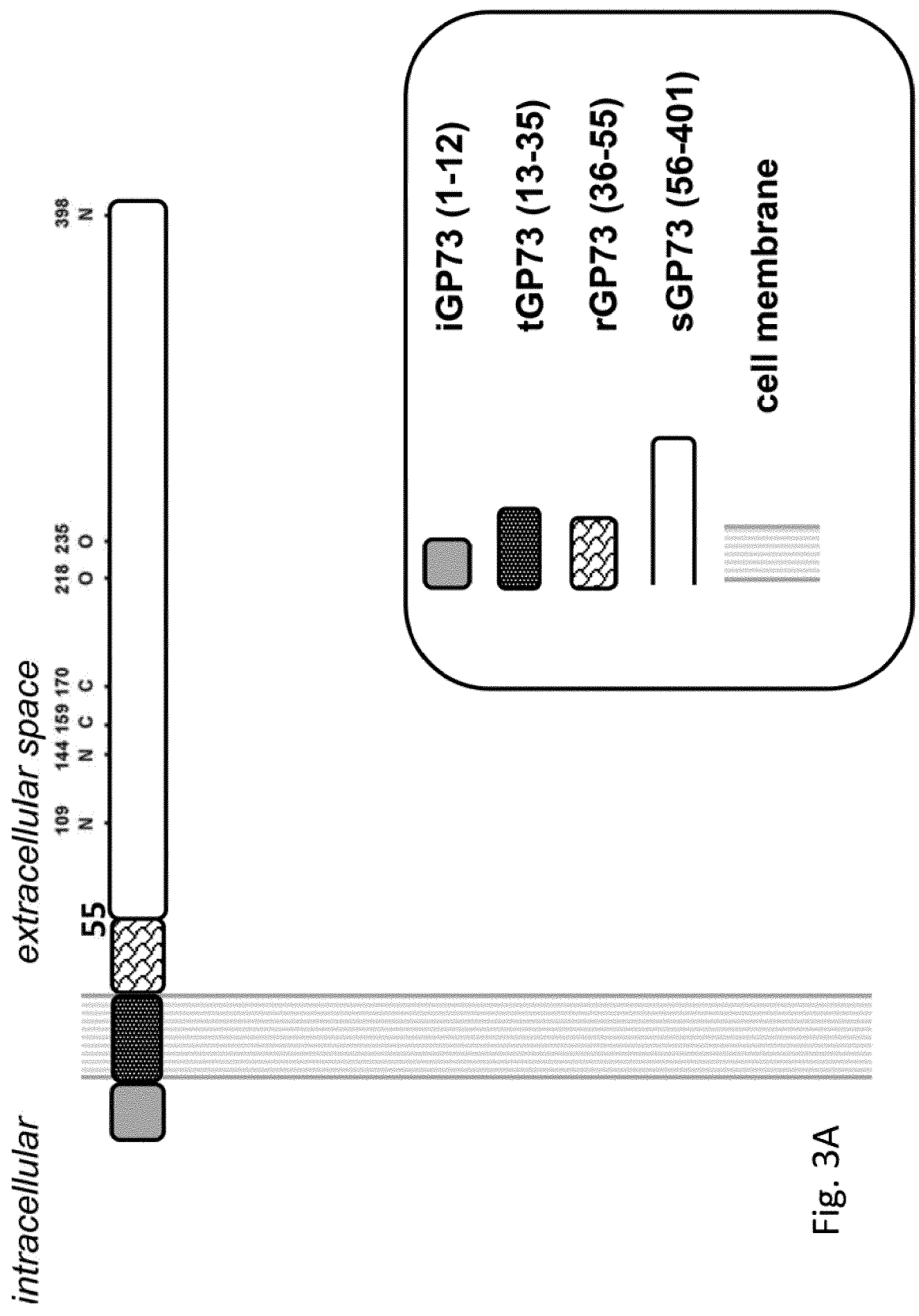
FIG. 3B Scheme of GP73 that is transported by exocytosis from the Golgi apparatus to the cell membrane. Under certain conditions, e.g. inflammation, GP73 is processed by proteolytic cleavage at residue 55 into soluble GP73 (sGP73) and a remnant of GP73, named rGP73, that resides in the extracellular space bound to the cell membrane after cleavage.
FIG. 3C Scheme of GP73 showing the binding site of antibodies G2-2 and G2-1. Through binding of either antibody the proteolytic cleavage site at residue 55 is blocked.
FIG. 3D Scheme of GP73 as therapeutic target. A uncleaved GP73 B cleaved GP73 C After the proteolytic cleavage rGP73 is recovered into the cell by endocytosis. The neo-antigen rGP73 is bound by the specific antibody, e.g. G2-2 D rGP73 and the antibody or ADC are co-transported into the cell by endocytosis. After intracellular translocation of the ADC, the toxin, marked by a star, leads to cell damage and death.
Figure 3B:
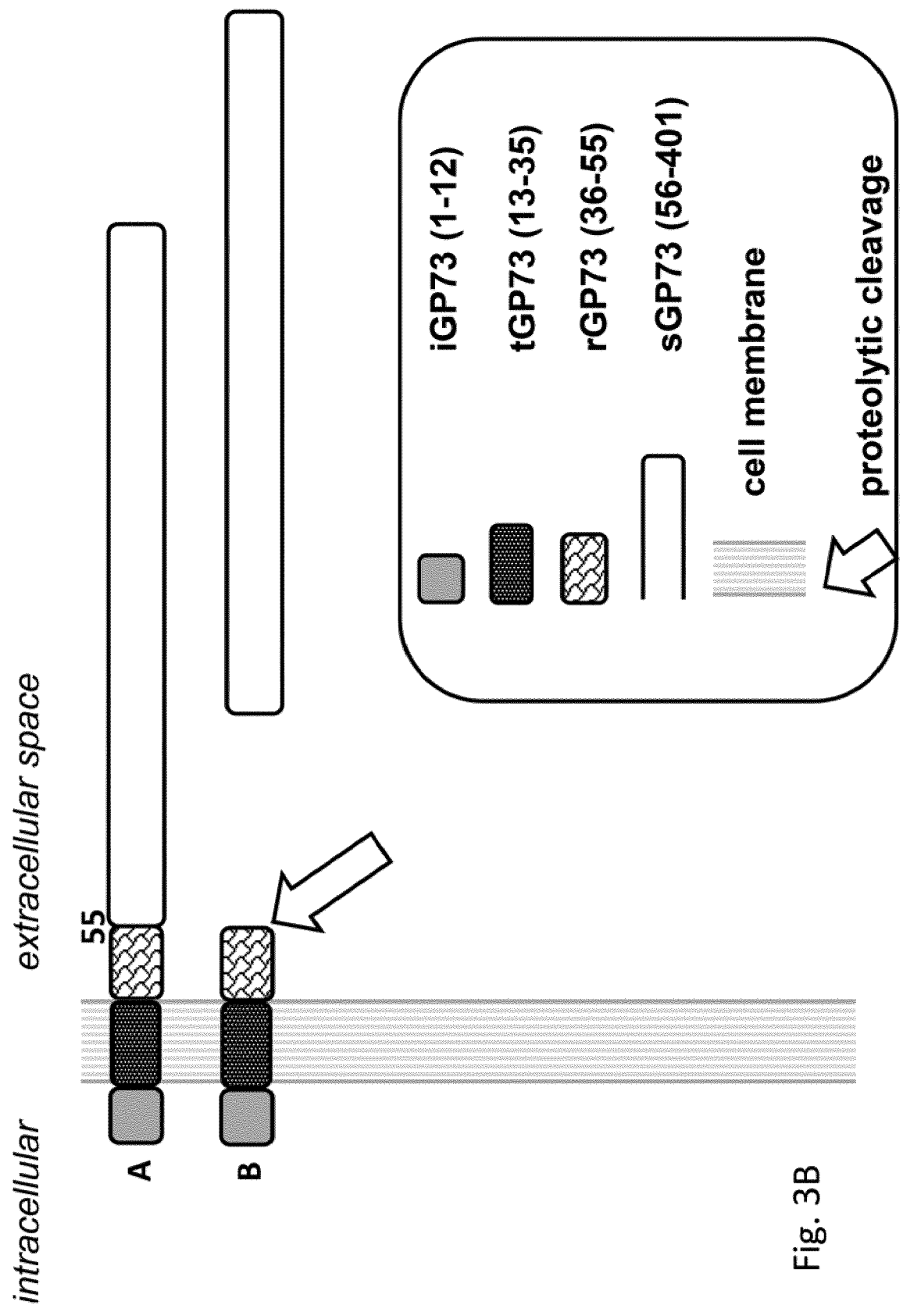
Figure 3C:
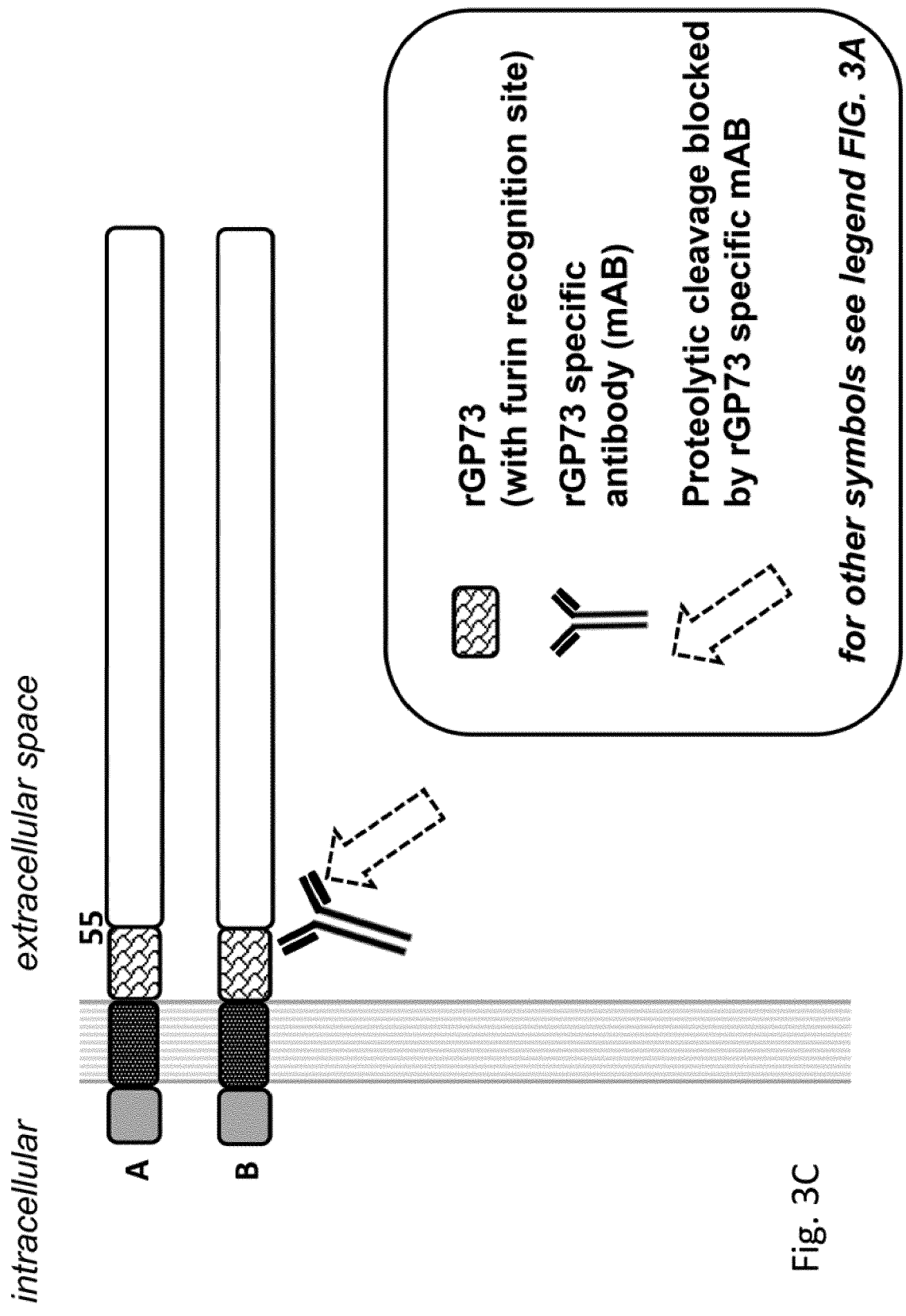
Figure 4:
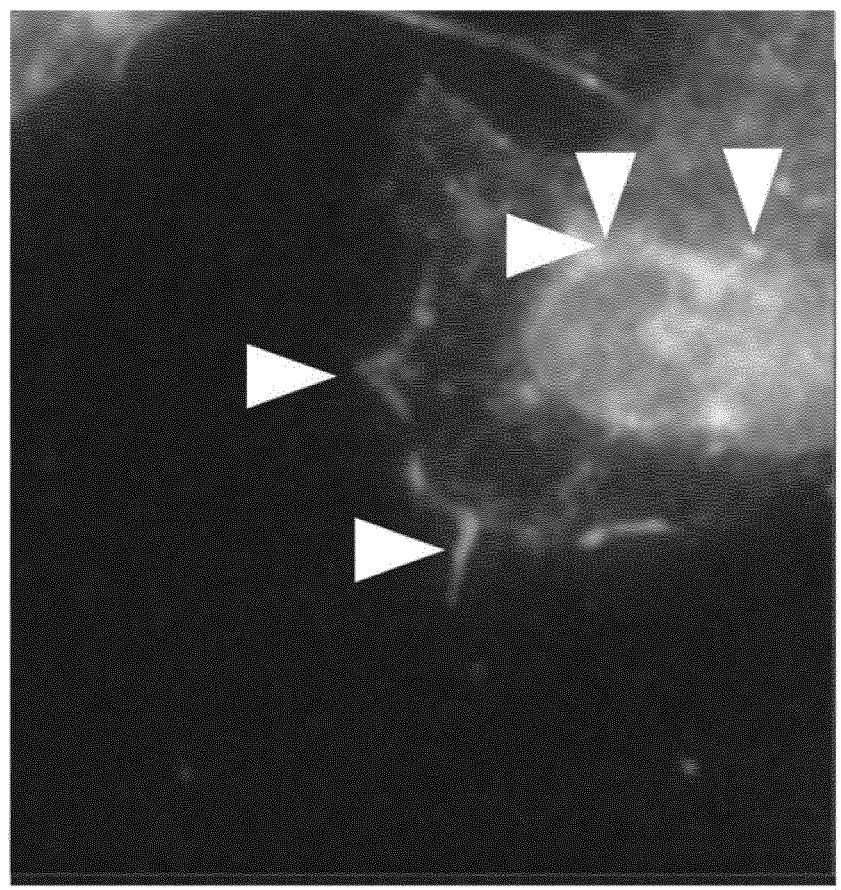
FIG. 4—A depicts a immunofluorescence picture as published in the human protein atlas. The polyclonal rabbit derived antibody from Sigma (HPA010638) binds to GP73 more C-terminal than mG2-2. A typical Golgi staining of these antibodies is shown (left pointing arrows). B shows a double staining using a C-terminal antibody (sc-48010 from Santa Cruz) (left pointing arrows) and mG2-2 (down pointing arrows) on Alexander cells. There is staining overlap at the Golgi apparatus (two tip touching arrows) but exclusive outer membrane staining of mG2-2 (down pointing arrows).
Figure 4:
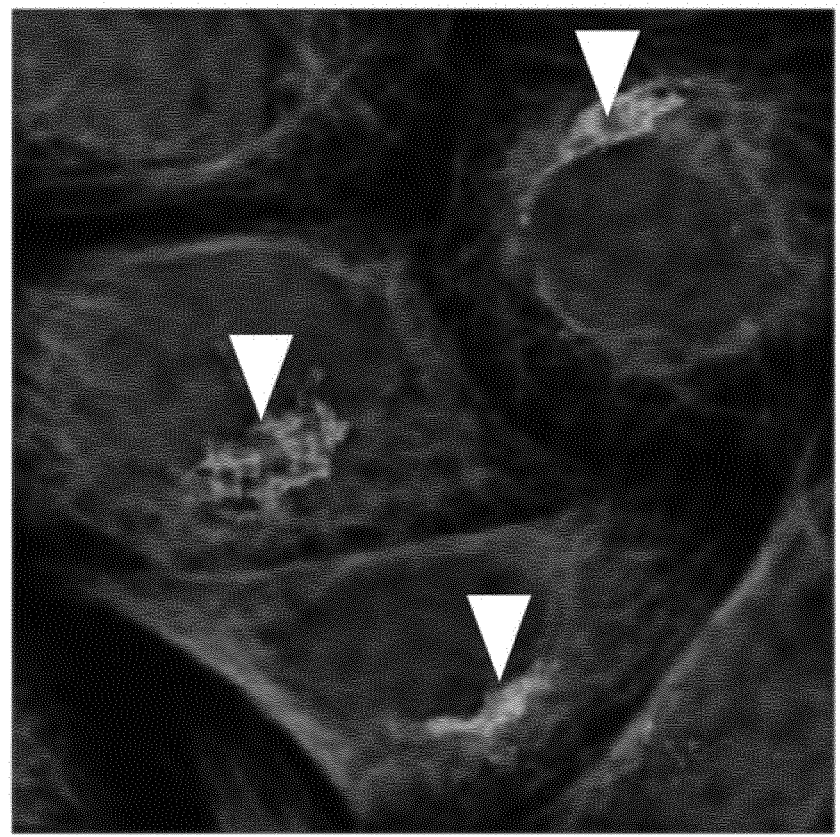
Figure 5:
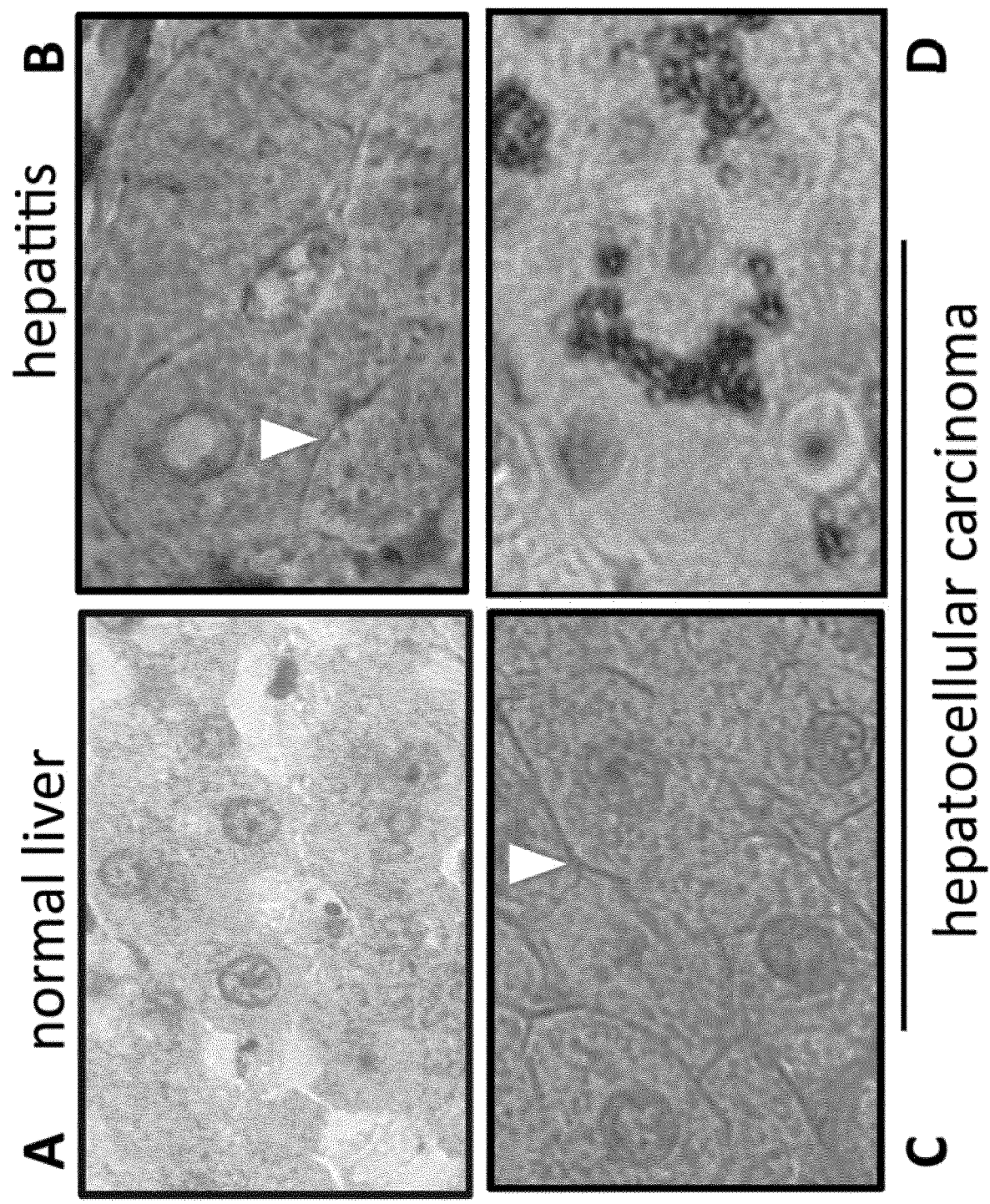
FIG. 5 Immunohistochemical staining of tissues with the anti-rGOLPH antibody G2-2 and controls. Paraffin embedded tissues of A normal liver B hepatitis liver C and D hepatocellular carcinoma (HCC) were stained with murine G2-2 (mG2-2) (A,B,C) or anti-GP73 antibody MO6A (Sigma) followed by secondary staining with an anti-mouse antibody and examined under a microscope by 40× magnification as described in Example 3.
Figure 6:
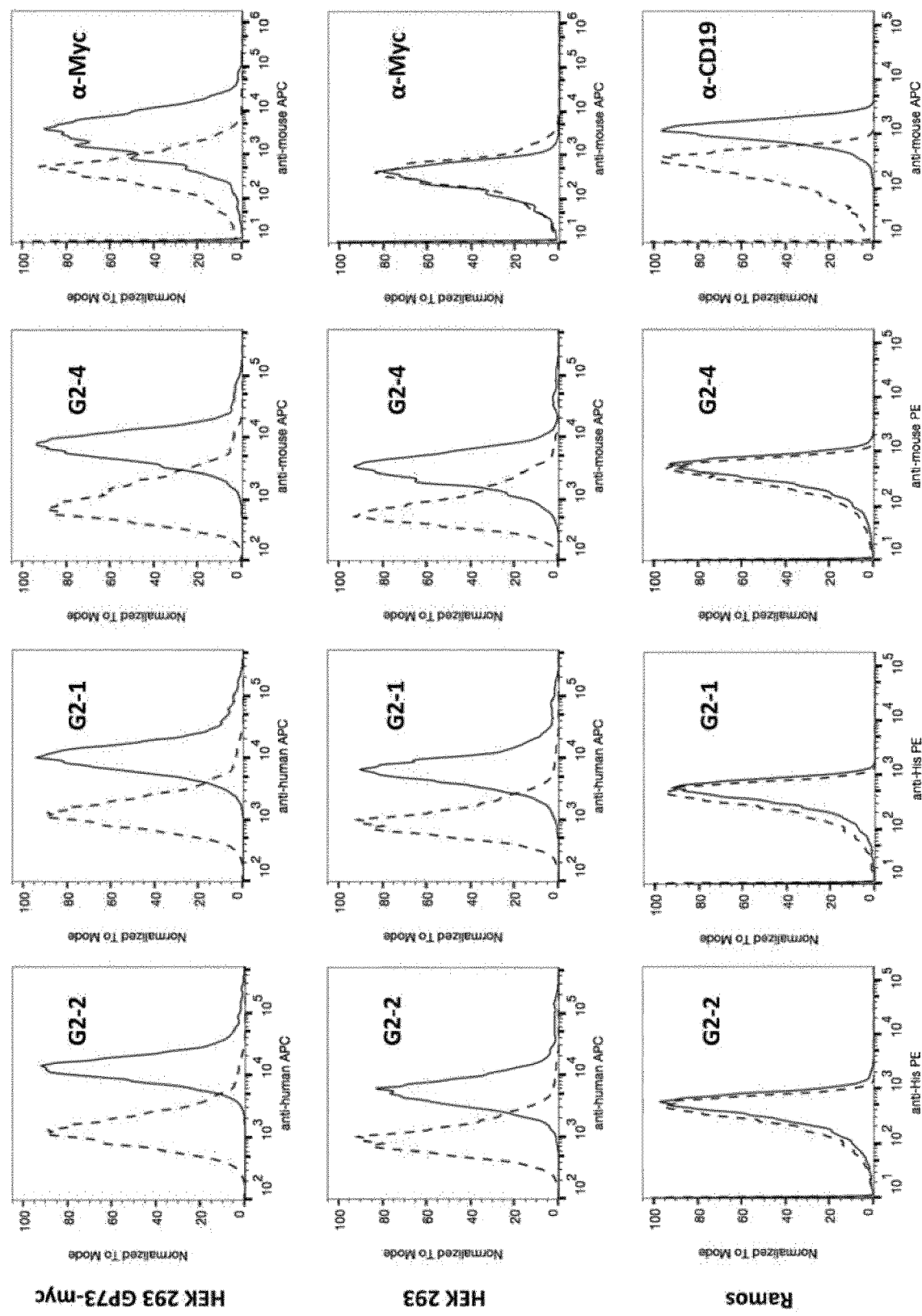
FIG. 6 Cell lines RAMOS (B-cell origin), HEK 293 (human embryonic kidney origin) and HEK 293 expressing GP73-myc (HEK 293 GP73-myc) were stained with G2-2, G2-1, G2-4, anti-Myc antibody or anti-CD19 antibody (latter from ebiosciences). Detection of surface staining of cells is depicted as continuous line, only secondary antibody control detection is depicted as dashed line as described in Example 4.
Figure 7:
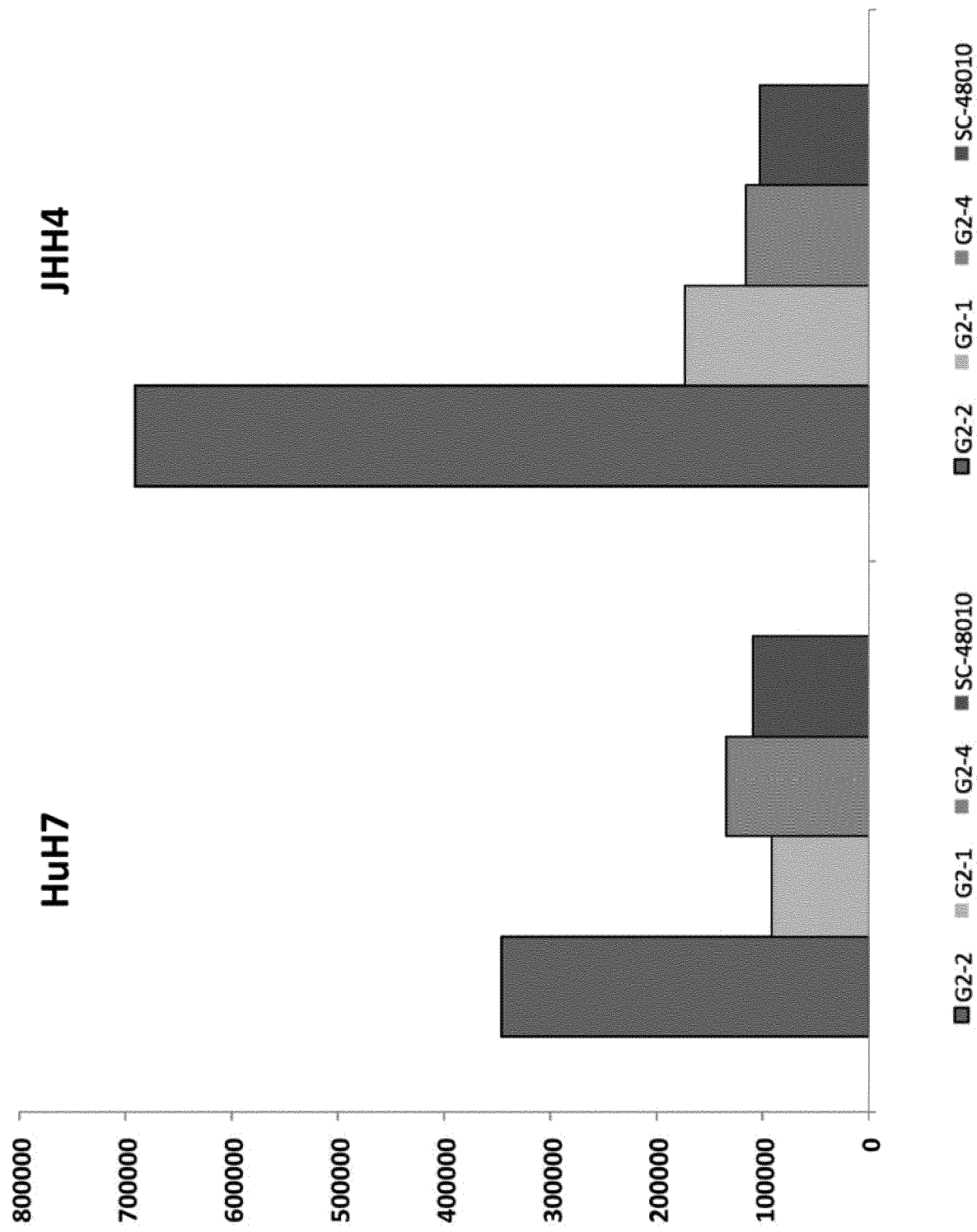
FIG. 7 GP73 surface expression tested with different antibodies (mG2-2, G2-1, G2-4 and polyclonal goat antibody SC-48010) on human hepatocellular carcinoma cell lines HuH7 and JHH4. The positivity of the respective cell lines is expressed as mean fluorescence intensity (MFI) as described in Example 4.
Figure 8:
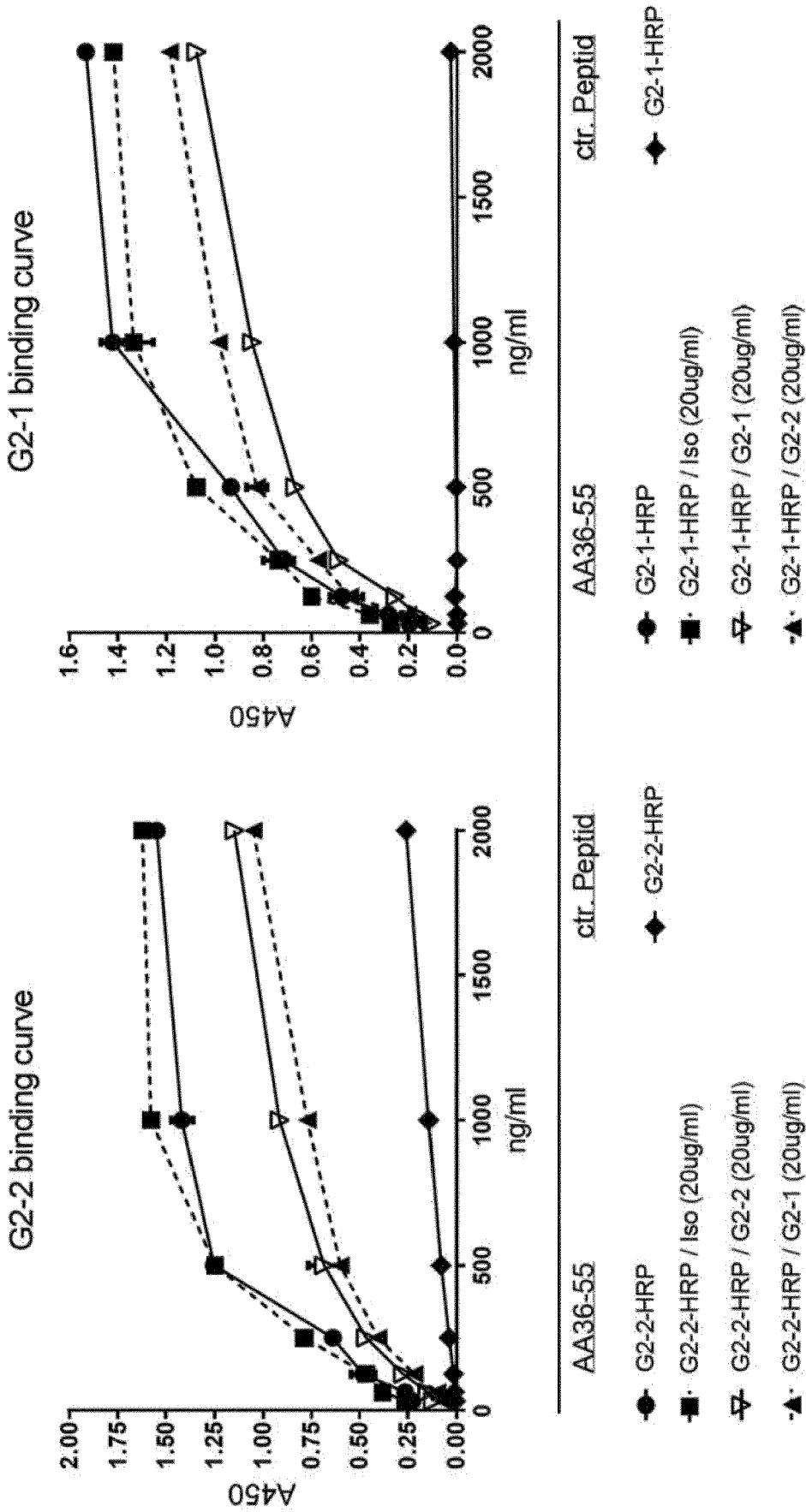
FIG. 8 Competition ELISA Assay

Provided herein are isolated antibodies that bind to GP73. The two exemplary naturally occurring human GP73 isoforms are depicted in SEQ ID NO: 1, and the corresponding processed GP73 form (amino acids 56-401), e.g. cleaved by protease depicted in FIG. 3

In some embodiments, an anti-GP73-antibody of the invention has at least one or more of the following characteristics, in any combination:
a) binds to recombinant human GP73
b) binds to endogenous GP73 on the surface of a cancer cell;
c) binds to an epitope within amino acids 36 to 55 of human GP73 on the surface of cancer cells (neo-epitope)
d) binds to endogenous GP73 on the surface of hepatocellular carcinoma cells;
e) binds to endogenous GP73 on the surface of cells of a cell line selected from HepG2, Hep3B, HuH7, JHH-7, Alexander (PLC/PRF/5), HLE, HuCCT1;
f) binds to endogenous GP73 on the surface of cells of a cell line selected from SKBR3 (breast cancer), SKOV3 (ovarian cancer), PC3 and DU145 (prostate cancer), HCT116, CaCo2, SW480 (colorectal cancer), H1975 (lung cancer);
g) binds to endogenous murine GP73 on the surface of cells of a cell line selected from Hep55-1C, Hepa1-6, Hep33.1c;
h) binds to endogenous murine GP73 on the surface of cells of a cell line selected from MDA and 4T1 (breast cancer), etc.
i) binds to endogenous rat GP73 on the surface of cells of a cell line selected from CRL2212
j) binds to an uncleaved GP73 on the surface of GP73 expressing cells (mentioned under a-i);
k) binds to an epitope within amino acids 36 to 55 of human GP73;
l) binds to an epitope spanning the putative furin cleavage recognition motif E50 to $R^{55}$ of human GP73;

In some embodiments, the characteristics of the antibody are determined as described herein, e.g., in the Examples below. In some embodiments, characteristics of the antibodies are determined by recombinant GP73 protein produced in 293 HEK cells. As a nonlimiting example, in some embodiments, full-length GP73 or a GP73 non-cleavable mutant (R52A) is expressed in cells (such as 293 HEK cells) and antibody binding to wildtype GP73 or the GP73 non-cleavable mutant or N-terminal truncated GP73 (AA56 to 401) is detected by ELISA or FACS.

Certain embodiments provided herein are based, in part, on the development of antibody G2-2 and/or G2-2opti, which binds to an epitope within amino acids 35 to 55 of human GP73 protein. In some embodiments, an antibody provided herein binds to an epitope within amino acids 35 to 55 of human GP73. In some such embodiments, an antibody provided herein comprises one or more CDR sequences of antibody G2-2.

Accordingly, in some embodiments, the invention provides an anti-GP73 antibody comprising at least one, two, three, four, five, or six CDRs selected from (a) CDR-H1 comprising the amino acid sequence of SEQ ID NO: 4; (b) CDR-H2 comprising the amino acid sequence of SEQ ID NO: 5; (c) CDR-H3 comprising the amino acid sequence of SEQ ID NO: 6; (d) CDR-L1 comprising the amino acid sequence of SEQ ID NO: 7; (e) CDR-L2 comprising the amino acid sequence of SEQ ID NO: 8; and (f) CDR-L3 comprising the amino acid sequence of SEQ ID NO: 9.

In one aspect, the invention provides an antibody comprising at least one, at least two, or all three VH CDR sequences selected from (a) CDR-H1 comprising the amino acid sequence of SEQ ID NO: 4; (b) CDR-H2 comprising the amino acid sequence of SEQ ID NO: 5; and (c) CDR-H3 comprising the amino acid sequence of SEQ ID NO: 6. In one embodiment, the antibody comprises CDR-H3 comprising the amino acid sequence of SEQ ID NO: 6. In another embodiment, the antibody comprises CDR-H3 comprising the amino acid sequence of SEQ ID NO: 6 and CDR-L3 comprising the amino acid sequence of SEQ ID NO: 9. In a further embodiment, the antibody comprises CDR-H3 comprising the amino acid sequence of SEQ ID NO: 6, CDR-L3 comprising the amino acid sequence of SEQ ID NO: 9, and CDR-H2 comprising the amino acid sequence of SEQ ID NO: 5. In a further embodiment, the antibody comprises (a) CDR-H1 comprising the amino acid sequence of SEQ ID NO: 4; (b) CDR-H2 comprising the amino acid sequence of SEQ ID NO: 5; and (c) CDR-H3 comprising the amino acid sequence of SEQ ID NO: 6.

In another aspect, the invention provides an antibody comprising at least one, at least two, or all three VL CDR sequences selected from (a) CDR-L1 comprising the amino acid sequence of SEQ ID NO: 7; (b) CDR-L2 comprising the amino acid sequence of SEQ ID NO: 8; and (c) CDR-L3 comprising the amino acid sequence of SEQ ID NO: 9. In one embodiment, the antibody comprises
(a) CDR-L1 comprising the amino acid sequence of SEQ ID NO: 7;
(b) CDR-L2 comprising the amino acid sequence of SEQ ID NO: 8; and
(c) CDR-L3 comprising the amino acid sequence of SEQ ID NO: 9.

In another aspect, an antibody of the invention comprises
(a) a VH domain comprising at least one, at least two, or all three VH CDR sequences selected from (i) CDR-H1 comprising the amino acid sequence of SEQ ID NO: 4, (ii) CDR-H2 comprising the amino acid sequence of SEQ ID NO: 5, and (iii) CDR-H3 comprising an amino acid sequence selected from SEQ ID NO: 6; and
(b) a VL domain comprising at least one, at least two, or all three VL CDR sequences selected from (i) CDR-L1 comprising the amino acid sequence of SEQ ID NO: 7, (ii) CDR-L2 comprising the amino acid sequence of SEQ ID NO: 8, and (iii) CDR-L3 comprising the amino acid sequence of SEQ ID NO: 9.

In another aspect, the invention provides an antibody comprising (a) CDR-H1 comprising the amino acid sequence of SEQ ID NO: 4; (b) CDR-H2 comprising the amino acid sequence of SEQ ID NO: 5; (c) CDR-H3 comprising the amino acid sequence of SEQ ID NO: 6; (d) CDR-L1 comprising the amino acid sequence of SEQ ID NO: 7; (e) CDR-L2 comprising the amino acid sequence of SEQ ID NO: 8; and (f) CDR-L3 comprising the amino acid sequence of SEQ ID NO: 9.

In another aspect, an anti-GP73 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 2 or SEQ ID NO: 35. In certain embodiments, a VH sequence having at least 90%, 91%, 92%, 93%, 94%, 95%, 96%, 97%, 98%, or 99% identity to the amino acid sequence of SEQ ID NO: 2 or SEQ ID NO: 35 contains substitutions (e.g., conservative substitutions), insertions, or deletions relative to the reference sequence, but an anti-GP73 antibody comprising that sequence retains the ability to bind to GP73. In certain embodiments, a total of 1 to 10 amino acids have been substituted, inserted and/or deleted in SEQ ID NO: 2 or SEQ ID NO: 35. In certain embodiments, a total of 1 to 5 amino acids have been substituted, inserted and/or deleted in SEQ ID NO: 2 or SEQ ID NO: 35. In certain embodiments, substitutions, insertions, or deletions occur in regions outside the CDRs (i.e., in the FRs). In a preferred embodiment, a total of 3 amino acids in SEQ ID NO: 2 have been substituted to optimize the expression in mammalian cells (SEQ ID NO: 35). Optionally, the anti-GP73 antibody comprises the VH sequence of SEQ ID NO: 2 or SEQ ID NO: 35, including post-translational modifications of that sequence. In a particular embodiment, the VH comprises one, two or three CDRs selected from: (a) CDR-H1 comprising the amino acid sequence of SEQ ID NO: 4, (b) CDRH2 comprising the amino acid sequence of SEQ ID NO: 5, and (c) CDR-H3 comprising the amino acid sequence of SEQ ID NO: 6.

In another aspect, an anti-GP73 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 3 or SEQ ID NO: 36. In certain embodiments, a VL sequence having at least 90%, 91%, 92%, 93%, 94%, 95%, 96%, 97%, 98%, or 99% identity to the amino acid sequence of SEQ ID NO: 3 or SEQ ID NO: 36 contains substitutions (e.g., conservative substitutions), insertions, or deletions relative to the reference sequence, but an anti-GP73 antibody comprising that sequence retains the ability to bind to GP73. In certain embodiments, a total of 1 to 10 amino acids have been substituted, inserted and/or deleted in SEQ ID NO: 3 or SEQ ID NO: 36. In certain embodiments, a total of 1 to 5 amino acids have been substituted, inserted and/or deleted in SEQ ID NO: 3 or SEQ ID NO: 36. In certain embodiments, the substitutions, insertions, or deletions occur in regions outside the CDRs (i.e., in the FRs). In a preferred embodiment, a total of 8 amino acids in SEQ ID NO: 3 have been substituted to optimize the expression in mammalian cells (SEQ ID NO: 36). Optionally, the anti-GP73 antibody comprises the VL sequence of SEQ ID NO: 3 or SEQ ID NO: 36, including post-translational modifications of that sequence. In a particular embodiment, the VL comprises one, two or three CDRs selected from (a) CDR-L1 comprising the amino acid sequence of SEQ ID NO: 7; (b) CDR-L2 comprising the amino acid sequence of SEQ ID NO: 8; and (c) CDR-L3 comprising the amino acid sequence of SEQ ID NO: 9.

In another aspect, an anti-GP73 antibody is provided, wherein the antibody comprises a VH as in any of the embodiments provided above, and a VL as in any of the embodiments provided above. In a preferred embodiment, the antibody comprises the VH and VL sequences in SEQ ID NO: 35 and SEQ ID NO: 36, respectively, including post-translational modifications of those sequences. In another preferred embodiment, an anti-GP73 antibody comprises a humanized form of an antibody comprising the VH and VL sequences in SEQ ID NO: 35 and SEQ ID NO: 36, respectively. In one embodiment, the antibody comprises the VH and VL sequences in SEQ ID NO: 2 and SEQ ID NO: 3, respectively, including post-translational modifications of those sequences. In another embodiment, an anti-GP73 antibody comprises a humanized form of an antibody comprising the VH and VL sequences in SEQ ID NO: 2 and SEQ ID NO: 3, respectively.

In a further aspect, provided herein are antibodies that bind to the same epitope as an anti-GP73 antibody provided herein. In a preferred embodiment, an antibody is provided that binds to the same epitope as an anti-GP73 antibody comprising a VH sequence of SEQ ID NO: 37 and a VL sequence of SEQ ID NO: 38, respectively. In certain embodiments, an antibody is provided that binds to the same epitope as an anti-GP73 antibody comprising a VH sequence of SEQ ID NO: 10 and a VL sequence of SEQ ID NO: 11, respectively.

In a further aspect of the invention, an anti-GP73 antibody according to any of the above embodiments is a monoclonal antibody, including a human antibody. In one embodiment, an anti GP73 antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

In a further aspect, the anti-GP73 antibody according to any of the above embodiments comprises a heavy chain constant region sequence comprising the amino acid sequence of SEQ ID NO: 28, preferably of SEQ ID NO: 39 (which is an modified version of SEQ ID NO: 28 in order to optimize the expression in mammalian cells). In another aspect, an anti-GP73 antibody comprises a heavy chain constant region sequence having at least 90%, 91%, 92%, 93%, 94%, 95%, 96%, 97%, 98%, 99%, or 100% sequence identity to the amino acid sequence of SEQ ID NO: 28 or SEQ ID NO: 39.

In a further aspect, an anti-GP73 antibody according to any of the above embodiments may incorporate any of the features, singly or in combination, as described below.

Certain embodiments provided herein are based, in part, on the development of antibody G2-1, which binds to an epitope within amino acids 36 to 55 of human GP73 protein. In some embodiments, an antibody provided herein binds to an epitope within amino acids 347 to 366 of human GP73. In some such embodiments, an antibody provided herein comprises one or more CDR sequences of antibody G2-1.

In some embodiments, the invention provides an anti-GP73 antibody comprising at least one, two, three, four, five, or six CDRs selected from (a) CDR-HI comprising the amino acid sequence of SEQ ID NO: 12; (b) CDR-H2 comprising the amino acid sequence of SEQ ID NO: 13; (c) CDR-H3 comprising the amino acid sequence of SEQ ID NO: 14; (d) CDR-LI comprising the amino acid sequence of SEQ ID NO: 15; (e) CDR-L2 comprising the amino acid sequence of SEQ ID NO: 16; and (f) CDR-L3 comprising the amino acid sequence of SEQ ID NO: 17 or SEQ ID NO: 44.

In one aspect, the invention provides an antibody comprising at least one, at least two, or all three VH CDR sequences selected from (a) CDR-HI comprising the amino acid sequence of SEQ ID NO: 12; (b) CDR-H2 comprising the amino acid sequence of SEQ ID NO: 13; and (c) CDR-H3 comprising the amino acid sequence of SEQ ID NO: 14. In one embodiment, the antibody comprises CDR-H3 comprising the amino acid sequence of SEQ ID NO: 14. In another embodiment, the antibody comprises CDR-H3 comprising the amino acid sequence of SEQ ID NO: 14 and CDR-L3 comprising the amino acid sequence of SEQ ID NO: 17 or SEQ ID NO: 44. In a further embodiment, the antibody comprises CDR-H3 comprising the amino acid sequence of SEQ ID NO: 14, CDR-L3 comprising the amino acid sequence of SEQ ID NO: 17 or SEQ ID NO: 44, and CDR-H2 comprising the amino acid sequence of SEQ ID NO: 13. In a further embodiment, the antibody comprises (a) CDR-HI comprising the amino acid sequence of SEQ ID NO: 12; (b) CDR-H2 comprising the amino acid sequence of SEQ ID NO: 13; and (c) CDR-H3 comprising the amino acid sequence of SEQ ID NO: 14.

In another aspect, the invention provides an antibody comprising at least one, at least two, or all three VL CDR sequences selected from (a) CDR-L1 comprising the amino acid sequence of SEQ ID NO: 15; (b) CDR-L2 comprising the amino acid sequence of SEQ ID NO: 16; and (c) CDR-L3 comprising the amino acid sequence of SEQ ID NO: 17 or SEQ ID NO: 44. In one embodiment, the antibody comprises
(a) CDR-L1 comprising the amino acid sequence of SEQ ID NO: 15;
(b) CDR-L2 comprising the amino acid sequence of SEQ ID NO: 16; and
(c) CDR-L3 comprising the amino acid sequence of SEQ ID NO: 17 or SEQ ID NO: 44.

In another aspect, an antibody of the invention comprises (a) a VH domain comprising at least one, at least two, or all three VH CDR sequences selected from (i) CDR-H1 comprising the amino acid sequence of SEQ ID NO: 12, (ii) CDR-H2 comprising the amino acid sequence of SEQ ID NO: 13, and (iii) CDR-H3 comprising an amino acid sequence selected from SEQ ID NO: 14; and
(b) a VL domain comprising at least one, at least two, or all three VL CDR sequences selected from (i) CDR-L1 comprising the amino acid sequence of SEQ ID NO: 15, (ii) CDR-L2 comprising the amino acid sequence of SEQ ID NO: 16, and (iii) CDR-L3 comprising the amino acid sequence of SEQ ID NO: 17 or SEQ ID NO: 44.

In another aspect, the invention provides an antibody comprising (a) CDR-H1 comprising the amino acid sequence of SEQ ID NO: 12; (b) CDR-H2 comprising the amino acid sequence of SEQ ID NO: 13; (c) CDR-H3 comprising the amino acid sequence of SEQ ID NO: 14; (d) CDR-L1 comprising the amino acid sequence of SEQ ID NO: 15; (e) CDR-L2 comprising the amino acid sequence of SEQ ID NO: 16; and (f) CDR-L3 comprising the amino acid sequence of SEQ ID NO: 17 or SEQ ID NO: 44.

In another aspect, an anti-GP73 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10 or SEQ ID NO: 37. In certain embodiments, a VH sequence having at least 90%, 91%, 92%, 93%, 94%, 95%, 96%, 97%, 98%, or 99% identity to the amino acid sequence of SEQ ID NO: 10 or SEQ ID NO: 37 contains substitutions (e.g., conservative substitutions), insertions, or deletions relative to the reference sequence, but an anti-GP73 antibody comprising that sequence retains the ability to bind to GP73. In certain embodiments, a total of 1 to 10 amino acids have been substituted, inserted and/or deleted in SEQ ID NO: 10 or SEQ ID NO: 37. In certain embodiments, a total of 1 to 5 amino acids have been substituted, inserted and/or deleted in SEQ ID NO: 10 or SEQ ID NO: 37. In certain embodiments, substitutions, insertions, or deletions occur in regions outside the CDRs (i.e., in the FRs). In a preferred embodiment, a total of 6 amino acids in SEQ ID NO: 10 have been substituted to optimize the expression in mammalian cells (SEQ ID NO: 37). Optionally, the anti-GP73 antibody comprises the VH sequence of SEQ ID NO: 10 or SEQ ID NO: 37, including post-translational modifications of that sequence. In a particular embodiment, the VH comprises one, two or three CDRs selected from: (a) CDR-H1 comprising the amino acid sequence of SEQ ID NO: 12, (b) CDRH2 comprising the amino acid sequence of SEQ ID NO: 13, and (c) CDR-H3 comprising the amino acid sequence of SEQ ID NO: 14.

In another aspect, an anti-GP73 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11 or SEQ ID NO: 38. In certain embodiments, a VL sequence having at least 90%, 91%, 92%, 93%, 94%, 95%, 96%, 97%, 98%, or 99% identity to the amino acid sequence of SEQ ID NO: 11 or SEQ ID NO: 38 contains substitutions (e.g., conservative substitutions), insertions, or deletions relative to the reference sequence, but an anti-GP73 antibody comprising that sequence retains the ability to bind to GP73. In certain embodiments, a total of 1 to 10 amino acids have been substituted, inserted and/or deleted in SEQ ID NO: 11 or SEQ ID NO: 38. In certain embodiments, a total of 1 to 5 amino acids have been substituted, inserted and/or deleted in SEQ ID NO: 11 or SEQ ID NO: 38. In certain embodiments, the substitutions, insertions, or deletions occur in regions outside the CDRs (i.e., in the FRs). In a preferred embodiment, a total of 10 amino acids in SEQ ID NO: 11 have been substituted to optimize the expression in mammalian cells (SEQ ID NO: 38). Optionally, the anti-GP73 antibody comprises the VL sequence of SEQ ID NO: 11 or SEQ ID NO: 38, including post-translational modifications of that sequence. In a particular embodiment, the VL comprises one, two or three CDRs selected from (a) CDR-L1 comprising the amino acid sequence of SEQ ID NO: 15; (b) CDR-L2 comprising the amino acid sequence of SEQ ID NO: 16; and (c) CDR-L3 comprising the amino acid sequence of SEQ ID NO: 17 or SEQ ID NO: 44.

In another aspect, an anti-GP73 antibody is provided, wherein the antibody comprises a VH as in any of the embodiments provided above, and a VL as in any of the embodiments provided above. In a preferred embodiment, the antibody comprises the VH and VL sequences in SEQ ID NO: 37 and SEQ ID NO: 38, respectively, including post-translational modifications of those sequences. In another embodiment, an anti-GP73 antibody comprises a humanized form of an antibody comprising the VH and VL sequences in SEQ ID NO: 37 and SEQ ID NO: 38, respectively. In one embodiment, the antibody comprises the VH and VL sequences in SEQ ID NO: 10 and SEQ ID NO: 11, respectively, including post-translational modifications of those sequences. In another embodiment, an anti-GP73 antibody comprises a humanized form of an antibody comprising the VH and VL sequences in SEQ ID NO: 10 and SEQ ID NO: 11, respectively.

In a further aspect, provided are herein are antibodies that bind to the same epitope as an anti-GP73 antibody provided herein. In a preferred embodiment, an antibody is provided that binds to the same epitope as an anti-GP73 antibody comprising a VH sequence of SEQ ID NO: 35 and a VL sequence of SEQ ID NO: 36, respectively. In certain embodiments, an antibody is provided that binds to the same epitope as an anti-GP73 antibody comprising a VH sequence of SEQ ID NO: 2 and a VL sequence of SEQ ID NO: 3, respectively.

In a further aspect of the invention, an anti-GP73 antibody according to any of the above embodiments is a monoclonal antibody, including a human antibody. In one embodiment, an anti GP73 antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

In a further aspect, the anti-GP73 antibody according to any of the above embodiments comprises a heavy chain constant region sequence comprising the amino acid sequence of SEQ ID NO: 28, preferably of SEQ ID NO: 39. In another aspect, an anti-GP73 antibody comprises a heavy chain constant region sequence having at least 90%, 91%, 92%, 93%, 94%, 95%, 96%, 97%, 98%, 99%, or 100% sequence identity to the amino acid sequence of SEQ ID NO: 28 or SEQ ID NO: 39.

In a further aspect, an anti-GP73 antibody according to any of the above embodiments may incorporate any of the features, singly or in combination, as described below.

In certain embodiments, an antibody provided herein has a dissociation constant (Kd) of ≤1 μM, ≤100 nM, ≤50 nM, ≤10 nM, ≤5 nM, ≤1 nM, ≤0.1 nM, ≤0.01 nM, or ≤0.001 nM, and optionally is $10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured using surface plasmon resonance assays using a BIACORE®-2000 or a BIA-CORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl) carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of antibody (0.58 nM to 200 nM) are injected in PBS with 0.05% polysorbate 20 (TWEEN-20™) surfactant (PEST) at 25° C. at a flow rate of approximately 25 μl/min. Association rates (kon) and dissociation rates (koff) are calculated using a simple one-to-one Langmuir binding model (BIACORE® T100 Evaluation Software) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds $106\ M^{-1}\ s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

TABLE 1

| Biacore data fit for 1:1 binding | | | |
|---|---|---|---|
| antibody | measurement 1 + 2 mean (+/-) $k_{on}$ [$M^{-1}\ s^{-1}$] | measurement 1 + 2 mean (+/-) $k_{off}$ [$s^{-1}$] | measurement 1 + 2 mean (+/-) Kd [nM] |
| G2-2 | $2.602 \times 10^5$ (+/-0.375 × $10^5$) | $1.108 \times 10^{-3}$ (+/-0.375 × $10^{-3}$) | 4.293 (+/-0.233) |
| G2-1 | $6.352 \times 10^5$ (+/-1.810 × $10^5$) | $1.981 \times 10^{-3}$ (+/-0.757 × $10^{-3}$) | 3.024 (+/-0.331) |

GP73 peptide: SSRSVDLQTRIMELEGRVRR
Analyse Software: Biacore T100 Evaluation Software (GE Healthcare Life Sciences)

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe Norleucine | Leu |
| Leu (L) | Norleucine; Ile; Val; Met; Ala Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Led 3 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et at, especially at Example 11), and knockout cell lines, such as alpha-1,6-fucosyltransferase gene, FUT8, knockout CHO cells (see, e.g., Yamane-Ohnuki et al. *Bioteeh. Bioeng.* 87: 614 (2004); Kanda, Y. et al., *Bioteehnok Bioeng.*, 94(4):680-688 (2006); and WO2003/085 I07).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et aid. Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)).

Alternatively, non-radioactive assays methods may be employed (see, for example, ACTI™ non radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells.

Alternatively, or additionally, ADCC activity of the molecule of interest may be assessed in vivo, e.g., in a animal model such as that disclosed in Clynes et al. *Proc. Nat'l Acad. sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).

In certain embodiments, an antibody variant comprises a Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kirn et al., *J. Immunol.* 24:249 (1994)), are described in US2005/0014934AI (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Nonlimiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Antibodies may be produced using recombinant methods and compositions, e.g., as described in U.S. Pat. No. 4,816,567. In one embodiment, isolated nucleic acid encoding an anti-GP73 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20). In one embodiment, a method of making an anti-GP73 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-GP73 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Val. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are macaque kidney CVI line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, *Biol. Reprod.* 23:243-251 (1980)); macaque kidney cells (CV I); African green macaque kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. cii. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

Anti-GP73 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, immunofluorescence or immunohistochemistry.

In another aspect, competition assays may be used to identify an antibody that competes with any of the antibodies described herein for binding to GP73. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized GP73 is incubated in a solution comprising a first labeled antibody that binds to GP73 (e.g., any of the antibodies described herein) and a second unlabeled antibody that is being tested for its ability to compete with the first antibody for binding to GP73. As a control, immobilized GP73 is incubated in a solution comprising the first labeled antibody but not the second unlabeled antibody. After incubation under conditions permissive for binding of the first antibody to GP73, excess unbound antibody is removed, and the amount of label associated with immobilized GP73 is measured. If the amount of label associated with immobilized GP73 is substantially reduced in the test sample relative to the control sample, then that indicates that the second antibody is competing with the first antibody for binding to GP73. See Harlow and Lane (1988) *Antibodies: A Laboratory Manual* ch. 14 (Cold Spring Harbor Laboratory, Cold Spring Harbor, N.Y.).

The invention also provides immunoconjugates comprising an anti-GP73 antibody herein conjugated to an endosomal escape domain (EED) peptide or one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

An exemplary embodiment of an antibody-EED conjugate compound comprises an antibody (Ab) which targets a tumor cell, an EED peptide, and an EED linker (EEDL) that attaches Ab to the EED peptide. The EED may be directly attached as a tag to the antibody with a suitable linker peptide as described in SEQ ID NO:43. An exemplary antibody-EED conjugate compound has the formula Ab(-EEDL-EED peptide). EED peptides include, but are not limited to, dengue virus and other virus derived EED peptides and variants thereof, bacterial derived EED and peptides containing two aromatic indole rings or one indole ring and two aromatic phenyl groups (WO 2016/015621; WO 2016/037985; Kiesgen et al., Protein Eng Des Sel. 27(10): 331-7 (2014) and Lohn et al., Sci Rep. 6:32301 (2016).

Antibody-drug conjugates (ADC) are targeted chemotherapeutic molecules which combine properties of both antibodies and cytotoxic drugs by targeting potent cytotoxic drugs to antigen expressing tumor cells (Teicher, B. A. (2009) *Current Cancer Drug Targets* 9:982-1004), thereby enhancing the therapeutic index by maximizing efficacy and minimizing off-target toxicity (Carter, and Senter P. D. (2008) *The Cancer Jour.* 14(3): 154-169; Chari, R. V. (2008) *Ace. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

1.1 1. Exemplary Antibody-Drug Conjugates
1.2

An exemplary embodiment of an antibody-drug conjugate (ADC) compound comprises an antibody (Ab) which targets a tumor cell, a drug moiety (D), and a linker moiety (L) that attaches Ab to D. The antibody may be attached to the linker moiety (L) through one or more amino acid residues, such as lysine and/or cysteine.

An exemplary ADC has Formula I:

$$Ab(\text{-}L\text{-}D)_p \qquad \qquad I$$

where p is 1 to about 20.

The number of drug moieties that can be conjugated to an antibody may be limited by the number of free cysteine residues. Free cysteine residues can be introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a. Exemplary Linkers

A "Linker" (L) is a bifunctional or multifunctional moiety that can be used to link one or more drug moieties (D) to an antibody (Ab) to form an antibody-drug conjugate (ADC) of Formula 1. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Non-limiting examples of such reactive functionalities include maleimide, haloacetamides, a-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method disclosed on page 766 of Klussman, et al (2004), *Bioconjugate Chemistry* 15(4):765-773, and the examples disclosed herein.

A linker may have a functionality that is capable of reacting with an electrophilic group present on an antibody. Exemplary electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Non-limiting examples of such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), p-aminobenzyloxycarbonyl (a "PAB"), N-succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Non-limiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

A linker component may comprise a "stretcher unit" that links an antibody to another linker component or to a drug moiety. Non-limiting exemplary stretcher units are shown below (wherein the wavy line indicates sites of covalent attachment to an antibody, drug, or additional linker components):

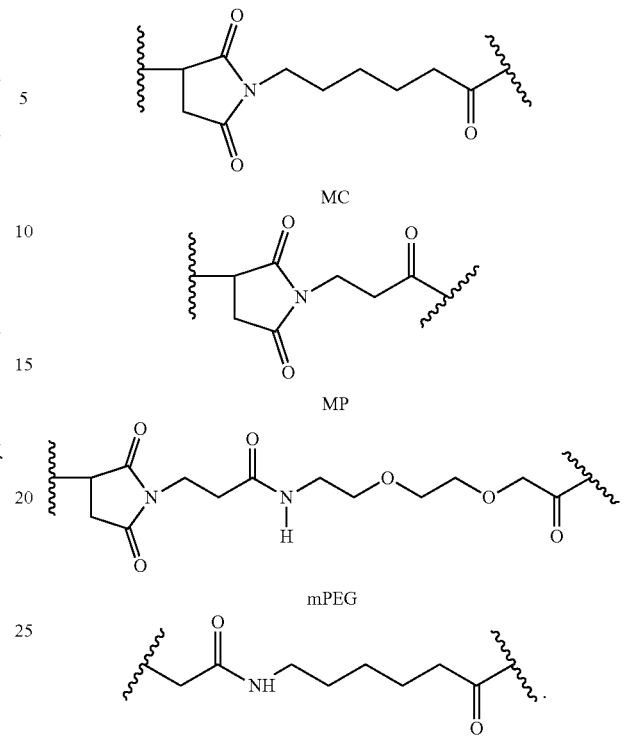

A linker component may comprise a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. Enzymatic cleavage of an ADC containing a glycine-glycine spacer unit by a tumor-cell associated protease may result in release of a glycine-glycine drug moiety from the remainder of the ADC. In some of these cases, the glycine-glycine-drug moiety is subjected to a hydrolysis step in the tumor cell, thus cleaving the glycine-glycine spacer unit from the drug moiety.

A "self-immolative" spacer unit allows for release of the drug moiety. A spacer unit of a linker may comprise a p-aminobenzyl unit. Furthermore, a p-aminobenzyl alcohol may be attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). The spacer unit may be paminobenzyloxycarbonyl (PAB). An ADC comprising a self-immolative inker may have the structure:

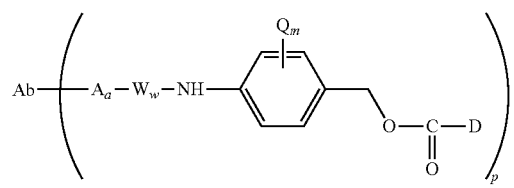

wherein Q is —$C_1$-$C_8$ alkyl, —O—($C_1$-$C_8$ alkyl), -halogen, -nitro, or -cyano;

m is an integer ranging from 0 to 4;

p ranges from 1 to about 20. Preferably, p ranges from 1 to 10, 1 to 7, 1 to 5, or 1 to 4.

A is an optional acyl group, a ranges from 0 to 8, W is an optional second self immolative group with w ranging from 0-1.

Other examples of self-immolative spacers include, but are not limited to, aromatic compounds that are electrochemically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

The linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

In some embodiments, a linker is substituted with groups that modulate solubility and/or reactivity. As a non-limiting example, a charged substituent such as sulfonate (—SO$_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula 1. In some such embodiments, the antibody comprises more than one (linker portion)$^a$ substituents, such that more than one drug is coupled to the antibody in the ADC of Formula 1.

The compounds of the invention expressly comprise, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bisvinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-maleimidophenyl) butyric acid hydrazide (MPBH), succinimidyl 3-(bromoacetamido)propionate (SBAP), succinimidyl iodoacetate (SIA), succinimidyl(4-iodoacetyl)aminobenzoate (SIAB), Nsuccinimidyl-3-(2-pyridyldithio)propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB (sulfosuccinimidyl 4-(N-maleimidophenyl)butyrate)), and succinimidyl-(4-vinylsulfone)benzoate (SVSB), and including bis-maleimide reagents: dithiobismaleimidoethane (DTME), 1,4-bismaleimidobutane (BMB), 1,4-bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene-2,6-diisocyanate), and bis-active fluorine compounds (such as 1,5-difluoro-2,4-dinitrobenzene).

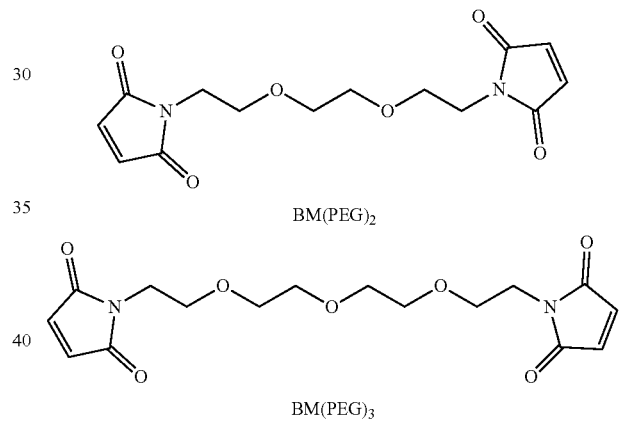

BM(PEG)$_2$

BM(PEG)$_3$

Bis-maleimide reagents can allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Dubowchik et al. (1997) Tetrahedron Letters, 38:5257-60; Walker, M. A. (1995) J. Org. Chem. 60:5352-5355; Frisch et al. (1996) Bioconjugate Chem. 7:180-186; U.S. Pat. No. 6,214,345; WO 02/088172; US 2003/130189; US 2003/096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO 94/11026.

b) Exemplary Drug Moieties
(1) Maytansine and Maytansinoids

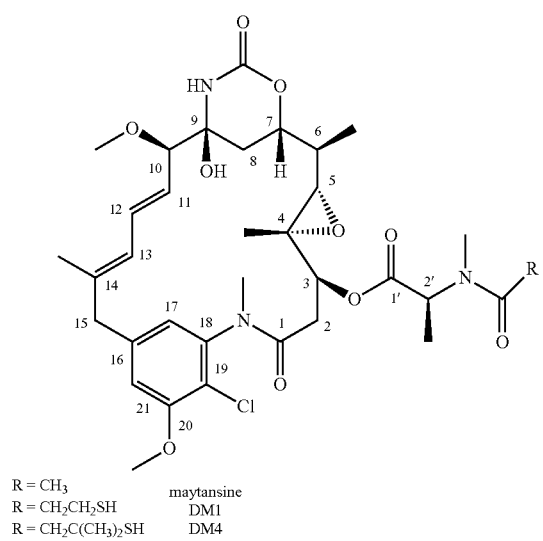

R = CH₃       maytansine
R = CH₂CH₂SH  DM1
R = CH₂C(CH₃)₂SH  DM4

An immuno conjugate may comprise an antibody conjugated to one or more maytansinoid molecules. Maytansinoids are derivatives of maytansine, where the methyl group at C1 is substituted preferrably by a thioethanyl group or $CH_2C(CH_3)_2SH$. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods (US Pat. No. 2011/158991).

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl) +/−C-19-dechloro (U.S. Pat. Nos. 4,361,650 and 4,307,016) (prepared, for example, by demethylation using *Streptomyces* or *Actinomyces* or dechlorination using LAH (lithium aluminium hydride, cf. U.S. Pat. No. 4,294,757); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with $H_2S$ or P2S5); C-14-alkoxymethyl(demethoxy/$CH_2$ OR) (U.S. Pat. No. 4,331,598); C-14-hydroxymethyl or acyloxymethyl ($CH_2OH$ or $CH_2OAC$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudiflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

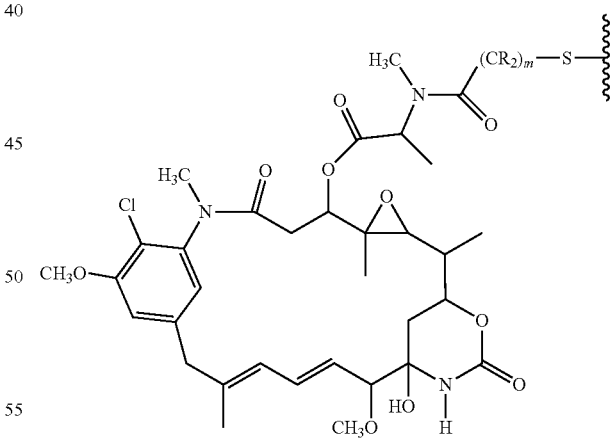

where the wavy line indicates the covalent attachment of the sulfur atom of the maytansinoid drug moiety to a linker of an ADC. Each R may independently be H or $C_1$-$C_6$ alkyl. The "alkylene" chain, i.e. $(CR_2)_m$, attaching the amide group to the sulfur atom is as defined above, and may, e.g. be methylene, ethylene, propylene, i.e., m is 1, 2, or 3 (U.S. Pat. Nos. 633,410; 5,208,020; Chari et al. (1992) *Cancer Res.* 52:127-131; Liu et al (1996) *Proc. Natl. Acad. Sci USA* 93:8618-8623), which are incorporated by reference in their entirety.

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; US RE 39,151; U.S. Pat. No. 5,208,020; Widdison et al. (2006) J. Med. Chem. 49:4392-4408, which are incorporated by reference in their entirety).

In some embodiments, the maytansinoid drug moiety has the following stereochemistry:

Exemplary embodiments of maytansinoid drug moieties include, but are not limited to, DM1; DM3; and DM4, having the structures:

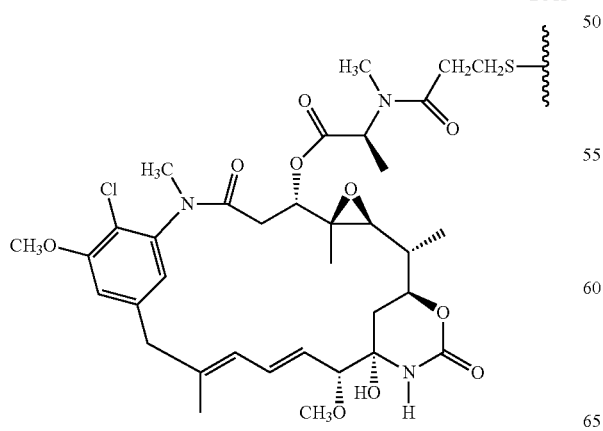

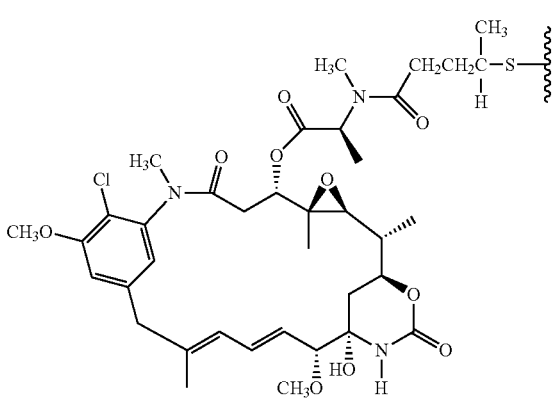

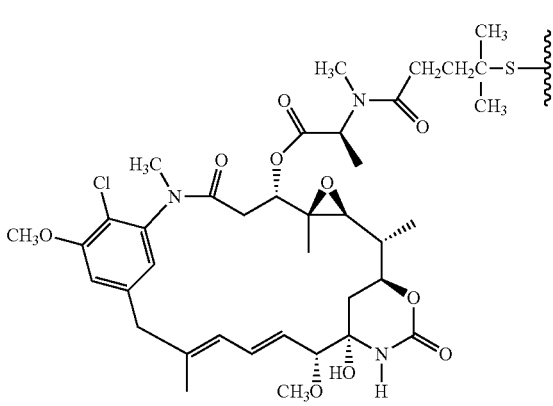

wherein the wavy line indicates the covalent attachment of the sulfur atom of the drug to a linker (L) of an antibody-drug conjugate.

Other exemplary maytansinoid antibody-drug conjugates have the following structures and abbreviations:

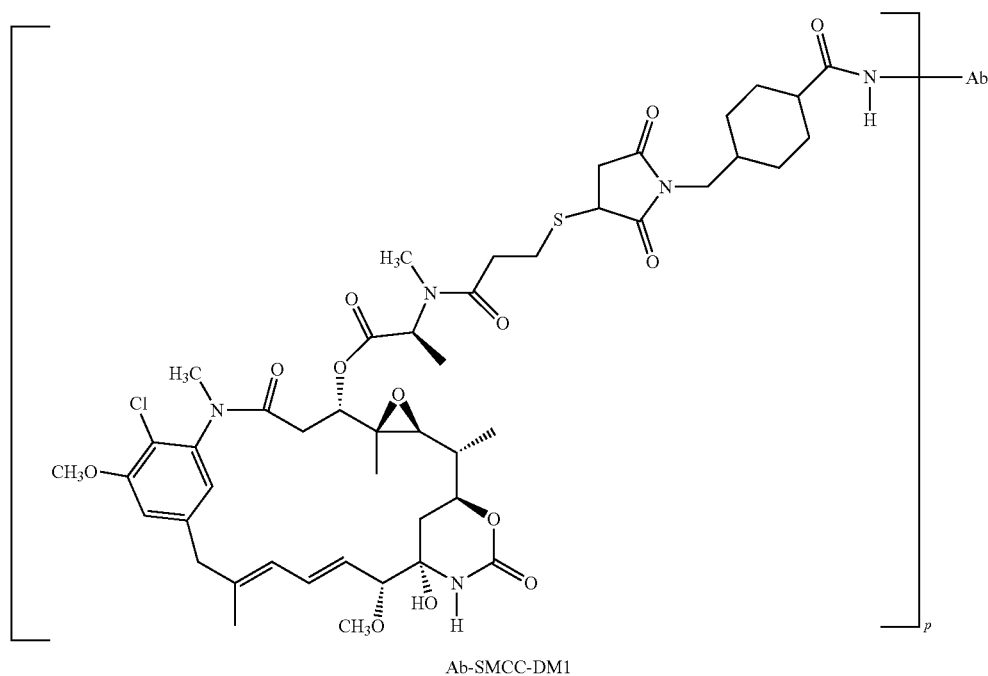
Ab-SMCC-DM1
wherein Ab is an antibody and p is 1 to about 20, preferably, p is 1 to 10, p is 1 to 7, p is 1 to 5, p is 1 to 4 or p is 1 to 2. SMCC is succinimidyl 4-(N-maleimidomethyl)cyclohexane-1-carboxylate and DM1 is as defined above.
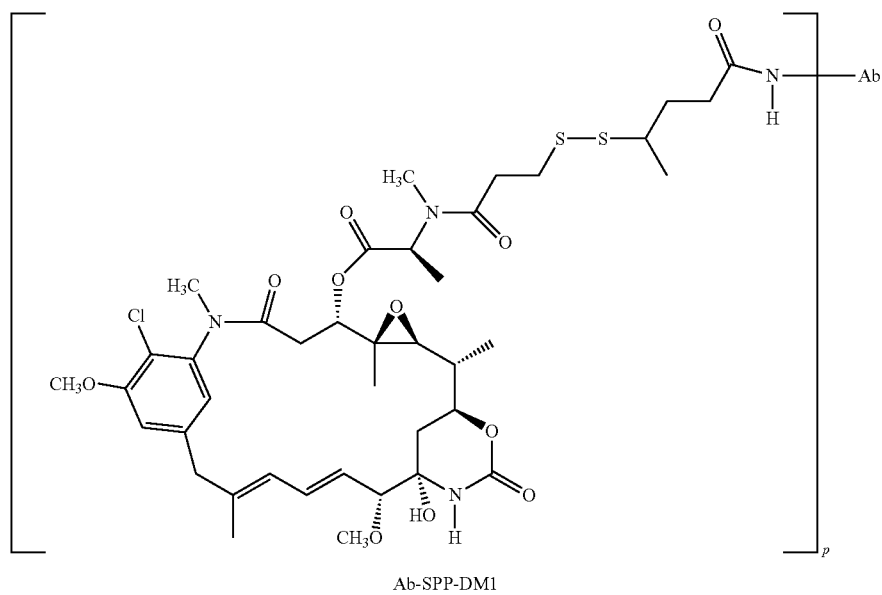
Ab-SPP-DM1 wherein Ab is antibody and p is 1 to about 20, preferably, p is 1 to 10, p is 1 to 7, p is 1 to 5, p is 1 to 4 or p is 1 to 2). SPP is N-succinimidyl 4-(2-pyridylthio) pentanoate and DM1 is as defined above.

Exemplary antibody-drug conjugates where DM1 is linked through a BMPEO (bis-maleimido-trioxyethylene glycol) linker to a thiol group of the antibody have the structure:

The antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). ADC with an average of 3-4 maytansinoid molecules conjugated per antibody molecule has shown efficacy in enhancing cytotoxicity

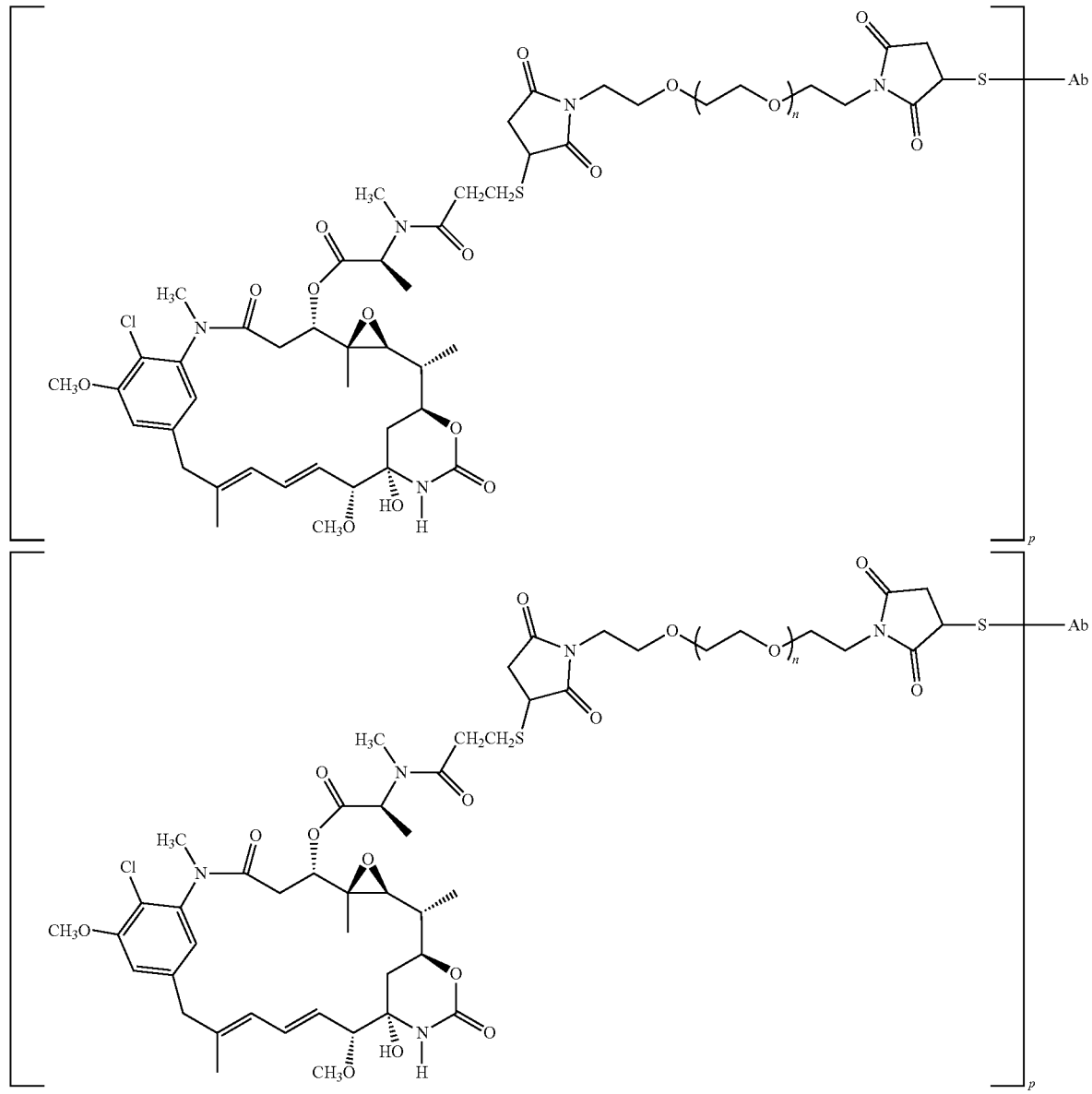

where Ab is antibody; n is 0, 1, or 2; and p is 1 to about 20, preferably, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020, 5,416,064; US 2005/0276812 A1 and European Patent EP 0 425 235 B1, the disclosures of which are hereby expressly incorporated by reference. See also Liu et al. Proc. Natl. Acad. Sci. USA 93:8618-8623 (1996); and Chari et al. Cancer Research 52:127-131 (1992).

of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. Cancer Research 52:127-131 (1992); US 2005/0276812 A1; and US 2005/016993 A1, the disclosures of which are hereby expressly incorporated by reference.

1.1.1.1 (2) Calicheamicin

The immunoconjugate may comprise an antibody conjugated to one or more calicheamicin molecules. The calicheamicin family of antibiotics, and analogues thereof, are capable of producing double-stranded DNA breaks at subpicomolar concentrations (Hinman et al., (1993) Cancer Research 53:3336-3342; Lode et al., (1998) Cancer Research 58:2925-2928). Calicheamicin has intracellular sites of action but, in certain instances, does not readily cross the plasma membrane. Therefore, cellular uptake of these agents through antibody-mediated internalization may, in some cases, greatly enhance their cytotoxic effects. Non-limiting exemplary methods of preparing antibody-drug conjugates with a calicheamicin drug moiety are described, for example, in U.S. Pat. Nos. 5,712,374; 5,714,586; 5,739,116; and 5,767,285.

(4) Pyrrolobenzodiazepines

The ADC may comprise a pyrrolobenzodiazepine (PBD). PDB dimers can recognize and bind to specific DNA sequences. The natural product anthramycin, a PBD, was first reported in 1965 (Leimgruber, et al., (1965) J. Am. Chem. Soc., 87:5793-5795; Leimgruber, et al., (1965) J. Am. Chem. Soc., 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham VanDevanter, (1986) Ace. Chem. Res., 19:230-237). Dimeric PBD compounds bearing C2 aryl substituents have been shown to be useful as cytotoxic agents (Hartley et al (2010) Cancer Res. 70(17):6849-6858; Antonow (2010) J. Med. Chem. 53(7):2927-2941; Howard et al (2009) Bioorganic and Med. Chem. Letters 19(22):6463-6466).

PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti cancer properties (US 2010/0203007). Non-limiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/256157; WO 2011/130598).

Non-limiting exemplary PBD dimer components of ADCs are of Formula A:

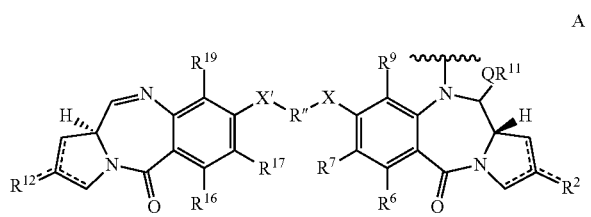

A and salts (e.g., pharmaceutically acceptable salt) and solvates (e.g., pharmaceutically acceptable solvates) thereof, wherein:

the wavy line indicates the covalent attachment site to the linker;

the dotted lines indicate the optional presence of a double bond (the double bond may, e.g., be between C1 and C2 or C2 and C3);

$R^2$ and $R^{12}$ are each independently selected from —H, —OH, =O, =CH$_2$, —CN, —R, —OR, =CH—$R^D$, =C($R^D$)$_2$, —O—SO$_2$—R, —CO$_2$R, —COR, and -halogen, wherein $R^D$ is independently selected from —H, —CO$_2$R, —C(O)R, CHO, CO$_2$H, —R, —OH, —OR, —SH, —SR, —NH$_2$, —NHR, —NRR', —NO$_2$, Me$_3$Sn— and -halogen;

$R^6$, $R^9$, $R^{16}$ and $R^{19}$ are independently selected from —H, —R, —OH, —OR, —SH, —SR, —NH$_2$, —NHR, —NRR', —NO$_2$, Me$_3$Sn— and -halogen;

$R^7$ and $R^{17}$ are independently selected from —H, —R, —OH, —OR, —SH, —SR, —NH$_2$, —NHR, —NRR', —NO$_2$, Me$_3$Sn— and -halogen;

Q is independently selected from —O—, —S— and —N(H)—;

$R^{11}$ is either —H or —R or, in the case where Q is —O—, $R^{11}$ may be —SO$_3$M, wherein M is an alkali metal or alkaline earth metal cation;

R and R' are each independently selected from optionally substituted $C_{1-12}$ alkyl, $C_{3-8}$ heterocyclyl, $C_{3-20}$ heterocycle and $C_{5-20}$ aryl groups, and, if R and $R^1$ are bound to the same nitrogen atom, R and R' may form, together with the nitrogen atom to which they are attached, an optionally substituted 4-, 5-, 6- or 7-membered heterocyclic ring;

R" is a $C_{3-12}$ alkylene group, in which one or more carbon atoms may be replaced by heteroatoms, selected from O, NH and S, and/or aromatic rings that are optionally substituted;

wherein the aromatic rings comprise 5 or 6 carbon atoms and one or two heteroatoms selected from N or NH, and X and X' are independently selected from O, S, and N(H).

Preferably, R and $R^1$ are each independently selected from optionally substituted $C_{1-12}$ alkyl, $C_{3-20}$ heterocyclyl, and $C_{5-20}$ aryl groups, and, if R and $R^1$ are bound to the same nitrogen atom, R and R' may form, together with the nitrogen atom to which they are attached, an optionally substituted 4-, 5-, 6- or 7-membered heterocyclic ring.

Preferably, $R^9$ and $R^{19}$ are —H.

Preferably, $R^6$ and $R^{16}$ are —H.

Preferably, $R^7$ are $R^{17}$ are both —OR$^{74}$ wherein $R^{74}$ is optionally substituted $C_{1-4}$ alkyl.

More preferably, $R^{74}$ is Me. Alternatively, $R^{74}$ is CH$_2$Ph, where Ph is a phenyl group.

Preferably, X is O.

Preferably, $R^{11}$ is H.

Preferably, there is a double bond between $C_2$ and $C_3$ in each monomer unit.

Preferably, $R^2$ and $R^{12}$ are independently selected from H and R. More preferably, $R^2$ and $R^{12}$ are independently R. Even more preferably, $R^2$ and $R^{12}$ are independently optionally substituted $C_{5-20}$ aryl or $C_{5-10}$ aryl or $C_{5-7}$ aryl. Still more preferably, $R^2$ and $R^{12}$ are independently optionally substituted phenyl, thienyl, napthyl, pyridyl, quinolinyl, or isoquinolinyl. Alternatively, $R^2$ and $R^{12}$ are independently selected from =O, =CH$_2$, =CH—$R^D$, and =C($R^D$)$_2$. Preferably, $R^2$ and $R^{12}$ are each =CH$_2$ or $R^2$ and $R^{12}$ are each H. Alternatively, $R^2$ and $R^{12}$ are each =O, or $R^2$ and $R^{12}$ are each =CF$_2$. $R^2$ and/or $R^{12}$ can also independently be =C($R^D$)$_2$. Preferably, $R^2$ and/or $R^{12}$ are independently =CH—$R^D$.

When $R^2$ and/or $R^{12}$ is =CH—$R^D$, each group may independently have either configuration shown below:

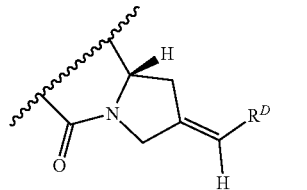
(I)

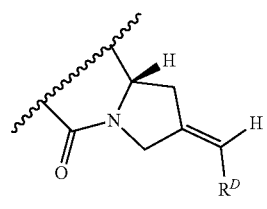
(II)

Preferably, =CH—$R^D$ is in configuration (I).

R" is preferably a $C_3$ alkylene group or a $C_5$ alkylene group.

An exemplary PBD dimer component of an ADC has the structure of Formula A(I):

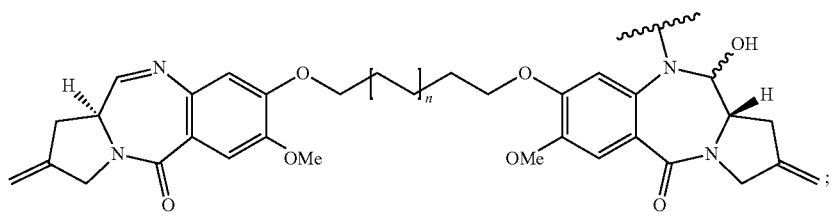
A(I)

wherein n is 0 or 1.

Another exemplary PBD dimer component of an ADC has the structure of Formula A(II):

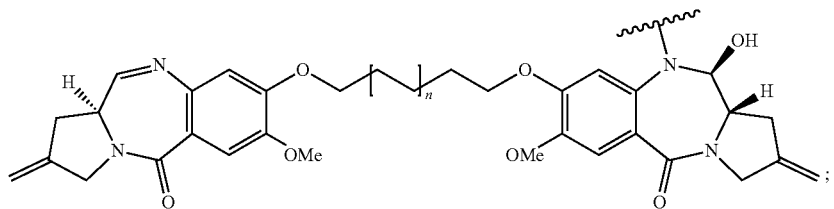
A(II)

wherein n is 0 or 1.

Another exemplary PBD dimer component of an ADC has the structure of Formula A(III):

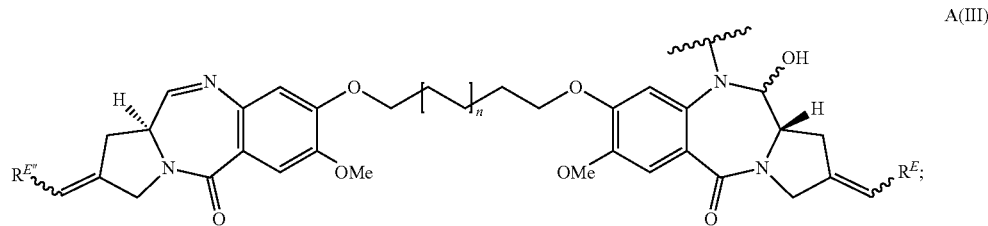

A(III)

wherein $R^E$ and $R^{E''}$ are each independently selected from H or $R^D$,
wherein $R^D$ is defined as above; and
wherein n is 0 or 1.

Preferably, n is 0 or 1. $R^E$ and/or $R^{E''}$ is preferably H. More preferably, $R^E$ and $R^{E''}$ are H. Alternatively, $R^E$ and/or $R^{E''}$ can be $R^D$, wherein $R^D$ is optionally substituted $C_{1-12}$ alkyl. Preferably, $R^E$ and/or $R^{E''}$ is $R^D$, wherein $R^D$ is methyl.

Another exemplary PBD dimer component of an ADC has the structure of Formula A(IV):

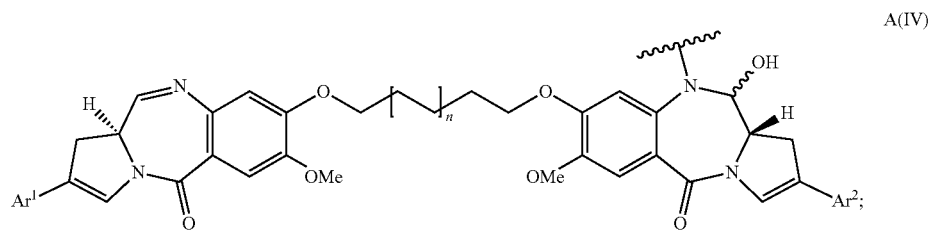

A(IV)

wherein $Ar^1$ and $Ar^2$ are each independently optionally substituted $C_{5-20}$ aryl;
wherein $Ar^1$ and $Ar^2$ may be the same or different; and
wherein n is 0 or 1.

Another exemplary PBD dimer component of an ADC has the structure of Formula A(V):

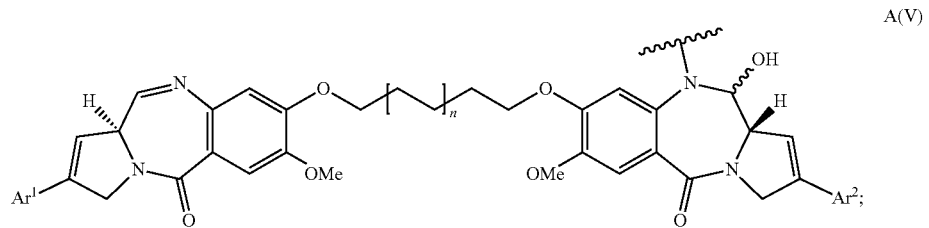

A(V)

wherein $Ar^1$ and $Ar^2$ are each independently optionally substituted $C_{5-20}$ aryl;
wherein $Ar^1$ and $Ar^2$ may be the same or different; and
wherein n is 0 or 1.

Preferably, $Ar^1$ and $Ar^2$ are each independently selected from optionally substituted phenyl, furanyl, thiophenyl and pyridyl. More preferably, $Ar^1$ and $Ar^2$ are each independently optionally substituted phenyl. Alternatively, $Ar^1$ and $Ar^2$ are each independently optionally substituted thien-2-yl or thien-3-yl. Alternatively, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Preferably, the isoquinolinyl is selected from isoquinolin-3-yl and isoquinolin-6-yl.

Further non-limiting exemplary PBD dimer components of ADCs are of Formula B:

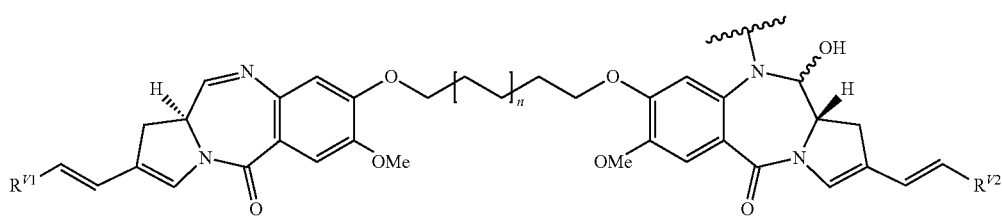

B and salts and solvates thereof, wherein:
the wavy line indicates the covalent attachment site to the linker;
the wavy line connected to the OH indicates the S or R configuration;
$R^{v1}$ and $R^{v2}$ are independently selected from H, methyl, ethyl and phenyl (which phenyl may be optionally substituted with fluoro, particularly in the 4 position) and $C_{5-6}$ heterocyclyl; wherein $R^{v1}$ and $R^{v2}$ may be the same or different; and n is 0 or 1. Preferably, $R^{v1}$ and $R^{v2}$ are independently selected from H, phenyl, and 4-fluorophenyl.

A linker may be attached at one of various sites of the PBD dimer drug moiety, including the N10 imine of the B ring, the C-2 endo/exo position of the C ring, or the tether unit linking the A rings (see structures C(I) and C(II) below).

Non-limiting exemplary PBD dimer components of ADCs include Formulae C(I) and C(II):

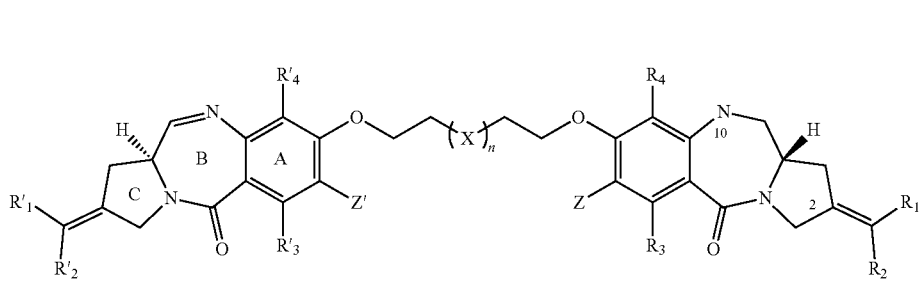

C(I)

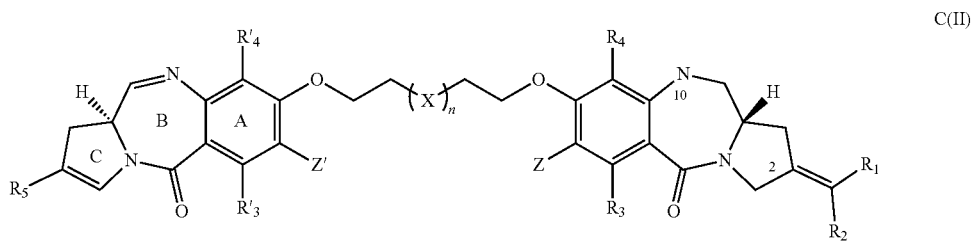

C(II)

wherein Formulae C(I) and C(II) are shown in their N10-C11 imine form. Exemplary PBD drug moieties also include the carbinolamine and protected carbinolamine forms as well, as shown in the table below:

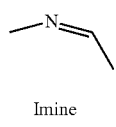

Imine

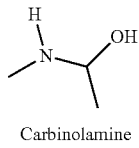

Carbinolamine

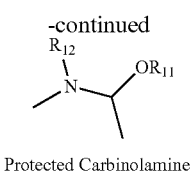

Protected Carbinolamine and wherein:
n is from 1 to 5 if X is $CH_2$;
n is 1 if X is N or O;
Z and Z' are independently selected from OR and $NR_2$, where R is a primary, secondary or tertiary alkyl chain containing 1 to 5 carbon atoms;
$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where alkyl, alkenyl and alkynyl chains preferably comprise up to 5 carbon atoms;
$R_3$ and $R'_3$ are independently selected from H, OR, NHR, and $NR_2$, where R is a primary, secondary or tertiary alkyl chain containing 1 to 5 carbon atoms;
$R_4$ and $R'_4$ are independently selected from H, Me, and OMe;
$R_5$ is selected from $C_1$-$C_8$ alkyl, $C_2$-$C_8$ alkenyl, $C_2$-$C_8$ alkynyl, $C_{5-20}$ aryl (including aryls substituted with halo, nitro, cyano, alkoxy, alkyl and heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB); $R_{12}$ is H, $C_1$-$C_8$ alkyl, or a protecting group; wherein a hydrogen in one of $R_1$, $R'_1$, $R_2$, $R'_2$, $R_5$, or $R_{12}$ or a hydrogen in the —$OCH_2CH_2(X)_nCH_2CH_3O$— spacer between the A rings is replaced with a bond connected to the linker of the ADC.

Exemplary PDB dimer portions of ADC include, but are not limited to (the wavy line indicates the site of covalent attachment to the linker):

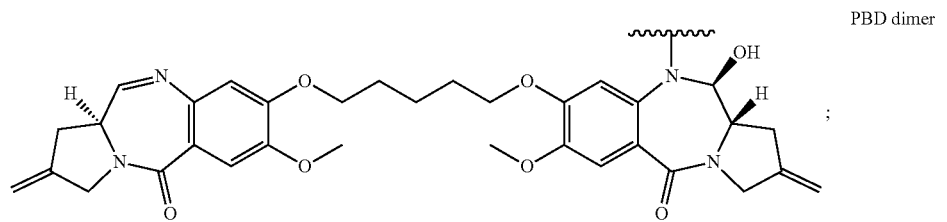

PBD dimer

A further non-limiting exemplary ADC comprising a PBD dimer may be made by conjugating a monomethyl disulfide N10-linked PBD (shown below) to an antibody:

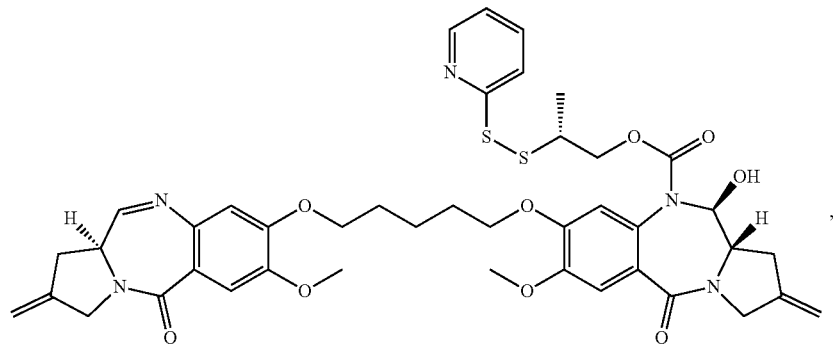

to produce a monomethyl disulfide N10-linked PBD antibody-drug conjugate:

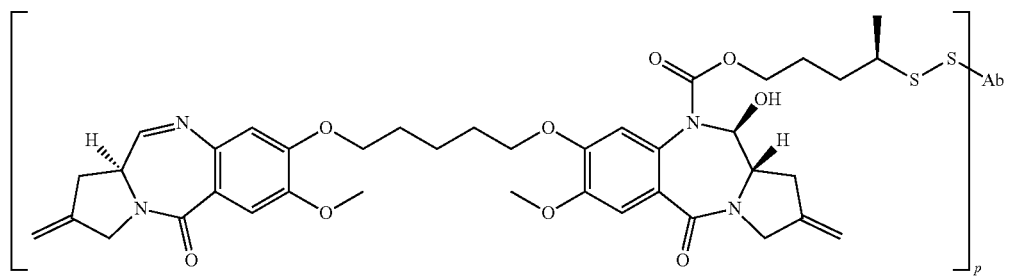

The linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157 and WO 2011/130598.

c. Anthracyclines

In some embodiments, an ADC comprises an anthracycline. Anthracyclines are antibiotic compounds that exhibit cytotoxic activity. While not intending to be bound by any particular theory, studies have indicated that anthracyclines may operate to kill cells by a number of different mechanisms, including:

1) intercalation of the drug molecules into the DNA of the cell thereby inhibiting DNA-dependent nucleic acid synthesis;
2) production by the drug of free radicals which then react with cellular macromolecules to cause damage to the cells, and/or
3) interactions of the drug molecules with the cell membrane (see, e.g., C. Peterson et al., "Transport And Storage Of Anthracycline In Experimental Systems And Human Leukemia" in Anthracycline Antibiotics In Cancer Therapy; N. R. Bachur, "Free Radical Damage" id. at pp. 97-102).

Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in Anthracycline: Current Status And New Developments p 11).

Non-limiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0 328 147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11 (4): 1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev* 17:133; Ripamonti et al (1992) *Brit. J. Cancer* 65:703), including phase II/III trials for hepatocellular carcinoma (Sun et al (2003) *Proceedings of the American Society for Clinical Oncology* 22, Abs 1448; Quintieri (2003) *Proceedings of the American Association of Cancer Research*, 44: 1st Ed, Abs 4649; Pacciarini et al (2006) *Jour. Clin. Oncology* 24: 14116).

A non-limiting exemplary ADC comprising nemorubicin or nemorubicin derivatives is shown in Formula Ia

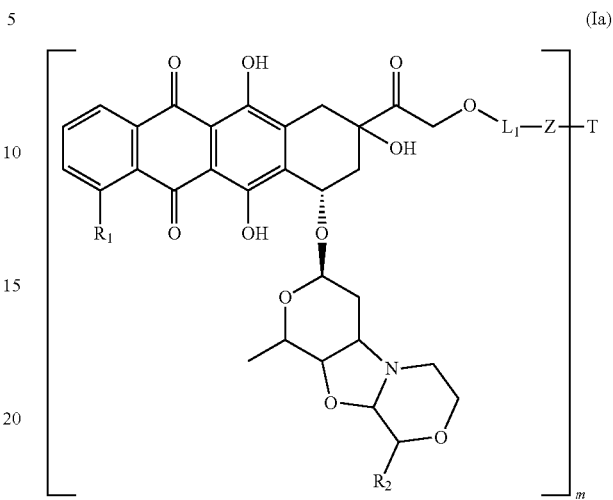

(Ia)

wherein $R_1$ is hydrogen atom, hydroxy or methoxy group and
$R_2$ is a $C_1$-$C_5$ alkoxy group,
or a pharmaceutically acceptable salt thereof;
$R_1$ and $R_2$ may both be methoxy (—OMe).
$L_1$ and Z together are a linker (L) as described herein.
T is an antibody (Ab) as described herein; and
m is 1 to about 20, preferably m is 1 to 10, 1 to 7, 1 to 5, or 1 to 4.

A further non-limiting exemplary ADC comprising nemorubicin or nemorubicin derivatives is shown in Formula Ib:

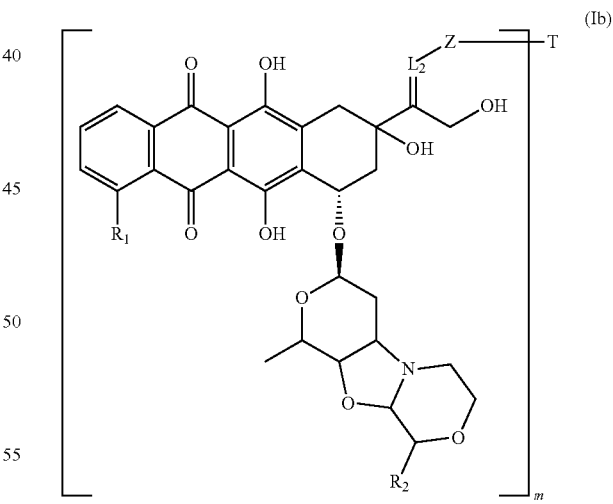

(Ib)

wherein $R_1$ is hydrogen atom, hydroxy or a methoxy group and
$R_2$ is a $C_1$-$C_5$ alkoxy group, or
a pharmaceutically acceptable salt thereof;
$L_2$ and Z together are a linker (L) as described herein;
T is an antibody (Ab) as described herein; and
m is 1 to about 20, preferably, m is 1 to 10, 1 to 7, 1 to 5, or 1 to 4.
$R_1$ and $R_2$ may both be methoxy (—OMe).

The nemorubicin component of a nemorubicin-containing ADC may be PNU-159682.

In such a case, the drug portion of the ADC may have one of the following structures:

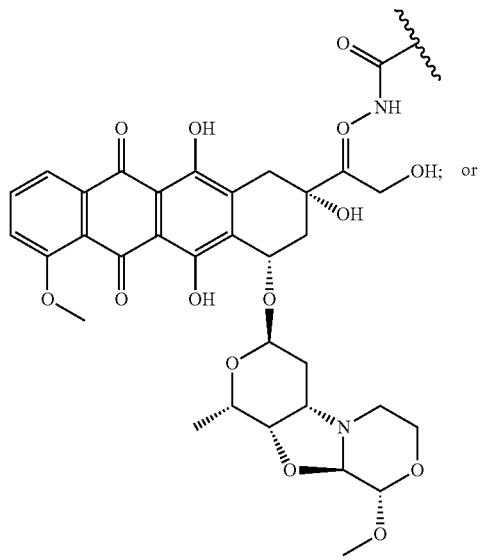

or

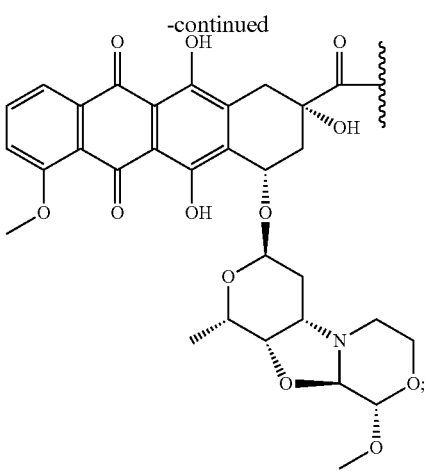

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

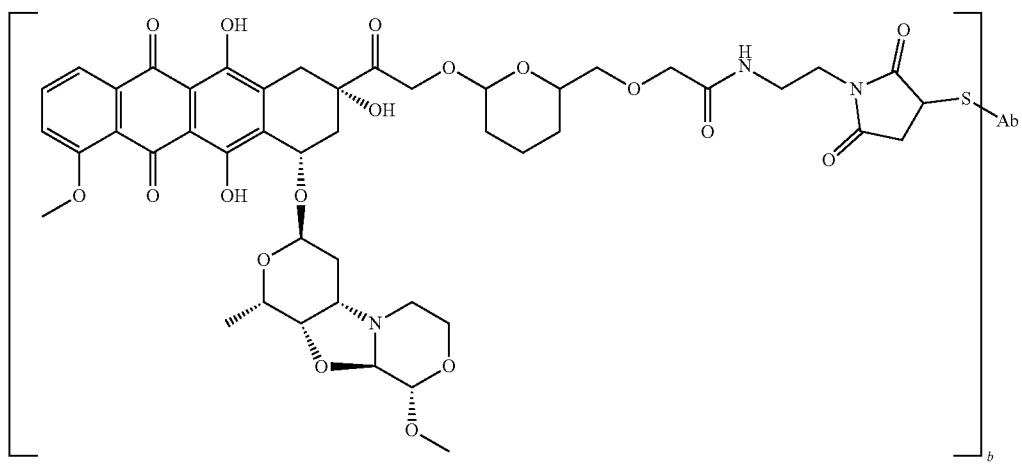

PNU-159682-maleimide acetal Ab
and

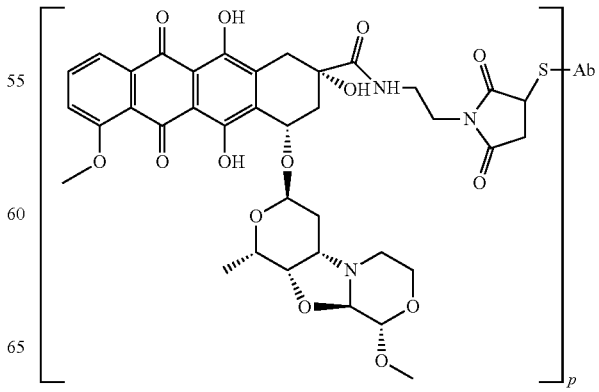

PNU-159682-maleimide-Ab.

The linker of PNU-159682 maleimide acetal-Ab is acid-labile.

(6) Other Drug Moieties

Drug moieties also include geldanamycin (Mandler et al (2000) *J. Nat. Cancer Inst.* 92(19): 1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

An immunoconjugate may comprise a radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. For example, labels such as $Tc^{99}$, $I^{123}$, $Re^{186}$, $Re^{188}$ and $In^{111}$ can be attached via a cysteine residue in the antibody. Yttrium-90 can be attached via a lysine residue of the antibody. The IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

An immunoconjugate may comprise an antibody conjugated to a prodrug-activating enzyme. For example, a prodrug-activating enzyme can convert a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as ß-galactosidase and neuraminidase, which are useful for converting glycosylated prodrugs into free drugs; ß-lactamase, which is useful for converting drugs derivatized with ß-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as ß-galactosidase and neuraminidase, which are useful for converting glycosylated prodrugs into free drugs; ß-lactamase, which is useful for converting drugs derivatized with ß-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

Drug loading is represented by p, the average number of drug moieties per antibody in a molecule of Formula 1. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

In certain embodiments, any of the anti-GP73 antibodies provided herein is useful for detecting the presence of GP73 in a biological sample. The term "detecting" as used herein encompasses quantitative or qualitative detection. A "biological sample" comprises, e.g., a cell or tissue (e.g., biopsy material, including cancerous or potentially cancerous lymphoid tissue, such as lymphocytes, lymphoblasts, monocytes, myelomonocytes, and mixtures thereof).

In one embodiment, an anti-GP73 antibody for use in a method of diagnosis or detection is provided. In a further aspect, a method of detecting the presence of GP73 in a biological sample is provided. In certain embodiments, the method comprises contacting the biological sample with an anti-GP73 antibody as described herein under conditions permissive for binding of the anti-GP73 antibody to GP73, and detecting whether a complex is formed between the anti-GP73 antibody and GP73 in the biological sample. Such method may be an in vitro or in vivo method. In one embodiment, an anti-GP73 antibody is used to select subjects eligible for therapy with an anti-GP73 antibody, e.g. where GP73 is a biomarker for selection of patients. In a further embodiment, the biological sample is a cell or tissue.

In a further embodiment, an anti-GP73 antibody is used in vivo to detect, e.g., by in vivo imaging, a GP73-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl Med.* 44:1271-1281 (2003). In such embodiments, a method is provided for detecting a GP73-positive cancer in a subject, the method comprising administering a labeled anti GP73 antibody to a subject having or suspected of having a GP73-positive cancer, and detecting the labeled anti-GP73 antibody in the subject, wherein detection of the labeled anti-GP73 antibody indicates a GP73-positive cancer in the subject. In certain of such embodiments, the labeled anti GP73 antibody comprises an anti-GP73 antibody conjugated to a positron emitter, such as $^{68}$Ga, $^{18}$F, $^{64}$Cu, $^{86}$Y, $^{76}$Br, $^{89}$Zr, and $^{124}$I.

In further embodiments, a method of diagnosis or detection comprises contacting a first anti GP73 antibody immobilized to a substrate with a biological sample to be tested for the presence of GP73, exposing the substrate to a second anti-GP73 antibody, and detecting whether the second antiGP73 is bound to a complex between the first anti-GP73 antibody and GP73 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-GP73 antibody is any of the antibodies described herein.

Exemplary disorders that may be diagnosed or detected according to any of the above embodiments include, but are not limited to, GP73-positive cancers, such as GP73-positive liver cancer, GP73-positive hepatocellular carcinoma, GP73-positive gastric cancer, GP73-positive esophageal cancer GP73-positive pancreatic cancer, GP73-positive lung cancer, GP73-positive colon cancer, GP73-positive breast cancer, GP73-positive prostate cancer, GP73-positive leukemia, and GP73-positive lymphoma. In some embodiments, a GPC positive cancer is liver cancer. In some embodiments, a GPC-positive cancer is hepatocellular carcinoma. In some embodiments, a GP73-positive cancer is a cancer that receives an anti-GP73 immunohistochemistry (IHC) or in situ hybridization (ISH) score greater than "0," which corresponds to very weak or no staining in >90% of tumor cells. In another embodiment, a GP73-positive cancer expresses GP73 at a 1+, 2+ or 3+ level. In some embodiments, a GP73-positive cancer is a cancer that expresses GP73 according to a reverse-transcriptase PCR (RT-PCR) assay that detects GP73 mRNA. In some embodiments, the RT-PCR is quantitative RT-PCR.

In certain embodiments, labeled anti-GP73 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, ß-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

Pharmaceutical formulations of an anti-GP73 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules. [0329] The formulations to be used for in vivo administration are generally sterile. Sterility may be readily accomplished, e.g., by filtration through sterile filtration membranes.

Any of the antigen-binding molecules, anti-GP73 antibodies or immunoconjugates provided herein may be used in methods, e.g., therapeutic methods.

In one aspect, an anti-GP73 antibody or immunoconjugate provided herein is used in a method of inhibiting proliferation of a GP73-positive cell, the method comprising exposing the cell to the anti-GP73 antibody or immunoconjugate under conditions permissive for binding of the anti-GP73 antibody or immunoconjugate to GP73 on the surface of the cell, thereby inhibiting the proliferation of the cell. In certain embodiments, the method is an in vitro or an in vivo method. In further embodiments, the cell is a granulocyte or myeloblast.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) J. Immunol. Meth. 160:81-88, U.S. Pat. No. 6,602, 677. The assay may be conducted in 96- or 384-well format, making it amenable to automated high-throughput screening (HTS). See Cree et al. (1995) AntiCancer Drugs 6:398-404.

The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-GP73 antibody or immunoconjugate for use as a medicament is provided. In further aspects, an anti-GP73 antibody or immunoconjugate for use in a method of treatment is provided. In certain embodiments, an anti-GP73 antibody or immunoconjugate for use in treating GP73-positive cancer is provided. In certain embodiments, the invention provides an anti-GP73 antibody or immunoconjugate for use in a method of treating an individual having a GP73-positive cancer, the method comprising administering to the individual an effective amount of the anti-GP73 antibody or immunoconjugate. In one such embodiment, the method further comprises administering to the individual an effective amount of at least one additional therapeutic agent, e.g., as described below.

In a further aspect, the invention provides for the use of an anti-GP73 antibody or immunoconjugate in the manufacture or preparation of a medicament. In one embodiment, the medicament is for treatment of GP73-positive cancer. In a further embodiment, the medicament is for use in a method of treating GP73-positive cancer, the method comprising administering to an individual having GP73-positive cancer an effective amount of the medicament. In one such embodiment, the method further comprises administering to the individual an effective amount of at least one additional therapeutic agent, e.g., as described below.

In a further aspect, the invention provides a method for treating GP73-positive cancer. In one embodiment, the method comprises administering to an individual having such GP73-positive cancer an effective amount of an anti-GP73 antibody or immunoconjugate. In one such embodiment, the method further comprises administering to the individual an effective amount of at least one additional therapeutic agent, as described below.

A GP73-positive cancer according to any of the above embodiments may be, e.g., GP73-positive liver cancer, GP73-positive hepatocellular carcinoma, GP73-positive pancreatic cancer, GP73-positive lung cancer, GP73-positive colon cancer, GP73-positive breast cancer, GP73-positive prostate cancer, GP73-positive leukemia, or GP73-positive lymphoma. In some embodiments, a GP73-positive cancer is a cancer that receives an anti-GP73 immunohistochemistry (IHC) or in situ hybridization (ISH) score greater than "O," which corresponds to very weak or no staining in >90% of tumor cells. In another embodiment, a GP73-positive cancer expresses GP73 at a 1+, 2+ or 3+ level.

An "individual" according to any of the above embodiments may be a human.

In a further aspect, the invention provides pharmaceutical formulations comprising any of the anti-GP73 antibodies or immunoconjugate provided herein, e.g., for use in any of the above therapeutic methods. In one embodiment, a pharmaceutical formulation comprises any of the anti-GP73 antibodies or immunoconjugates provided herein and a pharmaceutically acceptable carrier. In another embodiment, a pharmaceutical formulation comprises any of the anti-GP73 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-GP73 antibody.

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1: Monoclonal Antibody Generation

A. GP73 Extracellular Remnant Domain Antibody Detection and Characterization

Monoclonal antibodies against human GP73 were generated using the following procedures by screening two human scFV libraries (Creative Biolabs) with a peptide encompassing the short remnant of human GP73 extracellular domain (rGP73, Seq NO: 1 AA 36 to 55). Four rounds of panning were performed 41 binders were tested by ELISA and six were validated and sequenced. Two complete scFv clones were identified and cloned (i) with human IgG1 heavy chain and human Igk light chain constant regions, G2-2 and G2-1, and (ii) with murine IgG2a heavy chain and human Igk light chain constant regions, denoted mG2-2. The heavy and light chain variable region sequences of antibody G2-2 are shown in SEQ ID NO: 2 and 3, respectively. The heavy and light chain variable region sequences of antibody G2-1 are shown in SEQ ID NO: 10 and 11, respectively. The human heavy chain constant region (IgG1) is shown in SEQ ID NO: 26, the human kappa light chain sequence is shown in SEQ ID NO: 27. The murine heavy chain constant region (IgG2a) is shown in SEQ ID NO: 28.

B. GP73 Soluble Fragment Antibody Detection and Characterization

Monoclonal antibodies against human GP73 were generated using the following procedures by immunizing 2 Balb/c mice with a peptide comprising AA 347-366 of human GP73 (SEQ ID NO 1). Following fusion 6 hybridomas expressed antibodies that bound peptide 347-366. Three antibodies were sequenced and kept in culture for antibody production.

Positive clones were expanded and re-screened for binding to human GP73, Hep3B cells, HepG2 cells and HuH 7 cells by ELISA and FACS. One antibody was selected and purified, G2-4. The heavy and light chain variable region sequences of antibody G2-4 are shown in SEQ ID NOs: 18 and 19, respectively.

For larger scale antibody production, antibodies were produced in CHO and in 293HEK cells. Vectors coding for VL and VH were transfected into CHO cells and into 293HEK cells and IgG was purified from cell culture media by protein A affinity chromatography.

Example 2: Immunofluorescence Analysis

Alexander cells were grown on 4 chamber slides, fixed with 4% paraformaldehyde, treated with 0.2% Saponin and blocked with 10% bovine serum albumin. Cells were incubated for one hour with goat anti-GP73 (santa cruz sc-48010) and mG2-2 and washed. Bound antibodies were stained with anti goat Alexa Fluor 488 (abcam ab150129) and anti mouse Alexa Fluor 647 (abcam ab150115). Nuclei were treated with DAPI.

Example 3: Immunohistochemistry Analysis on Various Tumors

Paraffin embedded tissues of normal liver, hepatitis liver, hepatocellular carcinoma (HCC), endometrium carcinoma, ovarian carcinoma, melanoma, small cell lung cancer and gastric cancer were stained with murine G2-2 (mG2-2) or mouse anti GOLPH (M06A Sigma) followed by secondary staining with an anti-mouse IgG. Nuclei were stained with hematoxylin (blue), cytoplasma was stained with hemalum-eosin.

Example 4: Flow Cytometry of Various Cell Lines with the Anti-GOLPH Antibody G2-2, G2-1 and Controls Different human and murine cell lines e.g. HuH7, JHH4, HEK293, HEK293-GP73-myc and Ramos were tested by Flow cytometry analysis for expression of GP73 on their cell surface and binding of G2-2, G2-1 and G2-4. Cells were cultured, pelleted, fixed with PFA4% and incubated with mG2-2, mG2-1, G2-4, anti myc or anti CD19 IgG (BD HIB19), washed and stained with secondary fluorescent anti mouse antibody (Alexa Fluor 488).

Example 5: Competition and pH Dependent Peptide ELISA

ELISA was carried out in 96 well plates coated overnight with biotinylated peptide and blocked with 2% gelatine. Horse radish peroxidase labeled antibodies G2-1 (G2-1-HRP) or G2-2 (G2-2-HRP) were applied and incubated for 1.5 hours. For competition testing non labeled G2-1 or G2-2 was added at high concentration. For pH dependent binding the antibodies were applied in phosphate buffer pH 4.4, 5.4, 6.4 or 7.4. After extensive washing a chromogenic substrate (TMB Amersham) was added to detect peroxidase. The reaction was stopped and absorbance was read at 450 nm.

Example 6: Internalization of G2-2

The cell lines DU145 (prostate cancer) and Hep55.1C (hepatocellular carcinoma) were tested for their ability to internalize the antibodies G2-2 and G2-1. Cells were incubated with 10 ug/ml of G2-2 or G2-1 for one hour at 4° C. in PBS. Unbound G2-2 was washed away and cells were transferred to tissue culture medium with 10% FCS and then either warmed to 37° C. to allow internalization or maintained at 4° C. The internalization process was stopped after 15, 30, 60 or 120 minutes by transferring the cells into ice-cold buffer with 0.1% sodium acid. Cells were stained with APC-conjugated goat anti-human Fab (Jackson Immuno) and analyzed by FACS. The residual levels of cell surface G2-2 was calculated based on the mean fluorescence intensity (MFI). After 15 minutes cell surface detection of G2-2 and G2-1 was reduced to 30% in HuH7 and to less than 10% in DU145.

To demonstrate that G2-2 and G2-1 bind to GP73 and are internalized under conditions, where C-terminal GP73 binding antibodies e.g. G2-4 are inhibited in binding, antibodies were labeled with pHrodo Green STP Ester (Thermofisher). This dye is nonfluorescent at neutral pH but exhibits increasing fluorescence as the ph becomes more acidic e.g. in endosomes. Labeled antibodies were purified by size exclusion (40K MWCO). A non binding Isotype Antibody that was not labeled with pHrodo® Green STP Ester (Iso.) was used as control for background fluorescence. 10 ug/ml of each antibody was pre-incubated over night at 4° C. with either fresh culture media or conditioned media. As conditioned media served either supernatant from HEK 293 or HEK 293 GP73-myc cells cultured for 72 hours, that was dialyzed (10 k MWCO) against 1 L fresh media each. To confirm the presence of secreted soluble GP73 after dialysis supernatants were analysed by Western Blot using an anti-myc antibody. 300 ul/well of each pre-incubated antibody was given to 0.6×10⁶ HuH7 cells growing in 24 well plates for 24 h at 37° C. and 5% $CO_2$. Cells were washed and analysed by FACS.

Example 7: Furin Cleavage Analysis of GP73 Depending on G2-2 or G2-1 Binding

Testing of Furin cleavage exploits the fact that antibodies G2-1 and G2-2 bind GP73 N-terminal of or at the furin cleavage site 56R whereas recombinant GP73 with C-terminal HIS tag (GP73-HIS) is detected by anti HIS antibody at the C-terminus of GP73. Plate bound anti human IgG can capture G2-1 or G2-2, which binds GP73-HIS. If furin cleavage occurs in a setting where G2-1 or G2-2 have already bound to GP73-HIS, only N-terminal part of GP73 will reside at the G2 antibodies. In contrast, if furin cleavage is hindered by G2 antibodies, GP73-HIS can be detected by an anti HIS antibody.

Furin cleavage was carried out in 1.5 ml tubes. To test if G2 antibodies can hinder furin cleavage recombinant GOLPH-HIS protein (Biolegend) and G2-2 or G2-1 was incubated for 2 hours in 100 mM HEPES and 1 mM CaCl2 buffer pH 7.5 to allow antibody binding to GP73. Each reaction was supplemented with either 3 U, 1.5 U, 0.75 U, 0.375 U or 0 U of furin (New England Biolabs) for cleavage during 2 hours at 30° C. To test the maximum of furin cleavage in this assay setting recombinant GOLPH-HIS protein (Biolegend) and either 3 U, 1.5 U, 0.75 U, 0.375 U or 0 U of furin were incubated for 2 hours in 100 mM HEPES and 1 mM CaCl2 buffer pH 7.5 to allow furin cleavage. Each reaction was supplemented with either G2-2 or G2-1 during 2 hours for binding at 30° C.

From each reaction 2×100 ul were transferred to wells of a 96 well plate that had been coated over night with anti human IgG and was blocked with 1% gelatine in PBS. After one hour incubation at room temperature the plate was washed, incubated with anti HIS-hrp antibody for one hour, washed again, incubated with a chromogenic substrate (TMB Amersham) to detect peroxidase, stopped and read at 450 nm. The results demonstrate a reduction in furin cleavage due to binding of G2-1 and G2-2.

Example 8: Anti-GP73 Antibodies and their Effect on Cell Viability of Different Cell Lines Cells from the cell lines HuH7 (human hepatocellular carcinoma), 4T1 (murin breast carcinoma) and CaCo2 (human colorectal carcinoma) were cultured under standard conditions in Dulbecco's modified Eagle Medium (DMEM) supplemented with 10% fetal calf serum (FCS) at 37° C. with 5% $CO_2$. HuH7 cells were transferred to 96 well plates and treated with G2-2, G2-2 plus Cetuximab, mG2-2, mG2-2 plus Cetuximab, Cetuximab or control antibody each in increasing concentrations from 0.125 mg/ml to 2 mg/ml. Each test was done in triplicate. After 72 hours each well was supplemented with PrestoBlue reagent (ThermoFischer) and incubated for 20 min at 37° C. Fluorescence was read at 615 nm to quantify cell viability. PrestoBlue reagent is reduced by metabolically active cells. Cell viability was reduced depending on antibody concentration. This effect was independent of the Fc part i.e. human IgG1 in G2-2 or murin IgG2a in mG2-2.

To test the effect of G2-1 on different cell lines, HuH7, 4T1 and CaCo2 cells were transferred to 96 well plates. Each well was treated either with G2-1 2 mg/ml, G2-1 1 mg/ml plus Cetuximab 1 mg/ml, Cetuximab 2 mg/ml, Bevacizumab 2 mg/ml or Bevacizumab 1 mg/ml plus Cetuximab 1 mg/ml. Each test was done in triplicate. Cell viability was quantified after 72 hours using PrestoBlue reagent and measuring the fluorescence at 615 nm. And additive effect of G2-1 plus Cetuximab was found in HuH7 cells.

Example 9: Anti-GP73 Antibody-Drug Conjugates (ADCs)

Anti-GP73 antibody-drug conjugates (ADCs) were produced by conjugating of partially reduced G2-2 (human IgG1/kappa) and mG2-2 (murin IgG2/kappa) to the drug-linker moiety maleimide acetal PNU-159682 or maytansinoid (MMAF). As previously described, e.g. in Junutula et al. (2008) Nat. Biotechnol. 26:925-932 and US 2011/ 0301334 the antibody is combined with the drug-linker moiety to allow conjugation of the drug-linker moiety to free cysteine residues of the antibody. After several hours, the ADCs were purified. The drug load (average number of drug moieties per antibody) for each ADC was determined and was 2 for the PNU and 2 the MMAF conjugates.

Example 10: Efficacy of G2-2-ADC in HuH7 Cells

An antibody drug conjugate consisting of MMAF attached by a malameide exchange linker to G2-2 was added to the cell culture medium of HUH7 cells in different concentrations. Medium was changed after one hour. Cell viability was analyzed after 98 hours using PrestoBlue reagent (ThermoFischer). The black curve shows G2-2-Mal-VC-PAB-MMAF with an IC50 of 6.34 nM as determined by antibody component. The red curve shows G2-2-Mal-VC-PAB-MMAF with an IC50 of 0.124 nM as determined by drug component. The blue curve shows toxicity of MMAF as determined by drug component IC50 277 nM. The toxicity of MMAF was enhanced by the Factor 2234 due to the attachment to the G2-2 antibody as shown in FIG. 10.

Example 11: Efficacy of G2-2-ADC in HuH7 Cell Line Xenograft Model

The efficacy of the anti-GP73 ADCs was investigated using a human HuH7 xenograft model. Female Balb/c nude mice (Crown Bio Laboratories; Beijing, China) were each inoculated subcutaneously in the flank area with ten million cells of HuH7. When the xenograft tumors reached an average tumor volume of 183 $mm^3$ (denoted Day 0), animals were randomized into groups of 12 mice each and received an intravenous injection of 2 mg/kg ADC at day 0 and of 1 mg/kg ADC at day 7 or control substances. Tumors and body weights of mice were measured every other day throughout the study. Mice were promptly euthanized when body weight loss was >20% of their starting weight. All animals were euthanized when their tumor reached 2000 $mm^3$. Expression of GP73 on the surface of the HuH7 cells and HuH7 tumors isolated from xenograft mice was confirmed by FACS and IHC.

As shown in FIG. 15 substantial tumor growth inhibition was achieved with G2-2-PNU. The difference in the cumulative survival was statistically significant between vehicle group and ADC group as shown in FIG. 12. Data were analyzed using SPSS.

Although the foregoing invention has been described in some detail by way of illustration and example for purpose of clarity of understanding, the descriptions and examples should not be construed as limiting the scope of invention. The disclosures of all patent and scientific literature cited herein are expressly incorporated in their entirety of reference.

Example 12: Optimized GP73 Antibodies

Antibodies G2-2 and G2-1 were optimized for expression in mammalian cells by directed mutagenesis derived from computational comparison to antibodies found in publicly available databases (e.g. IMGT/mAb-DB). The respective adjustments affected the framework of the variable regions and the constant region of the murine heavy chain. Thereby, the CDRs remained untouched. These optimized sequences were named G2-2opti (IgG1) and G2-1opti (IgG1). For certain experiments G2-2opti (IgG1) was converted to G2-2opti (IgG2a), a chimeric human/murine version with a murine CH2 and CH2. In the functional assays these constructs performed either the same or better than G2-2 or G2-1, respectively.

Example 13: Differential Binding of Antibody 8A10 from Patent CN105734059A and G2-2 on GP73 Protein and Peptide Antibody 8A10 from patent CN105734059A was generated to test for differential binding of 8A10 on GP73 as compared to G2-2 on GP73. Specifically, experiments were conducted to test whether 8A10 recognizes the same epitope as an antibody of the invention.

The published nucleotide sequence of the antibody 8A10 from patent CN105734059A contained a point mutation in the constant region of the kappa light chain (Y193C). For sufficient expression the sequence was fitted to the canonical murine kappa sequence by back mutation to Y193. The otherwise unaltered nucleotide sequence of 8A10 was synthesized by GenScript NJ, USA. A secretion signal was added at the N-terminus and the heavy chain supplemented with an appropriate sequence of a murine IgG2a. Each chain was cloned into a mammalian expression vector for transient transfection of HEK293 cells. The antibody was extracted from the cell supernatant by immobilized metal affinity chromatography (IMAC) and tested for integrity by Western Blotting and ELISA.

293HEK cells were either transfected with cDNA containing full length GP73 AA 1-401 C-terminal tagged with 10×HIS-Tag or with a GP73 ΔN variant containing AA 36 to 401 with a R52A mutation, resulting in a non-cleavable variant, C-terminal tagged with 10×HIS-Tag (GP73-His AVRR). In both constructs a secretion signal was added in frame to the N-terminus. The supernatant of the full length GP73 expressing cells contains sGP73-10×His, encompassing GP73 AA56 to 401 (sGP73; SEQ ID NO: 40), that has been proteolytically cleaved by furin or another protease at AA 55. The supernatant of the GP73 ΔN variant contains GP73-10×His AVRR, encompassing GP73 AA36 to 401 (GP73 AVRR; SEQ ID NO: 41) as shown in FIG. 20. Only the latter of the two constructs contains the rGP73 epitope. Both proteins were isolated by IMAC.

ELISA was carried out in 96 well plates coated overnight with sGP73 or GP73 AVRR and blocked with 2% gelatine. Antibodies 8A10, G2-2opti (IgG2a) or isotype control antibody were applied, incubated for 1.5 hours and washed away. A secondary Horse radish peroxidase labeled anti mouse antibody was added for 1 hour and after extensive washing a chromogenic substrate (TMB Amersham) was applied to detect peroxidase. The reaction was stopped and absorbance was read at 450 nm and shown in FIG. 21. The results demonstrate that 8A10 binds only to sGP73 but not to GP73 AVRR, whereas G2-2opti (IgG2a) binds to GP73 AVRR but not to sGP73, suggesting that the recognized epitopes do not overlap.

ELISA was carried out in 96 well plates coated overnight with the biotinylated peptide gp73 AA 36-55 or an unrelated peptide and blocked with 2% gelatine. Antibodies 8A10, G2-2opti (IgG2a) or isotype control antibody (IgG2a) were applied, incubated for 1.5 hours and then washed away. A secondary horse radish peroxidase labeled anti mouse antibody was added for 1 hour and after extensive washing a chromogenic substrate (TMB Amersham) was applied to detect peroxidase. The reaction was stopped and absorbance was read at 450 nm and shown in FIG. 22. The results demonstrate that 8A10 does not bind to rGP73, confirming that the recognized epitopes of 8A10 and G2-2opti (IgG2a) do not overlap.

Example 14: Furin Blockage Experiment in HEK293-GP73-his Cells

HEK293 GP73-His full length cells were seeded in 96 well plates 1500 cells per well and cultured overnight. Next day, medium was changed and cells were treated with Bevacizumab 31.3 ug/ml, Bevacizumab 62.5 ug/ml, G2-2opti(IgG1) 31.3 ug/ml or G2-2opti (IgG1) 62.5 ug/ml. To examine furin cleavage inhibition the respective antibody concentrations were chosen in a range that had no impact on cell proliferation. After 96 hours the supernatants were collected for measurement of sGP73 exploiting the Up-converting Phosphor Technology (UCP) and the remaining cell layer was used in a proliferation assay with PrestoBlue reagent (Thermofisher) described in Example 8. Here, G2-2opti (IgG1) decreases sGP73 secretion into supernatant by HEK293 GP73-His full length cells, whereas Bevacizumab, the isotype control has no influence on sGP73 levels in the supernatant.

For sGP73 detection each supernatant was diluted 1:1 in Hotgen dilution buffer containing an anti GP73 UCP labelled antibody. 0.1 ml thereof was loaded onto a Hotgen GP73 test cassette containing a mouse anti GP73 antibody coated nitrocellulose membrane (C line) and incubated for a chromatographic process during 15 minutes thereby reaching the membrane section coated with goat anti mouse labelled antibody (T line). GP73 concentrations were deduced from differences of light emission at the C and T line measured by inserting the test cassette into the Hotgen Up-converting Phosphor Technology (UCP) Analyser.

Example 15: Effects of the Antibody G2-2Opti (IgG1) and G2-2Opti-EED (IgG1) on Cell Viability of Different Cell Lines The optimized antibody G2-2opti (IgG1) and an antibody variant thereof, G2-2opti-EED (IgG1), the latter carrying an endosomal escape sequence (EED), were tested on human and murine cancer cell lines for efficacy. Human cancer cells HCT 116 p53 wt, HCT 116 p53−/−, SW 480 K-Ras G12V mutated, Caco2 (all colorectal cancer cell lines), SKOV3 (ovarian cancer), HUH7 (human hepatocellular carcinoma cell line), Hepa1-6 (murine hepatocellular carcinoma cell line), DU145, PC3 (human prostate cancer cell lines) and H1975 (lung cancer cell line harboring EGFR mutations T790M and L858R) were seeded in 96 well plates 1500 cells per well and cultured in DMEM over night. Next day medium was changed and cells were treated with 1 mg/ml of G2-2opti (IgG1) or G2-2opti-EED (IgG1) or Cetuximab or Bevacizumab or PBS. After 96 hours cell viability was quantified using PrestoBlue reagent (Thermofisher) as described in Example 8. Results of PBS treated cells served as 100% viability level (see FIG. 23).

The invention claimed is:

1. An antibody or antigen-binding fragment thereof, wherein the antibody comprises a variable heavy (VH) chain comprising CDR1 as defined in SEQ ID NO: 4, CDR2 as defined in SEQ ID NO: 5 and CDR3 as defined in SEQ ID NO: 6 and a variable light (VL) chain comprising CDR1 as defined in SEQ ID NO: 7, CDR2 as defined in SEQ ID NO: 8 and CDR3 as defined in SEQ ID NO: 9.

2. The antibody, or antigen-binding fragment thereof, of claim 1, wherein the antibody
comprises a variable heavy (VH) chain sequence comprising the amino acid sequence of SEQ ID NO: 2 or a sequence having 90% sequence identity thereto and a variable light (VL) chain sequence comprising the amino acid sequence of SEQ ID NO: 3 or a sequence having 90% sequence identity thereto;
or a variable heavy (VH) chain sequence comprising the amino acid sequence of SEQ ID NO: 35 or a sequence having 90% sequence identity thereto; and a variable light (VL) chain sequence comprising the amino acid sequence of SEQ ID NO: 36 or a sequence having 90% sequence identity thereto.

3. An antibody or antigen-binding fragment thereof, wherein the antibody comprises a variable heavy (VH) chain comprising CDR1 as defined in SEQ ID NO: 12, CDR2 as defined in SEQ ID NO: 13 and CDR3 as defined in SEQ ID NO: 14 and a variable light (VL) chain sequence comprising CDR1 as defined in SEQ ID NO: 15, CDR2 as defined in SEQ ID NO: 16 and CDR3 as defined in SEQ ID NO: 17.

4. The antibody or antigen-binding fragment thereof, of claim 3, wherein the antibody
comprises a variable heavy (VH) chain sequence comprising the amino acid sequence of SEQ ID NO: 10 or a sequence having 90% sequence identity thereto and a variable light (VL) chain sequence comprising the amino acid sequence of SEQ ID NO: 11 or a sequence having 90% sequence identity thereto; or
a variable heavy (VH) chain sequence comprising the amino acid sequence of SEQ ID NO: 37 or a sequence having 90% sequence identity thereto and a variable light (VL) chain sequence comprising the amino acid sequence of SEQ ID NO: 38 or a sequence having 90% sequence identity thereto.

5. The antibody or antigen-binding fragment thereof, of claim 1, wherein the antigen-binding fragment is a Fab fragment, a F(ab')2 fragment or a Fv fragment.

6. A polynucleotide that encodes the antibody or antigen-binding fragment thereof of claim 1.

7. A host cell comprising the polynucleotide of claim 6.

8. A method for producing an antibody comprising culturing the host cell of claim 7.

9. A method for producing an antibody that specifically binds to a polypeptide or to an antigenic portion thereof, comprising administering to a subject a polypeptide selected from (a) a polypeptide consisting of SSRSVDLQTRIMELEGRVRR SEQ ID NO: 30;
(b) a polypeptide consisting of SSRSVELQTRIVELEGRVRR SEQ ID NO: 31; and
(c) a polypeptide consisting of SSRSVDLQTRIVELEGRVRR SEQ ID NO: 32.

10. An immunoconjugate comprising the antibody of claim 1 or 3 and a cytotoxic agent or a prodrug of a cytotoxic agent.

11. The immunoconjugate of claim 10 having the formula Ab(-L-D)p, wherein:
a) Ab is the antibody of any of the preceding embodiments;
b) L is a linker;
c) D is a cytotoxic agent; and
d) p ranges from 1-8.

12. The immunoconjugate of claim 10, wherein the cytotoxic agent is selected from a maytansinoid, a calicheamicin, a pyrrolobenzodiazepine and a nemorubicin derivative.

13. The immunoconjugate of claim 11, wherein D is a pyrrolobenzodiazepine of Formula A:

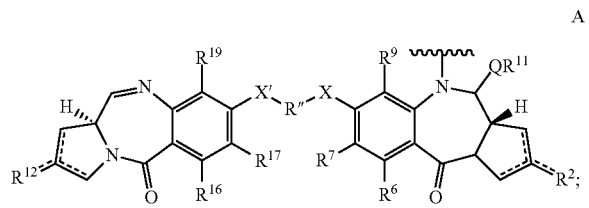

A and a pharmaceutically acceptable salt and solvate thereof, wherein:
the wavy line indicates the covalent attachment site to the linker;
the dotted lines indicate the optional presence of a double bond (the double bond may, e.g., be between C1 and C2 or C2 and C3);
$R^2$ and $R^{12}$ are each independently selected from —H, —OH, =O, =CH$_2$, —CN, —R, —OR, =CH—R$^\circ$, =C(R$^\circ$)2, —O—SO$_2$—R, —CO$_2$R, —COR, and -halogen,
wherein R$^\circ$ is independently selected from —H, —CO$_2$R, —C(O)R, CHO, CO$_2$H, —R, —OH, —OR, —SH, —SR, —NH$_2$, —NHR, —NRR', —NO$_2$, Me$_3$Sn— and -halogen;
$R^6$, $R^9$, $R^{16}$ and $R^{19}$ are independently selected from —H, —R, —OH, —OR, —SH, —SR, —NH$_2$, —NHR, —NRR', —NO$_2$, Me$_3$Sn— and -halogen;
$R^7$ and $R^{17}$ are independently selected from —H, —R, —OH, —OR, —SH, —SR, —NH$_2$, —NHR, —NRR', —NO$_2$, Me$_3$Sn— and -halogen;

Q is independently selected from —O—, —S— and —N(H)—;

$R^{11}$ is either —H or —R or, in the case where Q is —O—, $R^H$ may be —SO$_3$M, wherein M is an alkali metal or alkaline earth metal cation;

R and R' are each independently selected from optionally substituted $C_{1-12}$ alkyl, $C_{3-8}$ heterocyclyl, $C_{3-20}$ heterocycle and $C_{5-20}$ aryl groups, and, if R and R' are bound to the same nitrogen atom, R and R' may form, together with the nitrogen atom to which they are attached, an optionally substituted 4-, 5-, 6- or 7-membered heterocyclic ring;

R" is a $C_{3-12}$ alkylene group, in which one or more carbon atoms may be replaced by heteroatoms, selected from O, NH and S, and/or aromatic rings that are optionally substituted;

wherein the aromatic rings comprise 5 or 6 carbon atoms and one or two heteroatoms selected from N or NH, and X and X' are independently selected from O, S, and N(H).

14. The immunoconjugate of claim 13 wherein D has the structure:

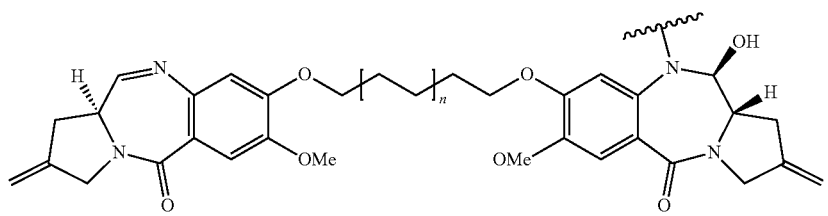

wherein n is 0 or 1.

and

15. The immunoconjugate of claim 11, wherein D is a nemorubicin derivative.

16. The immunoconjugate of claim 15, wherein D has a structure selected from:

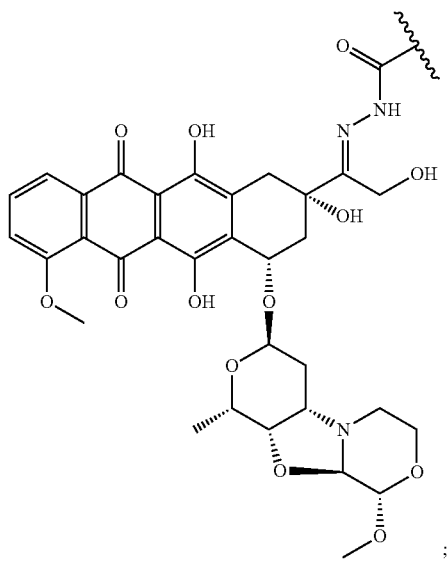 [SMILES: *C(=O)N/N=C(\CO)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

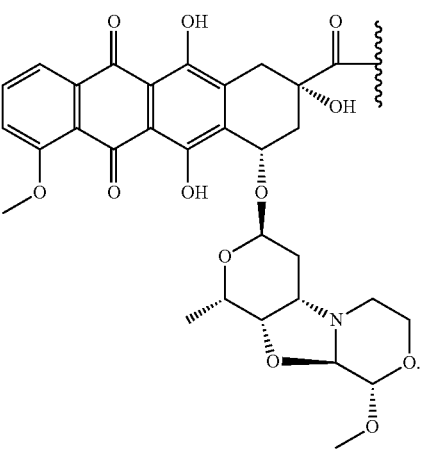 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

;

17. The immunoconjugate of claim 11, wherein the linker is cleavable by a protease, is acid-labile and/or comprises hydrazone.

18. The immunoconjugate of claim 11 having a formula selected from:

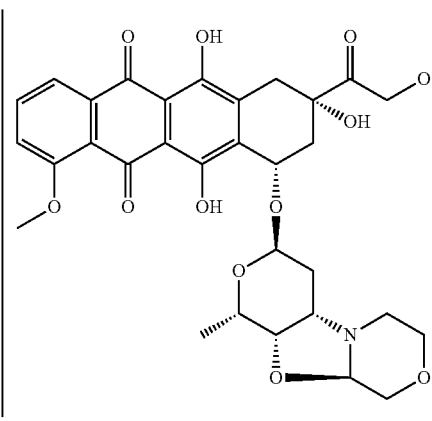

and

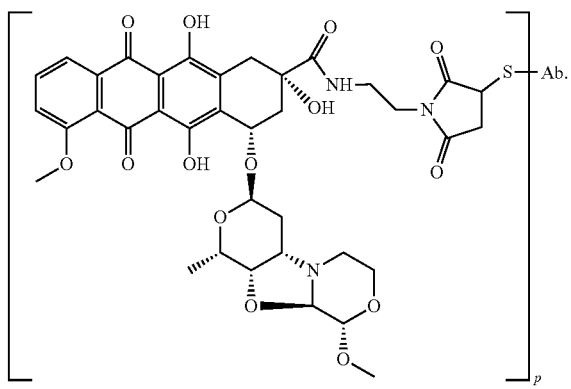

19. The immunoconjugate of claim 11, wherein p ranges from 2-5.

20. An immunoconjugate comprising the antibody of claim 1 and a functional agent, wherein the functional agent is an endosomal escape domain (EED) peptide.

21. The immunoconjugate of claim 20 having the formula Ab(-EEDL-EED peptide), wherein Ab is the antibody of claim 1 and EEDL is an EED linker.

22. The immunoconjugate of 21, wherein the EED peptide is a Dengue Virus EED peptide comprising the amino acid sequence of SEQ ID NO: 42 and the EED linker comprises the amino acid sequence of SEQ ID NO: 43.

23. A pharmaceutical composition comprising the immunoconjugate of claim 10 and a pharmaceutically acceptable carrier.

24. The pharmaceutical composition of claim 23, comprising a further therapeutic agent.

25. A pharmaceutical composition comprising the antibody or antigen-binding fragment thereof, of claim 1 and a pharmaceutically acceptable carrier.

26. The pharmaceutical composition of claim 25, comprising a further therapeutic agent.

27. A method of treating a subject having a GP73-positive cancer, the method comprising administering to the subject an effective amount of the antibody or antigen-binding fragment thereof, of claim 1, the immunoconjugate of claim 10 or the pharmaceutical composition of claim 23.

28. The method of claim 27, wherein the GP73-positive cancer is liver cancer.

29. The method of claim 27 further comprising administering an additional therapeutic agent to the individual.

30. The method of claim 27, wherein administering is intravenous, intraperitoneal, intramuscular, intrasternal, intratumoral, intravesical, intrauterine, intraarticular, intranasal, subcutaneous, topical, as clyster, or as gastric lavage.

31. A method of inhibiting proliferation of a GP73-positive cell, the method comprising exposing the cell to the antibody or antigen-binding fragment thereof, of claim 1 or the immunoconjugate of claim 10 under conditions permissive for binding of the antibody or antigen-binding fragment thereof, or immunoconjugate to GP73 on the surface of the cell, thereby inhibiting proliferation of the cell.

32. The method of embodiment 31, wherein the cell is a liver cancer cell.

33. A method of detecting human GP73 in a biological sample comprising contacting the biological sample with the antibody or antigen-binding fragment thereof, of claim 1 under conditions permissive for binding of the antibody or antigen-binding fragment thereof to a naturally occurring human GP73, and detecting whether a complex is formed between the antibody or antigen-binding fragment thereof and a naturally occurring human GP73 in the biological sample.

34. The method of claim 33, wherein the detecting comprises immunohistochemistry, immunofluorescence imaging, enzyme-linked immunosorbent assay (ELISA), and fluorescence-activated cell sorting (FACS), Western Blot, immunoprecipitation, or radiographic imaging.

35. A method for treating a subject, comprising determining the level, in a sample from the subject, of specific binding of the antibody or antigen-binding fragment thereof of claim 1 with a GP73 polypeptide or with an antigenic portion thereof, wherein detecting an increased level of the specific binding relative to a control sample identifies the subject as having cancer and administering an effective amount of the antibody or antigen-binding fragment thereof of claim 1, the immunoconjugate of claim 10, or the pharmaceutical composition of claim 23 to the subject.

36. The method of claim 35, wherein the cancer is selected from the group consisting of liver cancer, ovarian cancer, endometrium carcinoma, malignant melanoma, prostate cancer, gastric cancer, colorectal carcinoma, lung cancer and leukemia.

37. A composition comprising the antibody or antigen-binding fragment thereof, of claim 1 and an EGFR antibody or small molecules inhibiting EGFR signaling.

38. A method of treating a subject having cancer associated with abnormal expression of GP73, comprising administering to the subject the antibody or antigen-binding fragment thereof, of claim 1, the immunoconjugate of claim 10 or the pharmaceutical composition of claim 23.

39. The method according to claim 38, wherein the cancer is selected from the group consisting of liver cancer, ovarian cancer, endometrium carcinoma, melanoma, prostate cancer, colorectal carcinoma, lung cancer, leukemia and breast cancer.

40. The antibody or antigen-binding fragment thereof of claim 1, the immunoconjugate of claim 10 or the pharmaceutical composition of claim 23 that reduces the level of circulating, soluble GP73 (sGP73) in the plasma.

41. A method for treating a GP73-expressing cancer in a subject, comprising administering an effective amount of the antibody or antigen-binding fragment thereof of claim 1, the immunoconjugate of claim 10, or the pharmaceutical composition of claim 23 to the subject, monitoring the response to treatment of the subject and measuring the level of circulating sGP73 in the plasma at one or more time points before and at one or more time points after treatment of the subject.

42. The method according to claim 41, wherein detecting a reduced level of circulating sGP73 at a time point after treatment relative to a time point before treatment in the plasma of the subject identifies the subject as being responsive to the treatment.

43. The antibody or antigen-binding fragment of claim 1, wherein the antibody or antigen-binding fragment thereof is a bispecific antibody or another antibody mimetic.

44. The antibody, or antigen-binding fragment thereof, of claim 1, wherein the antibody is a monoclonal antibody, a chimeric antibody, a recombinant antibody, an antigen-binding fragment of a recombinant antibody, a humanized antibody, or an antibody displayed upon the surface of a phage or displayed upon the surface of a chimeric antigen receptor (CAR) T cell.

45. The antibody, or antigen-binding fragment thereof, of claim 1, wherein the antibody is an IgG1, IgG2a or IgG2b, IgG3 or IgG4 antibody.

46. The antibody, or antigen-binding fragment thereof, of claim 2, wherein the antibody further comprises a heavy chain constant region comprising the amino acid sequence of SEQ ID NO: 26; and a light chain constant region comprising the amino acid sequence of SEQ ID NO: 27.

47. The antibody, or antigen-binding fragment thereof, of claim 4, wherein the antibody further comprises a heavy chain constant region comprising the amino acid sequence of SEQ ID NO: 26; and a light chain constant region comprising the amino acid sequence of SEQ ID NO: 27.

* * * * *